United States Patent
Chinnaiyan et al.

(10) Patent No.: US 10,167,517 B2
(45) Date of Patent: *Jan. 1, 2019

(54) MIPOL1-ETV1 GENE REARRANGEMENTS

(71) Applicant: THE REGENTS OF THE UNIVERSITY OF MICHIGAN, Ann Arbor, MI (US)

(72) Inventors: Arul M. Chinnaiyan, Plymouth, MI (US); Scott Tomlins, Ann Arbor, MI (US); Saravana Mohan Dhanasekaran, Ann Arbor, MI (US)

(73) Assignee: THE REGENTS OF THE UNIVERSITY OF MICHIGAN, Ann Arbor, MI (US)

(*) Notice: Subject to any disclaimer, the term of this patent is extended or adjusted under 35 U.S.C. 154(b) by 0 days.

This patent is subject to a terminal disclaimer.

(21) Appl. No.: 15/639,583

(22) Filed: Jun. 30, 2017

(65) Prior Publication Data

US 2017/0327901 A1    Nov. 16, 2017

Related U.S. Application Data

(63) Continuation of application No. 15/084,721, filed on Mar. 30, 2016, now Pat. No. 9,719,143, which is a continuation of application No. 12/667,819, filed as application No. PCT/US2008/069201 on Jul. 3, 2008, now Pat. No. 9,303,291.

(60) Provisional application No. 60/958,629, filed on Jul. 6, 2007.

(51) Int. Cl.
   *C12P 19/34* (2006.01)
   *C12Q 1/6886* (2018.01)

(52) U.S. Cl.
   CPC ...... *C12Q 1/6886* (2013.01); *C12Q 2600/118* (2013.01); *C12Q 2600/136* (2013.01); *C12Q 2600/156* (2013.01)

(58) Field of Classification Search
   None
   See application file for complete search history.

(56) References Cited

U.S. PATENT DOCUMENTS

| | | |
|---|---|---|
| 4,109,496 A | 8/1978 | Allemann et al. |
| 4,323,546 A | 4/1982 | Crockford |
| 4,683,195 A | 7/1987 | Mullis et al. |
| 4,683,202 A | 7/1987 | Mullis et al. |
| 4,800,159 A | 1/1989 | Mullis et al. |
| 4,873,191 A | 10/1989 | Wagner et al. |
| 4,965,188 A | 10/1990 | Mullis et al. |
| 4,968,103 A | 11/1990 | McNab et al. |
| 5,130,238 A | 7/1992 | Malek et al. |
| 5,270,184 A | 12/1993 | Walker et al. |
| 5,283,174 A | 2/1994 | Arnold, Jr. et al. |
| 5,283,317 A | 2/1994 | Saifer et al. |
| 5,399,491 A | 3/1995 | Kacian et al. |
| 5,455,166 A | 10/1995 | Walker |
| 5,480,784 A | 1/1996 | Kacian et al. |
| 5,614,396 A | 3/1997 | Bradley et al. |
| 5,631,169 A | 5/1997 | Lakowicz et al. |
| 5,710,029 A | 1/1998 | Ryder et al. |
| 5,776,782 A | 7/1998 | Tsuji |
| 5,814,447 A | 9/1998 | Ishiguro et al. |
| 5,824,518 A | 10/1998 | Kacian et al. |
| 5,854,206 A | 12/1998 | Twardzik et al. |
| 5,856,125 A | 1/1999 | Mavrothalassitis et al. |
| 5,925,517 A | 7/1999 | Tyagi et al. |
| 5,928,862 A | 7/1999 | Morrison |
| 6,034,218 A | 3/2000 | Reed et al. |
| 6,043,033 A | 3/2000 | Bandman et al. |
| 6,080,912 A | 6/2000 | Bremel et al. |
| 6,150,097 A | 11/2000 | Tyagi et al. |
| 6,166,194 A | 12/2000 | Wong |
| 6,198,107 B1 | 3/2001 | Seville |
| 6,262,245 B1 | 7/2001 | Xu et al. |
| 6,303,305 B1 | 10/2001 | Wittwer et al. |
| 6,350,448 B1 | 2/2002 | Bandman et al. |
| 6,395,278 B1 | 5/2002 | Xu et al. |
| 6,444,419 B1 | 9/2002 | Wong |
| 6,534,274 B2 | 3/2003 | Becker et al. |
| 6,541,205 B1 | 4/2003 | Yokoyama et al. |
| 6,828,429 B1 | 12/2004 | Srivastava et al. |
| 6,872,811 B1 | 3/2005 | MacBeth et al. |
| 6,902,892 B1 | 6/2005 | Salceda et al. |
| 7,008,765 B1 | 3/2006 | Bussemakers et al. |
| 7,037,667 B1 | 5/2006 | Afar et al. |
| 7,125,969 B1 | 10/2006 | Benz et al. |
| 7,138,235 B2 | 11/2006 | Bussemakers et al. |
| 7,199,137 B2 | 4/2007 | Dean |
| 7,229,774 B2 | 6/2007 | Chinnaiyan |
| 7,374,885 B2 | 5/2008 | Becker et al. |
| 7,638,278 B2 | 12/2009 | Pollack |
| 7,718,369 B2 | 5/2010 | Tomlins et al. |
| 2002/0119531 A1 | 8/2002 | Bandman et al. |
| 2002/0182586 A1 | 12/2002 | Morris |
| 2003/0103981 A1 | 6/2003 | Spancake |
| 2003/0108963 A1 | 6/2003 | Schlegel et al. |
| 2003/0170625 A1 | 9/2003 | Rosenthal et al. |
| 2003/0175736 A1 | 9/2003 | Chinnaiyan et al. |
| 2003/0185830 A1 | 10/2003 | Xu et al. |

(Continued)

FOREIGN PATENT DOCUMENTS

| | | |
|---|---|---|
| EP | 0684315 | 6/2002 |
| EP | 1409727 | 11/2005 |

(Continued)

OTHER PUBLICATIONS

Affymetrix NETAFFX Details for MG-U7AV2 Accessed from www.affymetrix.com on Aug. 18, 2008.

(Continued)

*Primary Examiner* — Kenneth R Horlick
(74) *Attorney, Agent, or Firm* — Casimir Jones S.C.; David Casimir; Thomas Isenbarger

(57) ABSTRACT

Compositions and methods associated with recurrent MIPOL1-ETV1 genetic rearrangements that are useful for cancer diagnosis and therapy are disclosed.

22 Claims, 8 Drawing Sheets

Specification includes a Sequence Listing.

(56) References Cited

U.S. PATENT DOCUMENTS

| | | |
|---|---|---|
| 2004/0009481 A1 | 1/2004 | Schlegel et al. |
| 2004/0259086 A1 | 12/2004 | Schlegel et al. |
| 2005/0009086 A1 | 1/2005 | Salceda et al. |
| 2005/0042638 A1 | 2/2005 | Arnold, Jr. et al. |
| 2005/0112711 A1 | 5/2005 | Romano et al. |
| 2005/0164223 A1 | 7/2005 | Schalken et al. |
| 2005/0214309 A1 | 9/2005 | Hinrichs et al. |
| 2006/0019256 A1 | 1/2006 | Clarke et al. |
| 2006/0046265 A1 | 3/2006 | Becker et al. |
| 2006/0068425 A1 | 3/2006 | Monanhan et al. |
| 2006/0115821 A1 | 6/2006 | Einstein et al. |
| 2006/0275794 A1 | 12/2006 | Carrino et al. |
| 2007/0042381 A1 | 2/2007 | Bentwich et al. |
| 2007/0212702 A1 | 9/2007 | Tomlins et al. |
| 2008/0269157 A1 | 10/2008 | Srivastava et al. |
| 2009/0208937 A1 | 8/2009 | Chinnaiyan |
| 2009/0239221 A1 | 9/2009 | Chinnaiyan et al. |
| 2010/0063088 A1 | 3/2010 | Wood |
| 2010/0305188 A1 | 12/2010 | Nakano |
| 2011/0065113 A1 | 3/2011 | Chinnaiyan et al. |
| 2013/0040858 A1 | 2/2013 | Tomlins et al. |
| 2016/0097104 A1 | 4/2016 | Tomlins et al. |
| 2016/0319369 A1 | 11/2016 | Tomlins et al. |

FOREIGN PATENT DOCUMENTS

| | | |
|---|---|---|
| WO | 1994010300 | 5/1994 |
| WO | 1998015837 A1 | 4/1998 |
| WO | 1998045420 | 10/1998 |
| WO | 199962942 | 12/1999 |
| WO | 199965929 | 12/1999 |
| WO | 200000605 | 1/2000 |
| WO | 200004149 | 1/2000 |
| WO | 200012758 | 3/2000 |
| WO | 200018961 | 4/2000 |
| WO | 200023111 | 4/2000 |
| WO | 200065067 | 11/2000 |
| WO | 200070092 | 11/2000 |
| WO | 200153836 | 7/2001 |
| WO | 200157058 | 8/2001 |
| WO | 200160860 | 8/2001 |
| WO | 200188124 | 11/2001 |
| WO | 2002010443 A1 | 2/2002 |
| WO | 2003009814 | 2/2003 |
| WO | 2003011888 A1 | 2/2003 |
| WO | 2003053223 | 7/2003 |
| WO | 2004070056 | 2/2004 |
| WO | 2004023973 | 3/2004 |
| WO | 2004074320 | 9/2004 |
| WO | 2004092397 | 10/2004 |
| WO | 2004097358 | 11/2004 |
| WO | 2004113571 | 12/2004 |
| WO | 2005007090 | 1/2005 |
| WO | 2005007830 | 1/2005 |
| WO | 2005003387 | 3/2005 |
| WO | 2005113816 | 12/2005 |
| WO | 2006028655 | 3/2006 |
| WO | WO 2007/033187 A2 | 3/2007 |
| WO | 2009009432 | 1/2009 |
| WO | 2010096660 | 8/2010 |

OTHER PUBLICATIONS

Database EMBL (Online) Mar. 2, 2007 "140298_1373_0575 3' ESTs from HeLa cell *Homo sapiens* Cdna 3', mRNA sequence." XP002597931 retrieved from EBI accession No. EMBL:EH3299833 Nucleotides 2-11.
Tognon Cristina et al., "Expression of the ETV6-NTRK3 gene fusion as a primary event in human secretory breast carcinoma" Cancer Cell (Nov. 2002) 2(5):367-376.
Maher, Christopher, et al., "Transciptome sequencing to detect gene fusions in cancer." Nature (Mar. 2009) 458(7234):97-101.
Maher, Christopher, et al., "Chmimeric transcript discovery by paird-end transcriptome sequencing" Proceedings of the National Academy of Sciences of the United States of America (Jul. 2009) 106(30):12353-12358.
U.S. Office Action dated Sep. 29, 2010 (Sep. 29, 2010), U.S. Appl. No. 12/272,865, filed Nov. 18, 2008 (Nov. 18, 2008) 20 pages.
International Search Report dated May 25, 2010 (May 5, 2010), Application No. PCT/US2009/064957; Filing Date: Nov. 18, 2009 (Nov. 18, 2009) WIPO Publication No. WO 2010/059702 (9 Pages).
Australian Further Office Action dated Jan. 18, 2011 (Jan. 18, 2011), Application No. 2006291054; Filing Date: Sep. 12, 2006 (Sep. 12, 2006) 2 Pages.
Australian Office Action dated Dec. 23, 2009 (Dec. 23, 2009), Application No. 2006291054; Filing Date: Sep. 12, 2006 (Sep. 12, 2006) 3 Pages.
Canadian Office Action dated Nov. 16, 2010 (Nov. 16, 2010), Application No. 2,662,295; Filing Date: Sep. 12, 2006 (Sep. 12, 2006) 11 Pages.
Chinese Office Action dated Dec. 31, 2010 (Dec. 12, 2010), Application No. 200680041826.6; Filing Date: Sep. 12, 2006 (Sep. 12, 2006) Publication No. 101341256 (8 Pages).
U.S. Final Office Action dated Aug. 13, 2009 (Aug. 13, 2009), U.S. Appl. No. 11/519,397, filed Sep. 12, 2006 (Sep. 12, 2006) 36 Pages.
U.S. Office Action dated Feb. 23, 2009 (Feb. 23, 2009), U.S. Appl. No. 11/519,397, filed Sep. 12, 2006 (Sep. 12, 2006) 50 Pages.
International Search Report dated Dec. 4, 2007 (Dec. 4, 2007), Application No. PCT/US2006/035507; Filing Date: Sep. 12, 2006 (Sep. 12, 2006); WIPO Publication No. WO 2007/033187 (5 Pages).
European Office Action dated May 5, 2010 (May 5, 2010), Application No. 08826146.6; Filing Date: Jul. 3, 2008 (Jul. 3, 2008); Publication No. 2171094 (23 Pages).
International Search Report dated Jan. 30, 2009 (Jan. 30, 2009), Application No. PCT/2008/069201; Filing Date: Jul. 3, 2008 (Jul. 3, 2008); WIPO Publication No. WO 2009/009431 (5 Pages).
U.S. Office Action dated Feb. 1, 2011 (Feb. 1, 2011), U.S. Appl. No. 11/825,552, filed Jul. 6, 2007 (Jul. 6, 2007); Publication No. 2009-0208937 (20 Pages).
U.S. Office Action dated: May 26, 2010 (May 26, 2010), U.S. Appl. No. 11/825,552, filed Jul. 6, 2007 (Jul. 6, 2007); Publication No. 2009-0208937 (61 Pages).
International Search Report dated Apr. 15, 2009 (Apr. 15, 2009); Application No. PCT/US2008/069204; Filing Date: Jul. 3, 2008 (Jul. 3, 2008); WIPO Publication No. WO 2009/009432 (8 Pages).
Australian Office Action dated Nov. 5, 2010 (Nov. 5, 2010); Application No. 2007317306; Filing Date: Nov. 8, 2007 (Nov. 8, 2007) 2 Pages.
Canadian Office Action dated Jan. 6, 2011 (Jan. 6, 2011); Application No. 2,668,961; Filing Date: Nov. 8, 2007 (Nov. 8, 2007) 5 Pages.
European Office Action dated Aug. 17, 2010 (Aug. 17, 2010); Application No. 07864115.6; Filing Date: Nov. 8, 2007 (Nov. 8, 2007) Publication No. 2079851 (9 Pages).
International Search Report dated Jul. 28, 2009 (Jul. 28, 2009); Application No. PCT/US2007/084090; Filing Date: Nov. 8, 2007 (Nov. 8, 2007) WIPO Publication No. WO 2008/058239 (5 Pages).
International Search Report dated Nov. 5, 2010 (Nov. 5, 2010); Application No. PCT/US2010/020501; Filing Date: Jan. 8, 2010 (Jan. 8, 2010); WIPO Publication No. WO 2010/081001 (9 Pages).
Goodsell DS (1999), "The Molecular Perspective: The ras Oncogene," Oncologist 4(3): 263-4.
Downward J, ( 2003), " Targeting RAS signalling pathways in cancer therapy," Nat Rev Cancer 3(1): 11-22.
Wennerberg et al., 2005, "The Ras superfamily at a glance," J. Cell Sci, 118 (PT 5): 843-6.
Munemitsu et al., 1990, "Molecular Cloning and Expression of a G25K cDNA, the Human Homolog of the Yeast Cell Cycle Gene CDC42," Mol Cell Biol 10(11): 5977-82.
Sithanandam et al, "Complete coding sequence of a human B-raf cDNA and detection of B-raf protein kinase with isozyme specific antibodies," (1990) Oncogene 5(12): 1775-80.
Sithanandam et al, ( 1992), "B-raf and a B-raf pseudogene are located on 7q in man," Oncogene, 7 (4) 795-9.

(56) References Cited

OTHER PUBLICATIONS

Davies et al, 2002, " Mutations of the BRAF gene in human cancer," Nature 417, (6892): 949-54.
Mark et al, (Apr. 1984), "Primary structure of v-raf: relatedness to the src family of oncogenes," Science 224 (4646) 285-9.
Shimizu et al, (1986), "Structure of the activated c-raf-1 gene from human stomach cancer," Princess Takamatsu Symp, 17: 85-91.
Sridhar et al, ( 2005), "Raf kinase as a target for anticancer therapeutics," Mol Cancer Ther 4(4): 677-85.
Burns Ed., Immunochemical Protocols, 3rd Ed., Humana Press, 2005.
Harlow and Lane, Antibodies: A Laboratory Manual,, Cold Spring Harbor Laboratory (1988).
Kozbor et al, "The production of monoclonal antibodies from human lymphocytes," Immunology Today 4: 72-79 (1983).
Kohler and Milstein, (1975), "Continuous cultures of fused cells secreting antibody of predefined specificity," Nature 256: 495-497.
Mullis et al, (1987), Specific synthesis of DNA in vitro via a polymerase-catalyzed chain reaction, Meth Enzymol. 155: 335-350.
Murakawa et al, (1988), "Direct detection of HIV-1 RNA from AIDS and ARC patient samples," DNA 7: 287-295.
Weiss, (1991), "Hot prospect for new gene amplifier," Science 254: 1292-1293.
Walker G. et al, (1992), "Isothermal in vitro amplification of DNA by a restriction enzyme/DNA polymerase system," Proc Natl Acad Sci USA, 89: 392-396.
Lizardi et al, "Exponential Amplification of Recombinant-RNA Hybridization Probes," Biotechnol 6: 1197-1202 (1988).
Kwoh et al, (1989), "Transcription-based amplification system and detection of amplified human immunodeficiency virus type 1 with a bead-based sandwich hybridization format," Proc Natl Acad Sci USA 86: 1173-1177.
Guatelli et al, (1990), "Isothermal, in vitro amplification of nucleic acids by a multienzyme reaction modeled after retroviral replication," Proc Natl Acad Sci USA 87: 1874-1878.
Nelson, Norman C., et al., (1995) "Detection of Acridinium Esters by Chemiluminescence" Nonisotopic Probing, Blotting, and Sequencing, 2nd Edition, edited by Larry J. Kricka, Ch. 17, pp. 391-428.
Sumerdon et al, "An Optimized Antibody-Chelator Conjugate for Imaging of Carcinoembryonic Antigen with Indium-111," Nucl Med Biol 17: 247-254 (1990).
Griffin et al, (1991), "Initial clinical study of indium-111-labeled clone 110 anticarcinoembryonic antigen antibody in patients with colorectal cancer, " J Clin Oncol, 9: 631-640.
Lauffer, (1991), "Targeted relaxation enhancement agents for MRI," Magnetic Resonance in Medicine 22: 339-342 (1991).
Zervos et al, "Mxi1, a protein that specifically interacts with Max to bind Myo-Max recognition sites," Cell 72: 223-232 (1993).
Ikawa et al., "B-raf, a new member of the raf family, is activated by DNA rearrangement." Mol Cell Biol. Jun. 1988; 8(6):2651-4.
Wan et al., "Mechanism of activation of the RAF-ERK signaling pathway by oncogenic mutations of B-RAF." Cell Mar. 19, 2004; 116(6):855-67.
Olive, "Quantitative methods for the analysis of protein phosphorylation in drug development." Expert Rev Proteomics Oct. 2004; 1(3):327-41.
Bos, "ras Oncogenes in Human Cancer: A Review." Cancer Res 1989; 49:4682-4689.
Kranenburg, "The KRAS oncogene: past, present, and future." Biochim Biophys Acta. Nov. 25, 2005;1756(2):81-2.
Hnatowich et al, "The preparation and labeling of DTPA-coupled albumin." Int J Appl Radiat Isot. May 1982;33(5):327-32.
Khaw et al., "Myocardial infarct imaging of antibodies to canine cardiac myosin with indium-111-diethylenetriamine pentaacetic acid." Science. Jul. 11, 1980; 209(4453):295-7.
Wong et al., "A rapid chemical method of labeling human plasma proteins with 99mTc-pertechnetate at pH 7.4." Int J Appl Radiat Isot. May 1978; 29(4-5):251-3.

Wong et al., "Imaging endocarditis with Tc-99m-labeled antibody—an experimental study: concise communication." J Nuc Med. Mar. 1982;23(3):229-34.
Scheinberg et al. "Tumor imaging with radioactive metal chelates conjugated to monoclonal antibodies." Science. Mar. 19, 1982; 215(4539):1511-3.
Wang et al., "An integrative approach to reveal driver gene fusions from paired-end sequencing data in cancer." Nat Biotechnol. Nov. 2009;27(11):1005-1011.
Cohen et al, "BRAF mutation in papillary thyroid carcinoma." J Natl Cancer Inst. Apr. 16, 2003;95(8):625-7.
Xing, "BRAF mutation in thyroid cancer." Endocr Relat Cancer. Jun. 2005; 12(2):245-62.
Ciampi, "Oncogenic AKAP9-BRAF fusion is a novel mechanism of MAPK pathway activation in thyroid cancer." J Clin Invest. Jan. 2005; 115(1):94-101.
Wang et al., "BRAF mutations in colon cancer are not likely attributable to defective DNA mismatch repair." Cancer Res. Sep. 1, 2003;63(17):5209-12.
Dessars et al., "Chromosomal translocations as a mechanism of BRAF activation in two cases of large congenital melanocytic nevi." J Invest Dermatol. Jun. 2007;127(6):1468-70.
Wilhelm et al., "Preclinical overview of sorafenib, a multikinase inhibitor that targets both Raf and VEGF and PDGF receptor tyrosine kinase signaling." Mol Cancer Ther. Oct. 2008; 7(10):3129-40.
Sala et al., "BRAF silencing by short hairpin RNA or chemical blockade by PLX4032 leads to different responses in melanoma and thyroid carcinoma cells." Mol Cancer Res. May 2008;6(5):751-9.
Warzecha et al., "ESRP1 and ESRP2 are epithelial cell-type-specific regulators of FGFR2 splicing." Mol Cell. Mar. 13, 2009; 33(5):591-601.
Cho et al., "BRAF and KRAS mutations in prostatic adenocarcinoma." Int J Cancer. Oct. 15, 2006;119(8):1858-62.
MacConaill et al., "Profiling critical cancer gene mutations in clinical tumor samples." PLoS One. Nov. 18, 2009; 4(11):e7887.
Garte et al., "Inhibition of H-ras oncogene transformation of NIH3T3 cells by protease inhibitors." Cancer Res. Jun. 15, 1987;47(12):3159-62.
Hoeflich et al., "In vivo antitumor activity of MEK and phosphatidylinositol 3-kinase inhibitors in basal-like breast cancer models." Clin Cancer Res. Jul. 15, 2009;15(14):4649-64.
Pratilas et al., "(V600E)BRAF is associated with disabled feedback inhibition of RAF-MEK signaling and elevated transcriptional output of the pathway." Proc Natl Acad Sci U S A. Mar. 17, 2009;106(11):4519-24.
Jeong et al., "BRAF activation initiates but does not maintain invasive prostate adenocarcinoma." PLoS One. 2008; 3(12):e3949.
Janknecht, "Analysis of the ERK-stimulated ETS transcription factor ER81." Mol Cell Biol. Apr. 1996; 16(4):1550-6.
Varambally et al., "Integrative genomic and proteomic analysis of prostate cancer reveals signatures of metastatic progression." Cancer Cell Nov. 2005, 8:393-406.
*Homo sapiens* angiotensin II receptor-associated protein (AGTRAP), transcript variant 2, mRNA, NCBI Reference Sequence: NM_001040194.1, 4 pages, Jan. 6, 2013.
*Homo sapiens* angiotensin II receptor-associated protein (AGTRAP), transcript variant 4, mRNA, NCBI Reference Sequence: NM_001040196.1, 4 pages, Jan. 6, 2013.
*Homo sapiens* angiotensin II receptor-associated protein (AGTRAP), transcript variant 5, mRNA, NCBI Reference Sequence: NM_001040197.1, 4 pages, Jan. 6, 2013.
*Homo sapiens* angiotensin II receptor-associated protein (AGTRAP), transcript variant 3, mRNA, NCBI Reference Sequence: NM_001040195.1, 4 pages, Jan. 6, 2013.
*Homo sapiens* epithelial splicing regulatory protein 1 (ESRP1), transcript variant 1, mRNA NCBI Reference Sequence: NM_017697.3, 5 pages, Dec. 30, 2012.
*Homo sapiens* v-raf murine sarcoma viral oncogene homolog B1 (BRAF), RefSeqGene on chromosome 7, NCBI Reference Sequence: NG_007873.2, 31 pages, Feb. 3, 2013.

(56) References Cited

OTHER PUBLICATIONS

*Homo sapiens* v-raf murine sarcoma viral oncogene homolog B (BRAF), Mrna NCBI Reference Sequence: NM_004333.4, 6 pages, Oct. 28, 2013.
*Homo sapiens* v-raf-1 murine leukemia viral oncogene homolog 1 (RAF1), RefSeqGene (LRG_413) on chromosome 3 NCBI Reference Sequence: NG_007467.1, 24 pages, Feb. 18, 2013.
*Homo sapiens* v-raf-1 murine leukemia viral oncogene homolog 1 (RAF1), mRNA NCBI Reference Sequence: NM_002880.3, 8 pages, Jan. 28, 2013.
Cruz et al., "Absence of BRAF and NRAS Mutations in Uveal Melanoma." Cancer Research Oct. 1, 2003, 63:5761-5766.
Benner et al., "Evolution, language and analogy in functional genomics." Trends in Genetics Jul. 2001, 17(7):414-418.
Lynch et al., "Activating mutations in the epidermal growth factor receptor underlying responsiveness of non-small-cell lung cancer to gefitinib." N. Engl J Med. May 20, 2004;350(21):2129-39.
Slamon et al., "Use of chemotherapy plus a monoclonal antibody against HER2 for metastatic breast cancer that overexpresses HER2." N. Engl J Med. Mar. 15, 2001;344(11):783-92.
Demetri et al., "Efficacy and safety of imatinib mesylate in advanced gastrointestinal stromal tumors." N. Engl J Med. Aug. 15, 2002;347(7):472-80.
Druker et al., "Five-year follow-up of patients receiving imatinib for chronic myeloid leukemia." N. Engl J Med. Dec. 7, 2006;355(23):2408-17.
Greenman et al., "Patterns of somatic mutation in human cancer genomes." Nature. Mar. 8, 2007;446(7132):153-8.
Weir et al., "Characterizing the cancer genome in lung adenocarcinoma." Nature. Dec. 6, 2007;450(7171):893-8.
Wood et al., "The genomic landscapes of human breast and colorectal cancers." Science. Nov. 16, 2007;318(5853):1108-13.
Barber et al., "Somatic mutations of EGFR in colorectal cancers and glioblastomas." N. Engl J Med. Dec. 30, 2004;351(27):2883.
Futreal et al., "A census of human cancer genes." Nat Rev Cancer. Mar. 2004;4(3):177-83.
Choi et al., "Identification of novel isoforms of the EML4-ALK transforming gene in non-small cell lung cancer." Cancer Res. Jul. 1, 2008;68(13):4971-6.
Perner et al., "EML4-ALK fusion lung cancer: a rare acquired event." Neoplasia. Mar. 2008; 10(3):298-302.
Rikova et al., "Global survey of phosphotyrosine signaling identifies oncogenic kinases in lung cancer." Cell. Dec. 14, 2007;131(6):1190-203.
Zervos et al, "Mxi1, a protein that specifically interacts with Max to bind Myc-Max recognition sites," Cell 72:223-232 (1993).
Madura et al "N-recognin/Ubc2 interactions in the N-end rule pathway," J Biol Chem 2668. 12046-12054 (1993).
Bartel et al, "Elimination of false positives that arise in using the two-hybrid system," Biotechniques 14: 920-924 (1993).
Iwabuchi et al, "Use of the two-hybrid system to identify the domain of p53 involved in oligomerization," Oncogene 8: 1693-1696 (1993).
Karnoub et al, "Ras oncogenes: split personalities," Nat Rev Mol Cell Biol, 9, 517-531 ( 2008).
Rodriguez-Viciana et al, "Cancer targets in the Ras pathway," Cold Spring Harb Symp Quant Biol 70, 461-467 (2005).
Moul et al, "Infrequent RAS oncogene mutations in human prostate cancer," Prostate 20, 327-338 (1992).
Seeburg et al, "Biological properties of human c-Ha-ras1 genes mutated at codon 12," Nature 312, 71-75 (1984).
Schubbert et al, "Hyperactive Ras in developmental disorders and cancer," Nat Rev Cancer 7, 295-308, (2007.
Mullighan et al, "BCR-ABL1 lymphoblastic leukaemia is characterized by the deletion of Ikaros," Nature 453, 110-114(2008).
Graux et al, "Fusion of NUP214 to ABL1 on amplified episomes in T-cell acute lymphoblastic leukemia," Nat Genet 36, 1084-1089 (2004).

Ferreira et al, "Array CGH and gene-expression profiling reveals distinct genomic instability patterns associated with DNA repair and cell-cycle checkpoint pathways in Ewing's sarcoma," Oncogene 27, 2084-2090 ( 2008).
Koivunen et al, "EML4-ALK fusion gene and efficacy of an ALK kinase inhibitor in lung cancer," Clin Cancer Res 14, 4275-4283 (2008).
Stergianou et al, "Fusion of NUP214 to ABL1 on amplified episomes in T-ALL—implications for treatment," Leukemia 19, 1680-1681 (2005).
Graff et al, "Increased AKT activity contributes to prostate cancer progression by dramatically accelerating prostate tumor growth and diminishing p27Kip1 expression," J. Biol Chem 275, 24500-24505 (2000).
Xu et al, "MAPKAPK2 and HSP27 are downstream effectors of p38 MAP kinase-mediated matrix metalloproteinase type 2 activation and cell invasion in human prostate cancer," Oncogene 25, 2987-2998 (2006).
Li et al, "A neoplastic gene fusion mimics trans-splicing of RNAs in normal human cells," Science. Sep. 5, 2008; 321(5894):1357-61.
Der et al, "Transforming genes of human bladder and lung carcinoma cell lines are homologous to the ras genes of Harvey and Kirsten sarcoma viruses," Proc Nail Acad Sci USA 79, 3637-3640 (1982).
Zhu et al, "Transformation potential of Ras isoforms correlates with activation of phosphatidylinositol 3-kinase but not ERK," J Biol Chem 279, 37398-37406 (2004).
Moynihan et al, " Fine-mapping, genomic organization, and transcript analysis of the human ubiquitin-conjugating enzyme gene UBE2L3," Genomics 51, 124-127 (1998).
Hoeller et al., "Targeting the ubiquitin system in cancer therapy," Nature 458, 438-444 (2009).
CA Office Action dated Mar. 29, 2011 (Application No. 2692441).
Barr et al. 1996, "In Vivo Amplification of the PAX3-FKHR and PAX7-FKHR Fusion Genes in Alveolar Rhabdomyosarcoma" Hum. Mol. Genet., 5; 15-21.
Ciampi, R. et al., "BRAF kinase activation via chromosomal rearrangment in radiation-induced and sporadic thyroid cancer." Cell Cycle 2005 4(4): 547-548.
Jones, D.T. et al., "Tandem duplication producing a novel oncogenic BRAF fusion gene defines the majority of pilocytic astrocytomas." Cancer Research 2008 68(21):8673-8677.
Esgueva, R. et al., "Prevalence of TMPRSS2-ERG and SLC45A3-ERG gene fusions in a large prostatectomy cohort." Modern Pathology 2010 23(4):539-546.
Palanisamy, N. "Rearrangments of the RAF kinase pathway in prostate cancer, gastric cancer and melanoma." Nature Medicine 2010 16(7):793-798.
Fradet et al., "APTIMA® PCA3 Molecular Urine Test: Development of Prostate Cancer" European Urology Supplements 2006, 5(2): 275.
Kong et al. "Consistent Detection of TLS/FUS-ERG Chimeric Transcripts in Acute Myeloid Leukemia With t(16;21) (p11;q22) and Identification of a Novel Transcript" Blood. Aug. 1, 1997;90(3):1192-9.
International Search Report dated May 20, 2011 Application No. PCT/US2010/048915; 13 Pages.
U.S. Final Office Action dated Jun. 22, 2011, U.S. Appl. No. 12/272,865.
Australian Office Action dated Jun. 27, 2011 Application No. 2008275304, 2 Pages.
Persing, David H. "In Vitro Nucleic Acid Amplification Techniques" Diagnostic Medical Microbiology: Principles and Applications 1993, 51-87.
U.S. Final Office Action dated Aug. 23, 2011, U.S. Appl. No. 11/825,552, 42 Pages.
European Office Action dated Jun. 28, 2011, Application No. 08772418.3, 4 Pages.
European Office Action dated Jun. 27, 2011, Application No. 07864115.6, 6 Pages.
EP Search Report dated Jul. 8, 2011; Application No. 06814528.3.

(56) References Cited

OTHER PUBLICATIONS

Li J. et al., "PTEN, A Putative Protein Tyrosene Phosphatase Gene Mutated in Human Brain, Breast, and Prostate Cancer." Science, American Association for the Advancement of Science 1997, 275:1943-1947.
Jarrard D.F. et al., "Deltional, Mutational, and Methylation Analyses of CDKN2 (P16/MTS1) in Primary and Metastatic Prostate Cancer." Genes, Chromosomes & Cancer 1997, 19(2)P90-96.
Asatiani E. et al., "Deletion, methylation, and expression of the NKX3.1 suppressor gene in primary human prostate cancer." Cancer Research 2005, 65(4):1164-1173.
Jeon In-Sang et al., "A variant Ewing's sarcoma translocation (7;22) fuses the EWS gene to the ETS gene ETV1." Oncogene 1995, 10(6):1229-1234.
Oikawa T. et al., "Molecular biology of the ETS family of transcription factors." Gene 2003, 303(16):11-34.
Sorenson Poul H B et al., "A Second Ewing's sarcoma translocation, t (21; 22), fuses the EWS gene to anther ETS-family transcription factor, ERG." Nature Genetics 1994, 6(2):146-151.
AU Office Action dated Jul. 5, 2011; Application No. 2009316693; 3 pages.
Cheung et al., "Integration of cytogenetic landmarks into the draft sequence of the human genome." Nature 2001, 409:953-958.
Kuo et al, "Detection of aneuploidy involving chromosomes 13, 18, or 21, by fluorescence in situ hybridization (FISH) to interphase and metaphase amniocytes." Am. J. Human Genet. 1991, 49:112-119.
Ward et al, "Rapid prenatal diagnosis of chromosomal aneuploidies by fluorescence in situ hybridization: clinical experience with 4,500 specimens." Am. J. Hum. Gen. 1993, 52:854-865.
In situ hybridization : medical applications, Edited by G.R. Coulton and J. de Belleroche. Kluwer Academic Publishers, Boston 1992—Book, Reference Not Provided.
In situ hybridization in neurobiology: advances in methodology. Edited by Eberwine, Valentino, Barchas. Oxford University Press Inc., England 1994—Book, Reference Not Provided.
In Situ Hybridization: A Practical Approach. Edited by D. G. Wilkinson. Oxford University Press, USA, 1992—Book, Reference Not Provided.
Wang et al., "Identification and characterization of AGTRAP, a human homolog of murine Angiotensin II Receptor-Associated Protein (Agtrap)" Intl. J Biochem. & Cell Biology 2002, 34:93-102.
Joosten et al., "The production of antibody fragments and anitbody fusion proteins by yeasts and filamentous fungi." Microbial Cell Factories 2003, 2:1-15.
RAF Family Antibody Sampler Kit #2330, Cell Signaling Technology, downloaded from: http://www.cellsignal.com/products/2330.html on May 16, 2013.
Sun et al., "TMPRSS2-ERG fusion, a common genomic alteration in prostate cancer activates C-MYC and abrogates prostate epithelial differentiation." Oncogene Jun. 9, 2008, 27(40):5348-5353.
Makkonen et al., "Identification of ETS-like transcriptome factor 4 as a novel androgen receptor target in prostate cancer cells." Oncogene May 12, 2008, 27(36):4865-4876.
Illum & Jones, "Attachment of Monoclonal Antibodies to Microspheres." Methods in Enzymology 1985, 112: 67-84.
Zucman et al., "Combinatorial generation of variable fusion proteins in the Ewing family of tumours." EMBO Journal 1993, 12(12): 4481-4487.
Park et al., "Antibody-Based Detection of ERG Rearrangement-Positive Prostate Cancer." Neoplasia Jul. 2010, 12(7):590-598.
Schmidt et al., "Quantitative Multi-Gene Expression Profiling of Primary Prostate Cancer." Prostate. 66(14):1521-34 (2006).
Database Entrez Nucleotide (Online) Sep. 21, 2008, "Homo sapiens solute carrier family 45, member 3 (SLC45A3), mRNA; version NM_033102.2 GI: 93277086" Accession No. NM033102 nucleotides 1525-1563 (A).
Edwards et al., "Expression analysis onto microarrays of randomly selected cDNA clones highlights HOXB13 as a marker of human prostate cancer." Br J Cancer. Jan. 31, 2005;92(2):376-81.

Einhauer et al., "The FLAG peptide, a versatile fusion tag for the purification of recombinant proteins." J Biochem Biophys Methods. Oct. 30, 2001;49(1-3):455-65.
Gao et al., "Combinatorial activities of Akt and B-Raf/Erk signaling in a mouse model of androgen-independent prostate cancer." Proc Natl Acad Sci U S A. Sep. 26, 2006;103(39):14477-82.
He, et al., "Profile of Ets gene expression in human breast carcinoma." Cancer Biol Ther. Jan. 2007;6(1):76-82.
Ichikawa et al., "Dual transforming activities of the FUS (TLS)-ERG leukemia fusion protein conferred by two N-terminal domains of FUS (TLS)." Mol Cell Biol. Nov. 1999;19(11):7639-50.
He Jintang et al., "Antibody-independent targeted quantification of TMPRSS2-ERG fusion protein products in prostate cancer." Mol Oncol. Oct. 2014;8(7):1169-80.
Kumar-Sinha Al., "SLC45A3-ELK4 chimera in prostate cancer: spotlight on cis-splicing." Cancer Discov. Jul. 2012;2(7):582-5.
NEB Catalog, 1998/99, pp. 121 and 284.
Singh et al., "Genome-wide expression profiling reveals transcriptomic variation and perturbed gene networks in androgen-dependent and androgen-independent prostate cancer cells." Cancer Lett. Jan. 18, 2008;259(1):28-38.
Tackels-Horne et al., "Identification of differentially expressed genes in hepatocellular carcinoma and metastatic liver tumors by oligonucleotide expression profiling." Cancer. Jul. 15, 2001;92(2):395-405.
Wilson et al., "The membrane-anchored serine protease, TMPRSS2, activates PAR-2 in prostate cancer cells" Biochem. J. (2005) 388: 967-972.
Forrest (1999) "Detection of MLL gene self-fusions by RT-PCR and automated fluorescent DNA-fragment analysis" Cancer Genet Cytogenet 112(2): 181-3.
Pfluger, D. Towards Understanding of Prostate Cancer Heterogenity. Master Thesis. Universitat Ulm and Weill Cornell Medical College. 2008. 58 pages.
Zucman "EWS and ATF-1 gene fusion induced by t(12;22) translocation in malignant melanoma of soft parts" Nature Genetics 4: 341-344 (1993).
Afar, et al., "Catalytic cleavage of the Androgen-regulated TMPRSS2 Protease Results in Its Secretion by Prostate and Prostate Cancer Epithelial," Cancer Research, 2001, pp. 1686-1692 vol. 61.
Ahlers and Figg. "ETS-MPRSS2 Fusion Gene Products in Prostate Cancer." Cancer Biology & Therapy, (2006) 5:3 pp. 254-255.
Cerveira, et al. "TMPRSS2-ERG Gene Fusion Causing ERG Overexpression Precedes Chromosome Copy Number Changes in Prostate Carcinomas and Paired HGPIN Lesions." Neoplasia, (2006) pp. 826-832 vol. 8 (10).
Demichelis, et al. "TMPRSS2: ERG gene fusion associated with lethal prostate cancer in a watchful waiting cohort." Oncogene, (2007) 26(31):4596-4599.
Hendriksen, et al. "Evolution of the Androgen Receptor Pathway during Progression of Prostate Cancer." Cancer Research, (2006) 66(10):5012-5020.
Hermans, et al. "TMPRSS2:ERG Fusion by Translocation or Interstitial Deletion Is Highly Relevant in Androgen-Dependent Prostate Cancer, But Is Bypassed in Late-Stage Androgen Receptor-Negative Prostate Cancer." Cancer D Research (2006) pp. 10658-10663, vol. 66:22.
Iljin, et al. "TMPRSS2 Fusions with Oncogenic ETS Factors in Prostate Cancer Involve Unbalanced Genomic Rearrangements and Are Associated with HDAC1 and Epigenetic Reprogramming." Cancer Research (2006) pp. 10242-10246, vol. 66:21.
Jacquinet, et al. "Cloning and characterization of the cDNA and gene for human epitheliasin." European Journal of Biochemistry (2001) pp. 2687-2699, vol. 268.
Rowley, J.D., "Chromosome translocations: dangerous liaisons revisted", Nature Reviews, Cancer; vol. 1, Dec. 2001, pp. 245-250.
Dhanasekaran et al., "Delineation of prognostic biomarkers in prostate cancer." Nature (2001) 412:822-6.
Mosquera, et al. "Morphological Features of TMPRSS2-ERG gene fusion prostate cancer." Journal of Pathology, (2007) pp. 91-101, vol. 212.

(56) References Cited

OTHER PUBLICATIONS

Oettgen, et al. "PDEF, a Novel Prostate Epithelium-specific Ets Transcription Factor, Interacts with the AndrogenReceptor and Activates Prostate-specific Antigen Gene Expression." Journal of Biological Chemistry, (2000) pp. 1216-1225, vol. 275:2.

Owczarek et al. "Detailed mapping of the ERG-ETS2 interval of human chromosome 21 and comparison with the region of conserved synteny on mouse chromosome 16." Gene, (2004) pp. 65-77, vol. 324.

Perner, et al. "TMPRSS2:ERG Fusion-Associated Deletions Provide Insight into the Heterogeneity of Prostate Cancer." Cancer Res, (2006) pp. 8337-8341, vol. 66:17.

Petrovics et al. "Frequent overexpression of ETS-related gene-1 (ERG1) in prostate cancer transcriptome." Oncogene (2005) pp. 3847-3852, vol. 24.

Reddy, et al. "The erg gene: A human gene related to the ets oncogene." Proc. Natl. Acad. Sci. (1987) pp. 6131-6135, vol. 84, USA.

Rubin and Chinnaiyan. "Bioinformatics approach leads to the discovery of the TMPRSS2:ETS gene fusion in prostate cancer." Laboratory Investigation (2006) pp. 1099-1102, vol. 86.

Vaarala, et al. "The TMPRSS2 Gene Encoding Transmembrane Serine Protease Is Overexpressed in a Majority of Prostate Cancer Patients: Detection of Mutated TMPRSS2 Form in a Case of Aggressive Disease." International Journal of Cancer, (2001) pp. 705-710, vol. 94.

Rao, et al. "erg, a Human ets-Related Gene on Chromosome 21: Alternative Splicing, Polyadenylation, and Translation." Science (1987) pp. 635-639, vol. 237:4815.

Wang, et al. "Expression of Variant TMPRSS2/ERG Fusion Messenger RNAs Is Associated with Aggressive Prostate Cancer," Cancer Res. (2006) pp. 8347-8351, vol. 66: 17.

Bittner et al, "Molecular classification of cutaneous malignant melanoma by gene expression profiling," Nature, vol. 406, Apr. 2000, pp. 536-540.

Chen, et al., "Variation in gene expression patterns in human gastric cancers", Mol Biol of the Cell , vol. 14, Aug. 2003, pp. 3208-3215.

Cheok, et al., Treatment-specific changes in gene expression discriminate in vivo drug response in human leukemia cells, Nature Genetics, vol. 34, May 2003, pp. 85-90, 231.

Deininger, The development of imatinib as a therapeutic agent for chronic myeloid leukemia, Blood, vol. 105, No. 7, Apr. 1, 2005, pp. 2640-2653.

DeKlein, "A cellular oncogene is translocated to the Philadelphia chromosome in chronic myelocytic leukaemia", Nature, vol. 300, Dec. 1982, pp. 765-767.

Dhanasekaran, et al., "Molecular profiling of human prostate tissues: insights into gene expression patterns of prostate development during puberty", The FASEB Journal, vol. 19, No. 2, Feb. 2005, pp. 243-245.

Eisen, et al., "Cluster analysis and display of genome-wide expression patterns", PNAS, vol. 95, No. 25, Dec. 8, 1998, pp. 14863-14868.

Ferrando, et al., "Gene expression signatures define novel oncogenic pathways in T cell acute lymphoblastic leukemia", Cancer Cell, vol. 1, Feb. 2002, pp. 75-87.

Fonseca, et al., "Genetics and Cytogenetics of Multiple Myeloma: A Workshop Report", Cancer Research, vol. 64, Feb. 15, 2004, pp. 1546-1558.

Garraway, et al., "Integrative genomic analyses identify MITF as a lineage survival oncogene amplified in malignant melanoma", Nature, vol. 436, Jul. 7, 2005, pp. 117-122.

Golub, et al., "Molecular classification of cancer: class discovery and class prediction by gene expression monitoring", Science, vol. 286, Oct. 15, 1999, pp. 531-537.

Huang, et al., "Gene expression predictors of breast cancer outcomes", The Lancet, vol. 361, May 10, 2003, pp. 1590-1596.

Jain, et al., "Expression profiles provide insights into early malignant potential and skeletal abnormalities in multiple endocrine neoplasia type 2B syndrome tumors", Cancer Research 64, Jun. 1, 2004, pp. 3907-3913.

Keats, et al., "Overexpression of transcripts originating from the MMSET locus characterizes all (t;14)(p16;q32)-positive multiple myeloma patients", Blood, vol. 105, No. 10, May 15, 2005, pp. 4060-4069.

Lapointe, et al., "Gene expression profiling identifies clinically relevant subtypes of prostate cancer", PNAS, Jan. 20, 2004, vol. 101, No. 3, pp. 811-816.

Latulippe, et al., "Comprehensive gene expression analysts of prostate cancer reveals distinct transcriptional programs associated with metastatic disease", Cancer Research 62, Aug. 1, 2002, pp. 4499-4506.

Lin et al. "Prostate-localized and Androgen-regulated Expression of the Membrane-bound Serine Protease TMPRSS21", Cancer Research 59, Sep. 1, 1999, pp. 4180-4184.

Mitelman, F., "Recurrent chromosome aberrations in cancer", Mutation Research 462 (2000), pp. 247-253.

Paoloni-Giacobino, et al., "Cloning of the TMPRSS2 gene, which encodes a novel serine protease with transmembrane, LDLRA, and SRCR domains and maps to 21q22.3", Genomics, vol. 44, No. 3, Sep. 15, 1997, pp. 309-320.

Paris, et al., "Whole genome scanning identifies genotypes associated with recurrence and metastasis in prostate tumors", Human Molecular Genetics, 2004, vol. 13, No. 13, pp. 1303-1313.

Rabbits, T.H., "Chromosomal translocations in human cancer", Nature, vol. 372, Nov. 10, 1994, pp. 143-149.

Rhodes, et al., "Oncomine: A cancer microarray database and integrated data-mining platform", Neoplasia, vol. 6, No. 1, Jan./Feb. 2004, pp. 1-6.

Rosenwald et al. "The proliferation gene expression signature is a quantitative integrator of oncogenic events that predicts survival in mantle cell lymphoma," Cancer Cell., vol. 3, Feb. 2003, pp. 185-197.

Rowley, "A new Consistent Chromosomal Abnormality in Chronic Myelogenous Leukaemia Identified by Quinacrine Fluorescence and Giemsa Staining", Nature, vol. 243, Jun. 1, 1973, pp. 290-293.

Rubin, et al., "Overexpression, amplification, and androgen regulation of TPD52 in prostate cancer", Cancer Research 64, Jun. 1, 2004, pp. 3814-3822.

Schwartz, et al., "Gene expression in ovarian cancer reflects both morphology and biological behavior, distinguishing clear cell from other poor-prognosis ovarian carcinomas", Cancer Research 62, Aug. 15, 2002, pp. 4722-4729.

Slamon, et al., "Human breast cancer: correlation of relapse and survival with amplification of the HER-2/ neuoncogene", Science, vol. 235, No. 4785, Jan. 9, 1987, pp. 177-182.

Sollar et al., "Confirmation of the High Frequency of the TMPRSS2/ERG Fusion Gene in Prostate Cancer", Genes, Chromosomes & Cancer, vol. 45 (2006), pp. 717-719.

Sotiriou, et al., "Breast cancer classification and prognosis based on gene expression profiles from a population-based study", PNAS, vol. 100, No. 18, Sep. 2, 2003, pp. 10393-10398.

Tian, et al., The role of the Wnt-signaling antagonist DKK1 in the development of osteolytic lesions in multiple myeloma, The New England Journal of Medicine, vol. 349, No. 26, Dec. 25, 2003, pp. 2483-2494.

Wallace, James C. et al., "High-density rhesus macaque Oligonucleotide Microarray design using early-stage rhesus genome sequence information and human genome annotations." BMC Genomics (Jan. 2007) 8:28.

Tusher et al., "Significance analysis of microarrays applied to the ionizing radiation response," PNAS vol. 98, No. 9, Apr. 24, 2001, pp. 5116-5121.

Vasselli, et al., "Predicting survival in patients with metastatic kidney cancer by gene-expression profiling in the primary tumor", PNAS, vol. 100, No. 12, Jun. 10, 2003, pp. 6858-6963.

Velasco, et al., "Identification and validation of novel androgen-regulated genes in prostate cancer", Endocrinology vol. 145(8), 2004, pp. 3913-3924.

(56) References Cited

OTHER PUBLICATIONS

Wang, et al., "Gene-expression profiles to predict distant metastasis of lymph-node-negative primary breast cancer", The Lancet, vol. 365, No. 9460, Feb. 19-25, 2005, pp. 671-679.

Welsh, et al., "Analysis of gene expression identifies candidate markers and pharmacological targets in prostate cancer", Cancer Research, vol. 61, Aug. 15, 2001, pp. 5974-5978.

Wigle, et al., "Molecular profiling of non-small cell lung cancer and correlation with disease-free survival", Cancer Research, vol. 62, Jun. 1, 2002, pp. 3005-3008.

Yoshimoto, et al., Three-color FISH analysis of TMPRRSS2/ERG fusions in prostate cancer indicates that genomic microdeletion of chromosome 21 is associated with rearrangement, Neoplasia, vol. 8, No. 6, Jun. 2006, pp. 465-469.

Zhan, et al. "Global gene expression profiling of multiple myeloma, monoclonal gammopathy of undetermined significance, and normal bone marrow plasma cells", Blood, vol. 99, No. 5, Mar. 1, 2002, pp. 1745-1757.

Abdulkadir, Sarki A., "Conditional Loss of Nkx3.1 in Adult Mice Induces Prostatic Intraepithelial Neoplasia," Molecular and Cellular Biology, Mar. 2002, pp. 1495-1503.

Antoniou, Michael, et al., "Transgenes encompassing dual-promoter CpG islands from the human TBP and HNRPA2B1 loci are resistant to geterochromatin-mediated silencing", Genomics, vol. 82, 2003, pp. 269-279.

Attard, G., et al., "Duplication of the fusion of TMPRSS2 to ERG sequences identifies fatal human prostate cancer", Onogene vol. 27, 2008, pp. 253-263.

Beheshti, B., et al., "Identification of a high Frequency of Chromosomal Rearrangements in the Centromeric Regions of prostate Cancer Cell Lines by Sequential Giemsa Banding and Spectral Karyotyping", Molecular Diagnosis, vol. 5, No. 1,2000, pp. 23-32.

Beheshti, Ben, et al., "Evidence of Chromosomal Instability in Prostate Cancer Determined by Spectral Karyotyping (SKY) and Interphase FISH Analysis", Neoplasia, vol. 3, No. 1, 2001, pp. 62-69.

Cai et al., "ETV1 is a Novel Androgen Receptor-Regulated Gene that Mediates Prostate Cancer Cell Invasion", Molecular Endocrinology 21(8):1835-1846 (2007).

Di Cristofano, Antonio, et al., "Pten and p27KIP1 cooperate in prostate cancer tumor suppression in the mouse", Nature Genetics, vol. 27, Feb. 2001, pp. 222-224.

Eisenberg, Eli and Levanon, Erez Y., "Human housekeeping genes are compact", Trends in Genetics, vol. 19, No. 7, Jul. 2003, pp. 362-365.

Fingleon, Barbara, "Matrix metalloproteinases: roles in cancer and metastasis", Frontiers in Bioscience, vol. 11, Jan. 1, 2006, pp. 479-491.

Gibas, Zenon, "A high-Resolution Study of Chromosome Changes in a Human Prostatic Carcinoma Cell Line (LNCaP)", Cancer Genetics and Cytogenetics, vol. 11, 1984, pp. 399-404.

Guasch, Geraldine, et al., "Endogenous retroviral sequence is fused to FGFR1 kinase in the 8p12 stem-cell myeloproliferative disorder with t(8;19)(p12;q13.3)", Blood, vol. 10, No. Jan. 1, 2003, pp. 286-288.

Kalos, Michael, et al, "Profile Expression is highly Restricted to Normal and Malignant Prostate Tissues", The Prostate 60:246-256 (2004).

Kim, Minjung, et al., "Cooperativity of Nkx3.1 and Pten loss of function in a mouse model of prostate carcinogenesis", PNAS, Mar. 5, 2002, vol. 99, No. 5, pp. 2884-2778.

Mirosevich, Janni, et al., "Expression and role of Foxa proteins in Prostate Cancer", the Prostate 66:1013-1028 (2006).

Mirosevich, Janni, et al., "Expression of Foxa Transcription Factors in the Developing and Adult Murine Prostate", The Prostate 62:339-352 (2005).

Murillo, Horacio, et al., "Prostate Cancer Cells use Genetic an Epigenetic mechanisms for Progression to Androgen Independence", Genes, Chromosomes 7 Cancer, 2006, pp. 702-716.

Ono, Masao, et al., "Stimulation of Expression of the Human Endogenous retrovirus Genome by Female Steroid Hormones in Human Breast Cancer Cell Line T47D", Journal of Virology, Jun. 1987, pp. 2059-2062.

Pang, See-Tong, et al., "Cytogenetic and Expression profiles Associated with Transformation to Androgen-Resistant Prostate Cancer", the Prostate 66: 157-172 (2006).

Patience, Clive, et al., "Human Endogenous Retrovirus Expression and Reverse Transcriptase Activity in the T47D Mammary Carcinoma Cell Line", Journal of Virology, Apr. 1996, pp. 2654-2657.

Weigle, Bernd, et al., "D-PCa-2: A Novel Transript Highly Overexpressed in Human prostate and Prostate Cancer", International Journal of Cancer, vol. 109, 2004, pp. 882-892.

Shai, Xu-Bao, et al., "Molecular Alterations Associated With LNCaP Cell Progression to Androgen Indpendence", The Prostate 60:257-271 (2004).

Smith, Richard, et al., "Expression profiling of EWS/FLI identifies NKX2.2 as a critical target gene in Ewing's sarcoma", Cancer Cell, vol. 9, May 2006, pp. 405-416.

Stauffer, Yves, et al, Digital Expression profiles of human endogenous retroviral families in normal and cancerous tissues, Cancer Immunity 4:2 (2004).

Stavenhagen, Jeffrey B. and Robins, Diane M., "An Ancient Provirus Has Imposed Androgen Regulation on the Adjacent Mouse Sex-Limited Protein Gene", Cell, vol. 55, No. 2, Oct. 21, 1988, pp. 247-254.

Strefford, "The use of multicolor fluorescence technologies in the characterization of prostate carcinoma cell lines: a comparison of multiplex fluorescence in situ hybridization and spectral karyotyping data" Cancer Genetics and Cytogenetics 2001; 124:112-121.

Suzukawa, Kazumi, et al., "Identification of a Breakpoint Cluster Region 3' of the Ribophorin I Gene at 3q21 Associated With the Transcriptional Activation of the EVi1 Gene in Actue Myelogenous Leukemias With inv(3) (q21q26)", Blood, vol. 84, No. 8, Oct. 15, 1994, pp. 2681-2688.

Takaha, Natsuki, et al., "High Mobility Group Protein I(Y): A Candidate Architectural protein for Chromosomal Rearrangements in Prostate Cancer Cells", Cancer Research vol. 62, Feb. 1, 2002, pp. 647-651.

Thalmann, George N., "Androgen-independent Cancer Progression and Bone Metastasis in the LNCaP Model of Human Prostate Cancer", Cancer Research, vol. 54, May 15, 1994, pp. 2577-2581.

Tomlins, Scott A., et al., "Integrative Biology of Prostate Cancer Progression", Annual Review of pathology: Mechanisms of Disease, vol. 1, 2006, pp. 243-271.

Van Bokhoven, Adrie, et al., "Spectral Karyotype (SKY) Analysis of Human Prostate Carcinoma Cell Lines", The Prostate 57:226-244 (2003).

Wang-Johanning, Feng, et al., "Quantitation of HERV-K env gene expression and splicing in human breast", Onogene(2003)22,pp. 1528-1535.

Watson, Spencer K., et al., "Cytogenetically balanced translocations are associated with focal copy number alterations", Hum Genet (2007) 120, pp. 795-805.

Wieser, Rotraud, "Rearrangements of Chromosome Band 3q21 in Myeloid Leukemia", Leukemia 7 Lymphoma, vol. 43,2002, pp. 59-65.

Williams, Steven, et al., "CpG-island fragments from the HNRPA2B1/CBX3 genomic locus reduce silencing and enhance transgene expression from the hCMV promoter/enhancer in mammalian cells", BMC Biotechnology, 2005, 5:17,9 pages.

Xu, Jiangchun, et al., "Identification and Characterization of Prostein, a Novel Prostate-specific Protein", Cancer Research, vol. 61, Feb. 15, 2001, pp. 1563-1568.

Tomlins, Scott A., et al., "Integrative molecular concept modeling of prostate cancer progression", Nature Genetics, vol. 39, No. 1, Jan. 2007, pp. 41-51.

Hartel, "Characterisation of steroid receptor expression in the human prostate carcinoma cell line 22RV1 and quantification of androgen effects on mRNA regulation of prostate-specific genes." J Steroid Biochem Mol Biol. 92 (3):187-97 (2004).

(56) References Cited

OTHER PUBLICATIONS

Schroeder (2007) European Urology 2247-1-4 Comments on Attard et al. (2007), "Duplication of the Fusion of TMPRSS2 to ERG sequences identifies Fatal Human Prostate Cancer", Onogene 2007; 1-11.
Walker Michael G. et al., "Prediction of gene function by genome-scale expression analysis: Prostate cancer-associated genes" vol. 9, pp. 1198-1203, Dec. 1, 1999.
Helgeson Beth et al., "Characterization of TMPRSS2: ETV5 and SLC45A3: ETV5 gene fusions in prostate cancer," Cancer Research Jan 1, 2008, vol. 68, pp. 73-80.
Mehra, Rohit, et al.; "Comprehensive assessment of TMPRSS2 and ETS family gene aberrations in clinically localized prostate cancer"; Modern Pathology: An Official Journal of the United States and Canadian Academy of Pathology, Inc.; May 2007; vol. 20, No. 5; pp. 538-544.
Tomlins, Scott A., et al.; "Recurrent fusion of TMPRSS2 and ETS transcription factor genes in prostate cancer"; Science, American Association for the Advancement of Science; U.S., Washington D.C.; Oct. 28, 2005; vol. 310, No. 5748; pp. 644-648.
Kumar-Sinha, Chandan, et al.; "Evidence of recurrent gene fusions in common epithelial tumors"; Trends in Molecular Medicine; Nov. 2006; vol. 12, No. 11; pp. 529-536.
Laxman, Bharathi, et al.; "Noninvasive detection of TMPRSS2: ERG fusion transcripts in the urine of men with prostate cancer"; Neoplasia; New York, N.Y.; Oct. 2006; vol. 8, No. 10; pp. 885-888.
Tomlins, Scott A., et al.; "TMPRSS2: ETV4 gene fusions define a third molecular subtype of prostate cancer"; Cancer Research, Apr. 1, 2006; vol. 66, No. 7; pp. 3396-3400.
Perner, Sven, et al.; "TMPRSS2-ERG fusion prostate cancer: an early molecular event associated with invasion"; The American Journal of Surgical Pathology; Jun. 2007; pp. 882-888.
Nam, Robert K., et al.; "Expression of TMPRSS2: ERG gene fusion in prostate cancer cells is an important prognostic factor for cancer progression"; Cancer Biology & Theraphy; Jan. 2007; vol. 6, No. 1; pp. 40-45.
Kamnasaran Deepak, et al.; "Rearrangement in the PITX2 and MIPOL1 genes in a patient with a t(4;14) chromosome"; European Journal of Human Genetics: EJHG; Apr. 2003; vol. 11, No. 4; pp. 315-324.
Tomlins, Scott A., et al.; "Distinct classes of chromosomal rearrangements create oncogenic ETS gene fusions in prostate cancer"; Nature; Aug. 2007; vol. 448, No. 7153; pp. 595-599.
Kumar-Sinha, Chandan, et al.; "Recurrent gene fusions in prostate cancer"; Nature Reviews, Cancer; Jul. 2008; vol. 8, No. 7; pp. 497-511.
Liu et al., "Lineage Relationship between LNCaP and LNCaP-Derived Prostate Cancer Cell Lines." The Prostate 2004, 60:98-108.
Pettus et al., "Multiple abnormalities detected by dye reversal genomic microarrays in prostate cancer: A much greater sensitivity than conventional cytogenetics." Cancer Genet. Cytogent. 2004, 154(2):110-118.
Jayaraman et al., "p300/cAMP-responsive Element-binding Protein Interactions with Ets-1 and Ets-2 in the Transcriptional Activation of the Human Stromelysin Promoter." J Biol Chem 1999, 274:17342-17352.
Zou et al., "The Oncogenic TLS-ERG Fusion Protein Exerts Different Effects in Hematopeoitic Cells and Fibroblasts." Molecular and Cellular Biology 2005, 25(14): 6235-6246.
Yang et al., "EWS-Ffli-1 Fushion Protein Interacts with Hyperphosphylated RNA Polymerase II and Interfaces with Serine-Arginine Protein-mediated RNA Splicing." J Biol. Chem. 2009, 275(48):37612-37618.
Lukkonen et al., "Tumor-associated trypsin inhibitor in normal and malignant renal tissue and in serum of renal-cell carcinoma patients." International J of Cancer 1999, 83(4):486-490.
Solakidi et al., "Co-expression of trypsin and tumour-associated trypsin inhibitor (TATI) in colorectal adenocarcinomas." Histology and Histopathology 2003, 18(4):1181-1188.
Fukayama et al., "immunohistochemical localization of pancreatic secretory trypsin inhibitor in fetal and adult pancreatic and extrapancreatic tissues." J Histochemistry and Cytochemistry. 1986 34(2): 227-235.
Wu et al., "Regulation of the ETS transcription factor ER81 by the 90-kDa ribosomal S6 kinase and protein kinase A." The J Biology Chem. 2002, 277(45): 42669-42679.
Brahmajothi et al., "Regional localization of ERG, the channel protein responsible for the rapid component of the delayed rectifier, K+ current in the ferret heart" Circulation Research 1997, 81(1):128-135.
Iftikhar et al., "Disease-and cell-specific expression of GP73 in human liver disease." Am. J Gastroenterology 2004, 99(6):1087-1095.
Harbig et al., "A sequence based identification of the genes detected by probesets on the Affymetrix U133 plus 2.0 array." Nucleic Acids Research. Feb. 2005, 33(3): e31.
Whitehead et al., "Variation induces different gense in the lungs of rates compared with mice." Genome Biology 2005, 6(2), Article R13.
Hoshikawa et al., "Hypoxia induces different genes in the lungs of rats compared with mice." Physical Genomics 2003, 12:209-219.
Affymetrix HG_U95Av2 array showing SPINK1 https://www.affymetrix.com/analysis/netaffx/fullrecord.affx?pk=HG-U95AV2:38582_AT accesses online Jun. 1, 2012.
Affymetrix HG_U95Av2 array showing ERG https://www.affymetrix.com/analysis/netaffx/fullrecord.affx?pk=HG-U95AV2:36383_AT accesses online Jun. 1, 2012.
Seton-Rodgers, "Breast cancer: A striking resemblance" (Nature Reviews) Sep. 2007, vol. 7, p. 638.
Morris et al, (2008), "The discovery and application of gene fusions in prostate cancer," BJU International, vol. 102 p. 276-282.
Rickman et al., (2009) "SLC45A3-ELK4 is a novel and frequent erythroblast transformation-specific fusion transcript in prostate cancer," Cancer Research, 69, p. 2734-2738.
Han Bo et al., "A Fluoresence in SITU Hybridization Screen for E26 Transformation-Specific Aberrations: Identification of DDX5-ETV4 Fusion Protein in Prostate Cancer" Cancer Research Sep. 2008 68(18):7629-7637.
Hermans Karing G et al., "Truncated ETV1, Fused to Novel Tissued-Specific Gense, and Full Length ETV1 in Prostate Cancer" Cancer Research Sep. 2008 68:7541-7549.
Pflueger Dorothee et al., "N-MYC Downstream Regulated Gene 1 (NDRG1) is fused to ERG in Prostate Cancer." Neoplasia (Aug. 2009) 11(8):804.
Singh, Jas et al., "Annotation of androgen dependence to human prostate cancer associated genes by microarray analysis of mouse prostate" Cancer Letters 2006, 237:298-304.
Singh, Jas et al, "RNA Reference mediated silencing of SPINK reduces invasion and proliferation of prostate cancer cells." Proceedings of the Annual Meeting of the American Association for Cancer Research, American Association for Cancer Research, (Apr. 2006) 47(1):823 US.
Bjartell, A. et al., "Tumor-Associated Trypsin Inhibitor (TATI, PSTI, SPINK1) Expression in Prostate Cancer is Related to Tumor Grade" European Urology Supplements (Sep. 2006) 5(14):79.
Li Shijun et al., "Application of genomic technologies to human prostate cancer" OMICS A Journal of Integrative Biology (Sep. 2006) 10(3):261-275.
Laxman, Bharathi, et al., "A First-Generation Mulitplex Biomarker Analysis of Urine for the Early Detection of Prostate Cancer." Cancer Research (Feb. 2008) 68(3):645-649.
Rhodes et al., "Large-scale meta-analysis of cancer microarray data identifies common transcriptional profiles of neoplastic transformation and progression" Proc Natl Acad Sci USA (2004) 101:9309.
Haverback et al., "Trypsin, Trypsinogen and Trypsin Inhibitor in Human Pancreatic Juice." Am J. Med. (1960) 29:421-433.
Kazal et al., "Isolation of a Crystalline Trypsin Inhibitor-Anticoagulant Protein from Pancreas." Journal of the American Chemical Society (1948) 70:3034-3040.
Paju et al., "Biochemistry and Clinical Role of Trypsinogens and Pancreatic Secretory Trypsin Inhibitor." Crit. Rev. Clin. Lab Sci. (2006) 43:103-42.

(56) References Cited

OTHER PUBLICATIONS

Greene et al., "Human Pancreatic Secretory Trypsin Inhibitor." Methods Enzymol (1976) 45:813-25.
Stenman, "Tumor-associated Trypsin Inhibitor." Clin Chem (2002) 48:1206-9.
Schalken, "Molecular Diagnostics and Therapy of Prostate Cancer: New Avenues." Eur. Ural 1998 34 (Suppl.3):3-6.
Bussemakers et al., "DD3:A new Prostate-specific Gene, Highly Overexpressed in Prostate Cancer, " Cancer Res. (1999) 59:5975-5979.
Bussemakers et al., "Changes in Gene Expression and Targets for Therapy." Eur. Urol. (1999) 35:408-412.
De Kok et al., "DD3PCA3, a Very Sensitive and Specific Marker to Detect Prostate Tumors." Caner Res. (2002) 2695-8.
Block et al., "Use of targeted glycoroteomics to identify serum glycoproteins that correlate with liver cancer in woodchucks and humans." Proc Natl Acad Sci USA (2005) 102:779-784.
Kladney et al., "GP73, a novel Golgi-localized protein unregulated by viral infection." Gene 2000 249:53-65.
Yu et al., "Gene expression Alterations in Prostate Cancer Predicting Tumor Aggression and Preceding Development of Malignancy." J Clin Onc (Jul. 2004) 22(14):2790-2799.
Glinsky et al., "Gene expression profiling predicts clinical outcome of prostate cancer." J Clin Invest (2004) 113:913-23.
Vanaja et al., "Transcriptional Silencing of Zinc Finger Protein 185 Identified by Expressing Profiling in Associated with Prostate Cancer Progression." Cancer Res (2003) 63:3877-82.
Bittner et al., "A window on the dynamics of biological switches." Biotechnol. (2005) 23:183-4.
Su et al., "Molecular Classification of Human Carcinomas by Use of Gene Expression Signatures." Cancer Res 61:7388-93 (2001).
Andren et al., "How Well Does the Gleason Score Predict Prostate Cancer Death? A 20-Year Follow up of a Population Based Cohort in Sweden." J Urol (2006) 175:1337-40.
Johansson et al., "Natural History of Early, Localized Prostate Cancer." JAMA (2004) 291: 2713-9.
Han et al., "Long-term Biochemical Disease-Free and Cancerspecific Survival Following Anatomic Radical Retropubic Prostatectomy." Urol Clin North Am (2001) 28:555-65.
Hull et al., G.W. et al., "Cancer Control with Radical Prostatectomy Alone in 1,000 Consecutive Patients." J. Urol (2002) 167:528-34.
Kattan et al., "Postoperative Nomogram for Disease Recurrence After Radical Prostatectomy for Prostate Cancer." J. Clinical Oncol. (1999) 17:1499-507.
Kattan et al., "The Addition of Interleukin-6 Soluble Receptor and Transforming Growth Factor Beta1 Improves a Preoperative Nomogram for Predicting Biochemical Progression in Patients with Clinically Localized Prostate Cancer." J Clin Oncol (2003) 21:3537-9.
Paju et al., "Increased Expression of Tumor-Associated Trypsin Inhibitor, TATI, in Prostate Cancer and in Androgen-Independent 22Rv1 Cells." Eur Urol (2007) 52:1670-1681.
Sramkoski, R.M. et al., "A New Human Prostate Carcinoma Cell Line 22RV1." In Vitro Cell Dev Biol Anim (1999) 35:403-9.
Tomlins et al., "Whole Transcriptome Amplification for Gene Expression Profiling and Development of Molecular Archives." Neoplasia (2006) 8:153-62.
Vandesompele et al., "Accurate normalization of real-time quantitative RT-PCR data by geometric averaging of multiple internal control genes." Genome Biol 2002; 3 Research 0034.1-0034.11.
Kumar-Sinha et al., "Elevated Methylacyl-CoA Racemase Enzymatic Activity in Prostate Cancer." Am J. Path (2004) 164:787-93.
Specht et al., "Quantitative Gene Expression Analysis in Microdissected Archival Formalin-Fixed and Paraffin-Embedded Tumor Tissue." Am J. Pathol. 2001, 158:419-29.
Rubin et al., "Methylacyl Coenzyme A Racemase as a Tissue Biomarker for Prostate Cancer." JAMA (2002) 287:1662-70.
Faith et al., "Trefoil Factor 3 Overexpression in Prostate Carcinoma: Prognostic Importance Using Tissue Microarrays." Prostate (2004) 61:215-27.

Garraway et al., "Trefoil Factor 3 Is Overexpressed in Human Prostate Cancer." Prostate 2004 61:209-14.
Hessels et al., "DD3PCA3-based Molecular Urine Analysis for the Diagnosis of Prostate Cancer." Eur Urol (2003) 44:8-16.
Fradet et al., "UPM3, A new molecular urine test for the detection of Prostate Cancer." Urology (2004) 64:311-5 Discussion 5-6.
Groskopf et al., "APTIMA PCA3 Molecular Urine Test: Development of a Method to Aid in the Diagnosis of Prostate Cancer." Clin Chem 2006 52:1089-95.
Marks et al., "PCA3 Molecular Urine Assay for Prostate Cancer in Men Undergoing Repeat Biopsy." Urology (2007) 69:532-5.
DeLong et al., "Comparing the Areas Under Two or More Correlated Receiver Operating Characteristic Curves: A Nonparametric Approach." Biometrics (1988) 44:837-45.
Affymetrix NETAFXX Details for MG-U7AV2 Microarray Specifically Showing that EVT1 is present on the array accessed from www.affymetrix.com on May 1, 2009.
Affymetrix NETAFXX Details for MG-U7AV2 Microarray Specifically Showing that ERG is present on the array accessed from www.affymetrix.com on May 1, 2009.
Soda et al., "Identification of the transforming EML4-ALK fusion gene in non-small-cell lung cancer." Nature. Aug. 2, 2007;448(7153):561-6.
Campbell et al., "Identification of somatically acquired rearrangements in cancer using genome-wide massively parallel paired-end sequencing." Nat Genet. Jun. 2008;40(6):722-9.
Parsons et al., "An integrated genomic analysis of human glioblastoma multiforme." Science. Sep. 26, 2008;321(5897):1807-12.
Strausberg et al., "The cancer genome anatomy project: building an annotated gene index." Trends Genet. Mar. 2000;16(3):103-6.
Lin et al., "Prostate-localized and androgen-regulated expression of the membrane-bound serine protease TMPRSS2." Cancer Res. Sep. 1, 1999;59(17):4180-4.
GenBank: AAC51784.1, serine protease [*Homo sapiens*], 2 pages, Oct. 10, 1997.
GenBank: U75329.1, Human serine protease mRNA, complete cds, 2 pages, Oct. 10, 1997.
Ota et al., "Complete sequencing and characterization of 21,243 full-length human cDNAs." Nat Genet. Jan. 2004;36(1):40-5.
Smith et al., "Cloning, expression, and characterization of a soluble calcium-activated nucleotidase, a human enzyme belonging to a new family of extracellular nucleotidases." Arch Biochem Biophys. Oct. 1, 2002;406(1):105-15.
Genbank Accession NM_014685.3, *Homo sapiens* homocysteine-inducible, endoplasmic reticulum stress-inducible, ubiquitin-like domain member 1 (HERPUD1), transcript variant 1, mRNA, 4 pages, Mar. 27, 2013.
Genbank Accession NM_004449.4, *Homo sapiens* v-ets erythroblastosis virus E26 oncogene homolog (avian) (ERG), transcript variant 2, mRNA, 6 pages, Mar. 27, 2013.
Genbank Accession M17254.1, Human erg2 gene encoding erg2 protein, complete cds, 2 pages, Nov. 8, 1994.
Swiss Protein Acc. No. P11308.2, RecName: Full=Transcriptional regulator ERG; AltName: Full=Transforming protein ERG, 6 pages, Mar. 6, 2013.
Genbank Accession No. NC_000007.11, *Homo sapiens* chromosome 7, complete sequence, 1 page, Oct. 25, 2004.
Genbank Accession No. NT_007819.15, *Homo sapiens* chromosome 7 genomic contig, 4 pages, Aug. 20, 2004.
Genbank Accession No. NM_004956.4, *Homo sapiens* ets variant 1 (ETV1), transcript variant 1, mRNA, 6 pages, Mar. 24, 2013.
Genbank Accession No. NP_004947.2, ETS translocation variant 1 isoform a [*Homo sapiens*], 5 pages, Mar. 24, 2013.
Genbank Accession No. NC_000017.9, *Homo sapiens* chromosome 17, reference assembly, complete sequence, Mar. 3, 2008.
Genbank Accession No. NT_010783.14, *Homo sapiens* chromosome 17 genomic contig, reference assembly, 3 pages, Feb. 29, 2008.
Genbank Accession No. NT_086880.1, 3 pages, Aug. 20, 2004.
Genbank Accession No. NM_001986.2, *Homo sapiens* ets variant 4 (ETV4), transcript variant 1, mRNA, 4 pages, Mar. 17, 2013.

(56) References Cited

OTHER PUBLICATIONS

UniProtKB/Swiss-Prot: P432683, RecName: Full=ETS translocation variant 4; AltName: Full=Adenovirus E1A enhancer-binding protein; AltName: Full=E1A-F; AltName: Full=Polyomavirus enhancer activator 3 homolog; Short=Protein PEA3, 6 pages, Mar. 6, 2013.

NC_000003.10, Homo sapiens chromosome 3, reference assembly, complete sequence, 1 page, Mar. 3, 2008.

NM_004454.2, Homo sapiens ets variant 5 (ETV5), mRNA, 5 pages, Mar. 31, 2013.

Klinger et al., "Rapid detection of chromosome aneuploidies in uncultured amniocytes by using fluorescence in situ hybridization (FISH)." Am J Hum Genet. Jul. 1992;51(1):55-65.

McConnell et al., "The cytosensor microphysiometer: biological applications of silicon technology." Science. Sep. 25, 1992;257(5078):1906-12.

Sjolander et al., "Integrated fluid handling system for biomolecular interaction analysis." Anal Chem. Oct. 15, 1991;63(20):2338-45.

Szabo et al., "Surface plasmon resonance and its use in biomolecular interaction analysis (BIA)." Curr Opin Struct Biol. Oct. 1995;5(5):699-705.

Rubin et al.,Rapid ("warm") autopsy study for procurement of metastatic prostate cancer. Clin Cancer Res. Mar. 2000;6(3):1038-45.

Karolchik et al, "The UCSC Table Browser data retrieval tool." Nucleic Acids Res. Jan. 1, 2004;32(Database issue):D493-6.

GenBank: DQ204772.1, Homo sapiens TMPRSS2/ERGa fusion transcript, 1 page, Nov. 2, 2005.

GenBank: M30829.1, Human bcr/abl fusion protein mRNA, partial cds, clone K28, 1 page, Feb. 14, 1996.

Communi et al., "Cotranscription and intergenic splicing of human P2Y11 and SSF1 genes." J Biol Chem. May 11, 2001;276(19):16561-6.

Shtivelman et al., "Fused transcript of abl and bcr genes in chronic myelogenous leukaemia." Nature. Jun. 13-19, 1985;315(6020):550-4.

Kato et al., "Activation of Holliday junction-recognizing protein involved in the chromosomal stability and immortality of cancer cells." Cancer Res. Sep. 15, 2007;67(18):8544-53.

Bashir et al., "Evaluation of paired-end sequencing strategies for detection of genome rearrangements in cancer." PLoS Comput Biol. Apr. 25, 2008;4(4):e1000051.

Yu et al., "Integrative genomics analysis reveals silencing of beta-adrenergic signaling by polycomb in prostate cancer." Cancer Cell. Nov. 2007;12(5):419-31.

Mitelman et al., "Fusion genes and rearranged genes as a linear function of chromosome aberrations in cancer." Nat Genet. Apr. 2004;36(4):331-4.

Mitelman et al., "Prevalence estimates of recurrent balanced cytogenetic aberrations and gene fusions in unselected patients with neoplastic disorders." Genes Chromosomes Cancer. Aug. 2005;43(4):350-66.

Volik et al., "End-sequence profiling: sequence-based analysis of aberrant genomes." Proc Natl Acad Sci U S A. Jun. 24, 2003;100(13):7696-701.

Tuzun et al., "Fine-scale structural variation of the human genome" Nat Genet. Jul. 2005;37(7):727-32.

Ruan et al., "Fusion transcripts and transcribed retrotransposed loci discovered through comprehensive transcriptome analysis using Paired-End diTags (PETs)." Genome Res. Jun. 2007;17(6):828-38.

Barlund et al, "Cloning of BCAS3 (17q23) and BCAS4 (20q13) genes that undergo amplification, overexpression, and fusion in breast cancer." Genes Chromosomes Cancer. Dec. 2002;35(4):311-7.

Montagut et al., "Targeting the RAF-MEK-ERK pathway in cancer therapy." Cancer Letters Feb. 2009, 283(2):125-134.

Hampton et al., "A sequence-level map of chromosomal breakpoints in the MCF-7 breast cancer cell line yields insights into the evolution of a cancer genome." Genome Res. Feb. 2009;19(2):167-77.

Hahn et al., "Finding fusion genes resulting from chromosome rearrangement by analyzing the expressed sequence databases." Proc Natl Acad Sci U S A. Sep. 7, 2004;101(36):13257-61.

Shadeo & Lam. "Comprehensive copy number profiles of breast cancer cell model genomes." Breast Cancer Res. 2006;8(1):R9.

Huang et al., "Whole genome DNA copy number changes identified by high density oligonucleotide arrays." Hum Genomics. May 2004;1(4):287-99.

Neve et al., "A collection of breast cancer cell lines for the study of functionally distinct cancer subtypes." Cancer Cell. Dec. 2006;10(6):515-27.

Bodmer et al., "Disruption of a novel MFS transporter gene, DIRC2, by a familial renal cell carcinoma-associated t(2;3)(q35;q21)." Hum Mol Genet. Mar. 15, 2002;11(6):641-9.

SEQUENCE LISTING

```
<160> NUMBER OF SEQ ID NOS: 108

<210> SEQ ID NO 1
<211> LENGTH: 22
<212> TYPE: DNA
<213> ORGANISM: Artificial Sequence
<220> FEATURE:
<223> OTHER INFORMATION: Synthetic

<400> SEQUENCE: 1
ctaccccatg gaccacagat tt                                             22

<210> SEQ ID NO 2
<211> LENGTH: 22
<212> TYPE: DNA
<213> ORGANISM: Artificial Sequence
<220> FEATURE:
<223> OTHER INFORMATION: Synthetic

<400> SEQUENCE: 2
cttaaagcct tgtggtggga ag                                             22

<210> SEQ ID NO 3
<211> LENGTH: 24
<212> TYPE: DNA
<213> ORGANISM: Artificial Sequence
<220> FEATURE:
<223> OTHER INFORMATION: Synthetic

<400> SEQUENCE: 3
cgcagagtta tcgtgccagc agat                                           24

<210> SEQ ID NO 4
<211> LENGTH: 24
<212> TYPE: DNA
<213> ORGANISM: Artificial Sequence
<220> FEATURE:
<223> OTHER INFORMATION: Synthetic

<400> SEQUENCE: 4
ccatattctt tcaccgccca ctcc                                           24

<210> SEQ ID NO 5
<211> LENGTH: 23
<212> TYPE: DNA
<213> ORGANISM: Artificial Sequence
<220> FEATURE:
<223> OTHER INFORMATION: Synthetic

<400> SEQUENCE: 5
cgactggagc acgaggacac tga                                            23
```

<210> SEQ ID NO 6
<211> LENGTH: 24
<212> TYPE: DNA
<213> ORGANISM: Artificial Sequence
<220> FEATURE:
<223> OTHER INFORMATION: Synthetic

<400> SEQUENCE: 6
catggactgt ggggttcttt cttg                                            24

<210> SEQ ID NO 7
<211> LENGTH: 26
<212> TYPE: DNA
<213> ORGANISM: Artificial Sequence
<220> FEATURE:
<223> OTHER INFORMATION: Synthetic

<400> SEQUENCE: 7
agacatctgg cgttggtaca taggac                                          26

<210> SEQ ID NO 8
<211> LENGTH: 25
<212> TYPE: DNA
<213> ORGANISM: Artificial Sequence
<220> FEATURE:
<223> OTHER INFORMATION: Synthetic

<400> SEQUENCE: 8
gagtcccaag tacgtccacg gtcag                                           25

<210> SEQ ID NO 9
<211> LENGTH: 27
<212> TYPE: DNA
<213> ORGANISM: Artificial Sequence
<220> FEATURE:
<223> OTHER INFORMATION: Synthetic

<400> SEQUENCE: 9
ggactgtggg gttctttctt gattttc                                         27

<210> SEQ ID NO 10
<211> LENGTH: 20
<212> TYPE: DNA
<213> ORGANISM: Artificial Sequence
<220> FEATURE:
<223> OTHER INFORMATION: Synthetic

<400> SEQUENCE: 10
tgcgggaaat cgggctgaag                                                 20

<210> SEQ ID NO 11
<211> LENGTH: 28
<212> TYPE: DNA
<213> ORGANISM: Artificial Sequence
<220> FEATURE:
<223> OTHER INFORMATION: Synthetic

<400> SEQUENCE: 11
ttttcctgac atttgttggt ttctcgtt                                        28

<210> SEQ ID NO 12
<211> LENGTH: 19
<212> TYPE: DNA
<213> ORGANISM: Artificial Sequence
<220> FEATURE:
<223> OTHER INFORMATION: Synthetic

<400> SEQUENCE: 12
cgctggctcc gggtgacag                                                    19

<210> SEQ ID NO 13
<211> LENGTH: 27
<212> TYPE: DNA
<213> ORGANISM: Artificial Sequence
<220> FEATURE:
<223> OTHER INFORMATION: Synthetic

<400> SEQUENCE: 13
gtggggttct tcttgattt tcagtgg                                            27

<210> SEQ ID NO 14
<211> LENGTH: 24
<212> TYPE: DNA
<213> ORGANISM: Artificial Sequence
<220> FEATURE:
<223> OTHER INFORMATION: Synthetic

<400> SEQUENCE: 14
caactaacac tgcggcttcc tgag                                              24

<210> SEQ ID NO 15
<211> LENGTH: 23
<212> TYPE: DNA
<213> ORGANISM: Artificial Sequence
<220> FEATURE:
<223> OTHER INFORMATION: Synthetic

<400> SEQUENCE: 15
cattcccact tgtggcttct gat                                               23

<210> SEQ ID NO 16
<211> LENGTH: 25
<212> TYPE: DNA
<213> ORGANISM: Artificial Sequence
<220> FEATURE:
<223> OTHER INFORMATION: Synthetic

<400> SEQUENCE: 16
caggagtgta cgggaatgtg atggt                                             25

<210> SEQ ID NO 17
<211> LENGTH: 24
<212> TYPE: DNA
<213> ORGANISM: Artificial Sequence
<220> FEATURE:
<223> OTHER INFORMATION: Synthetic

<400> SEQUENCE: 17
gattagccgt ctgccctcat ttgt                                              24

<210> SEQ ID NO 18
<211> LENGTH: 29
<212> TYPE: DNA
<213> ORGANISM: Artificial Sequence
<220> FEATURE:
<223> OTHER INFORMATION: Synthetic

<400> SEQUENCE: 18
tgccatgaag atcagtacta cagcagaat                                         29

```
<210> SEQ ID NO 19
<211> LENGTH: 25
<212> TYPE: DNA
<213> ORGANISM: Artificial Sequence
<220> FEATURE:
<223> OTHER INFORMATION: Synthetic

<400> SEQUENCE: 19
gtggcccata aactcatgaa tcacc                                          25

<210> SEQ ID NO 20
<211> LENGTH: 21
<212> TYPE: DNA
<213> ORGANISM: Artificial Sequence
<220> FEATURE:
<223> OTHER INFORMATION: Synthetic

<400> SEQUENCE: 20
cagatcgtgg ccggtggttc t                                              21

<210> SEQ ID NO 21
<211> LENGTH: 26
<212> TYPE: DNA
<213> ORGANISM: Artificial Sequence
<220> FEATURE:
<223> OTHER INFORMATION: Synthetic

<400> SEQUENCE: 21
gggtgcatca ggcaaatttc tacaag                                         26

<210> SEQ ID NO 22
<211> LENGTH: 27
<212> TYPE: DNA
<213> ORGANISM: Artificial Sequence
<220> FEATURE:
<223> OTHER INFORMATION: Synthetic

<400> SEQUENCE: 22
caacaacaaa atgaggaact ggctact                                        27

<210> SEQ ID NO 23
<211> LENGTH: 25
<212> TYPE: DNA
<213> ORGANISM: Artificial Sequence
<220> FEATURE:
<223> OTHER INFORMATION: Synthetic

<400> SEQUENCE: 23
attccatatt tgctcgctct gtcag                                          25

<210> SEQ ID NO 24
<211> LENGTH: 24
<212> TYPE: DNA
<213> ORGANISM: Artificial Sequence
<220> FEATURE:
<223> OTHER INFORMATION: Synthetic

<400> SEQUENCE: 24
gaagatggaa gggcatgaaa ccag                                           24

<210> SEQ ID NO 25
<211> LENGTH: 20
<212> TYPE: DNA
<213> ORGANISM: Artificial Sequence
<220> FEATURE:
<223> OTHER INFORMATION: Synthetic
```

<400> SEQUENCE: 25
gctgaccggg acggaggagt                                              20

<210> SEQ ID NO 26
<211> LENGTH: 19
<212> TYPE: DNA
<213> ORGANISM: Artificial Sequence
<220> FEATURE:
<223> OTHER INFORMATION: Synthetic

<400> SEQUENCE: 26
tcgtgggcga ggggctgta                                               19

<210> SEQ ID NO 27
<211> LENGTH: 25
<212> TYPE: DNA
<213> ORGANISM: Artificial Sequence
<220> FEATURE:
<223> OTHER INFORMATION: Synthetic

<400> SEQUENCE: 27
catccgaacg ccttcatcat agtgt                                        25

<210> SEQ ID NO 28
<211> LENGTH: 27
<212> TYPE: DNA
<213> ORGANISM: Artificial Sequence
<220> FEATURE:
<223> OTHER INFORMATION: Synthetic

<400> SEQUENCE: 28
cttttctcta gggtgaaggg actctcg                                      27

<210> SEQ ID NO 29
<211> LENGTH: 26
<212> TYPE: DNA
<213> ORGANISM: Artificial Sequence
<220> FEATURE:
<223> OTHER INFORMATION: Synthetic

<400> SEQUENCE: 29
cttcacccac aaggctcact gtagac                                       26

<210> SEQ ID NO 30
<211> LENGTH: 27
<212> TYPE: DNA
<213> ORGANISM: Artificial Sequence
<220> FEATURE:
<223> OTHER INFORMATION: Synthetic

<400> SEQUENCE: 30
gctttggctt tgttactttt gatgacc                                      27

<210> SEQ ID NO 31
<211> LENGTH: 29
<212> TYPE: DNA
<213> ORGANISM: Artificial Sequence
<220> FEATURE:
<223> OTHER INFORMATION: Synthetic

<400> SEQUENCE: 31
gcctttctta cttctgcatt atgaccatt                                    29

```
<210> SEQ ID NO 32
<211> LENGTH: 25
<212> TYPE: DNA
<213> ORGANISM: Artificial Sequence
<220> FEATURE:
<223> OTHER INFORMATION: Synthetic

<400> SEQUENCE: 32
aaggacgtgc aaggatgttt ttatt                                             25

<210> SEQ ID NO 33
<211> LENGTH: 20
<212> TYPE: DNA
<213> ORGANISM: Artificial Sequence
<220> FEATURE:
<223> OTHER INFORMATION: Synthetic

<400> SEQUENCE: 33
atgggaagat gggggctgtt                                                   20

<210> SEQ ID NO 34
<211> LENGTH: 30
<212> TYPE: DNA
<213> ORGANISM: Artificial Sequence
<220> FEATURE:
<223> OTHER INFORMATION: Synthetic

<400> SEQUENCE: 34
gtcaatggct aaaagatgga taaaagtgga                                        30

<210> SEQ ID NO 35
<211> LENGTH: 30
<212> TYPE: DNA
<213> ORGANISM: Artificial Sequence
<220> FEATURE:
<223> OTHER INFORMATION: Synthetic

<400> SEQUENCE: 35
cagatagaag aggggttagc aaaatgtgtt                                        30

<210> SEQ ID NO 36
<211> LENGTH: 26
<212> TYPE: DNA
<213> ORGANISM: Artificial Sequence
<220> FEATURE:
<223> OTHER INFORMATION: Synthetic

<400> SEQUENCE: 36
cagaaggcaa atgtgagagg atagtc                                            26

<210> SEQ ID NO 37
<211> LENGTH: 23
<212> TYPE: DNA
<213> ORGANISM: Artificial Sequence
<220> FEATURE:
<223> OTHER INFORMATION: Synthetic

<400> SEQUENCE: 37
ctggatctgt aacacccgtg agc                                               23

<210> SEQ ID NO 38
<211> LENGTH: 26
<212> TYPE: DNA
<213> ORGANISM: Artificial Sequence
<220> FEATURE:
<223> OTHER INFORMATION: Synthetic
```

<400> SEQUENCE: 38
aaaaagcaaa gacaagaccg tggatt        26

<210> SEQ ID NO 39
<211> LENGTH: 27
<212> TYPE: DNA
<213> ORGANISM: Artificial Sequence
<220> FEATURE:
<223> OTHER INFORMATION: Synthetic

<400> SEQUENCE: 39
gaactacctg cgtgctgact tggagat        27

<210> SEQ ID NO 40
<211> LENGTH: 30
<212> TYPE: DNA
<213> ORGANISM: Artificial Sequence
<220> FEATURE:
<223> OTHER INFORMATION: Synthetic

<400> SEQUENCE: 40
aaaaggcaaa gagggttaa aacatacata        30

<210> SEQ ID NO 41
<211> LENGTH: 24
<212> TYPE: DNA
<213> ORGANISM: Artificial Sequence
<220> FEATURE:
<223> OTHER INFORMATION: Synthetic

<400> SEQUENCE: 41 aaccctcct tccacttctc cact        24

<210> SEQ ID NO 42
<211> LENGTH: 28
<212> TYPE: DNA
<213> ORGANISM: Artificial Sequence
<220> FEATURE:
<223> OTHER INFORMATION: Synthetic

<400> SEQUENCE: 42
tggaggcata gaaaagctga gaaataag        28

<210> SEQ ID NO 43
<211> LENGTH: 26
<212> TYPE: DNA
<213> ORGANISM: Artificial Sequence
<220> FEATURE:
<223> OTHER INFORMATION: Synthetic

<400> SEQUENCE: 43
ttggtgctag aagaactggg agaaac        26

<210> SEQ ID NO 44
<211> LENGTH: 28
<212> TYPE: DNA
<213> ORGANISM: Artificial Sequence
<220> FEATURE:
<223> OTHER INFORMATION: Synthetic

<400> SEQUENCE: 44
gaaagtcagg ggcacatata gattagag        28

<210> SEQ ID NO 45
<211> LENGTH: 24
<212> TYPE: DNA
<213> ORGANISM: Artificial Sequence
<220> FEATURE:
<223> OTHER INFORMATION: Synthetic

<400> SEQUENCE: 45
gccttcccca tacagtttct cctt                                         24

<210> SEQ ID NO 46
<211> LENGTH: 28
<212> TYPE: DNA
<213> ORGANISM: Artificial Sequence
<220> FEATURE:
<223> OTHER INFORMATION: Synthetic

<400> SEQUENCE: 46
aagttcgtta agcccaggat cgtaggta                                     28

<210> SEQ ID NO 47
<211> LENGTH: 25
<212> TYPE: DNA
<213> ORGANISM: Artificial Sequence
<220> FEATURE:
<223> OTHER INFORMATION: Synthetic

<400> SEQUENCE: 47
atatgaagcc agcagccagg tagca                                        25

<210> SEQ ID NO 48
<211> LENGTH: 28
<212> TYPE: DNA
<213> ORGANISM: Artificial Sequence
<220> FEATURE:
<223> OTHER INFORMATION: Synthetic

<400> SEQUENCE: 48
ttagataaac tgaaagccga acctgaac                                     28

<210> SEQ ID NO 49
<211> LENGTH: 25
<212> TYPE: DNA
<213> ORGANISM: Artificial Sequence
<220> FEATURE:
<223> OTHER INFORMATION: Synthetic

<400> SEQUENCE: 49
caaactggca agcaatgtga actgt                                        25

<210> SEQ ID NO 50
<211> LENGTH: 28
<212> TYPE: DNA
<213> ORGANISM: Artificial Sequence
<220> FEATURE:
<223> OTHER INFORMATION: Synthetic

<400> SEQUENCE: 50
tcaccgacaa aacccataga gaaagagt                                     28

<210> SEQ ID NO 51
<211> LENGTH: 27
<212> TYPE: DNA
<213> ORGANISM: Artificial Sequence
<220> FEATURE:
<223> OTHER INFORMATION: Synthetic

<400> SEQUENCE: 51
ttaaatggtg aggcaatgag gaaagtg                                         27

<210> SEQ ID NO 52
<211> LENGTH: 29
<212> TYPE: DNA
<213> ORGANISM: Artificial Sequence
<220> FEATURE:
<223> OTHER INFORMATION: Synthetic

<400> SEQUENCE: 52
ttgctcattc tctttctccc ctacactaa                                       29

<210> SEQ ID NO 53
<211> LENGTH: 21
<212> TYPE: DNA
<213> ORGANISM: Artificial Sequence
<220> FEATURE:
<223> OTHER INFORMATION: Synthetic

<400> SEQUENCE: 53
tccccaccac caaccatcct c                                               21

<210> SEQ ID NO 54
<211> LENGTH: 26
<212> TYPE: DNA
<213> ORGANISM: Artificial Sequence
<220> FEATURE:
<223> OTHER INFORMATION: Synthetic

<400> SEQUENCE: 54
ctgggggaaa agcaagtagg aaagta                                          26

<210> SEQ ID NO 55
<211> LENGTH: 27
<212> TYPE: DNA
<213> ORGANISM: Artificial Sequence
<220> FEATURE:
<223> OTHER INFORMATION: Synthetic

<400> SEQUENCE: 55
acaagagtta gtcacggcaa aggagtt                                         27

<210> SEQ ID NO 56
<211> LENGTH: 22
<212> TYPE: DNA
<213> ORGANISM: Artificial Sequence
<220> FEATURE:
<223> OTHER INFORMATION: Synthetic

<400> SEQUENCE: 56
gccctttgcc catgagaact aa                                              22

<210> SEQ ID NO 57
<211> LENGTH: 26
<212> TYPE: DNA
<213> ORGANISM: Artificial Sequence
<220> FEATURE:
<223> OTHER INFORMATION: Synthetic

<400> SEQUENCE: 57
tcccagaaga gatgatatga ggtgtc                                          26

```
<210> SEQ ID NO 58
<211> LENGTH: 24
<212> TYPE: DNA
<213> ORGANISM: Artificial Sequence
<220> FEATURE:
<223> OTHER INFORMATION: Synthetic

<400> SEQUENCE: 58
tcagtcccat ctccccctaa acca                                              24

<210> SEQ ID NO 59
<211> LENGTH: 24
<212> TYPE: DNA
<213> ORGANISM: Artificial Sequence
<220> FEATURE:
<223> OTHER INFORMATION: Synthetic

<400> SEQUENCE: 59
caccattctc acccgaccac attg                                              24

<210> SEQ ID NO 60
<211> LENGTH: 30
<212> TYPE: DNA
<213> ORGANISM: Artificial Sequence
<220> FEATURE:
<223> OTHER INFORMATION: Synthetic

<400> SEQUENCE: 60
tgtaaactgc aatgaaaaga aagaaaaag                                         30

<210> SEQ ID NO 61
<211> LENGTH: 30
<212> TYPE: DNA
<213> ORGANISM: Artificial Sequence
<220> FEATURE:
<223> OTHER INFORMATION: Synthetic

<400> SEQUENCE: 61
caagagatgg gagaggaaga atgaataata                                        30

<210> SEQ ID NO 62
<211> LENGTH: 28
<212> TYPE: DNA
<213> ORGANISM: Artificial Sequence
<220> FEATURE:
<223> OTHER INFORMATION: Synthetic

<400> SEQUENCE: 62
ctatctagtc ccttacgctt tccctgtg                                          28

<210> SEQ ID NO 63
<211> LENGTH: 23
<212> TYPE: DNA
<213> ORGANISM: Artificial Sequence
<220> FEATURE:
<223> OTHER INFORMATION: Synthetic

<400> SEQUENCE: 63
cattagcatt tggcctttgg tca                                               23

<210> SEQ ID NO 64
<211> LENGTH: 25
<212> TYPE: DNA
<213> ORGANISM: Artificial Sequence
<220> FEATURE:
<223> OTHER INFORMATION: Synthetic
```

<400> SEQUENCE: 64
tgcctcccca taagtcacca atctc                                          25

<210> SEQ ID NO 65
<211> LENGTH: 30
<212> TYPE: DNA
<213> ORGANISM: Artificial Sequence
<220> FEATURE:
<223> OTHER INFORMATION: Synthetic

<400> SEQUENCE: 65
cctgtattct aaccctggac ttctcatcaa                                     30

<210> SEQ ID NO 66
<211> LENGTH: 28
<212> TYPE: DNA
<213> ORGANISM: Artificial Sequence
<220> FEATURE:
<223> OTHER INFORMATION: Synthetic

<400> SEQUENCE: 66
cttgtttatt ggcctagtcc tttgtgct                                       28

<210> SEQ ID NO 67
<211> LENGTH: 26
<212> TYPE: DNA
<213> ORGANISM: Artificial Sequence
<220> FEATURE:
<223> OTHER INFORMATION: Synthetic

<400> SEQUENCE: 67
gctttgtggg tagtcctgtc tgagtg                                         26

<210> SEQ ID NO 68
<211> LENGTH: 20
<212> TYPE: DNA
<213> ORGANISM: Artificial Sequence
<220> FEATURE:
<223> OTHER INFORMATION: Synthetic

<400> SEQUENCE: 68
ggcccatccc ggtttgctaa                                                20

<210> SEQ ID NO 69
<211> LENGTH: 27
<212> TYPE: DNA
<213> ORGANISM: Artificial Sequence
<220> FEATURE:
<223> OTHER INFORMATION: Synthetic

<400> SEQUENCE: 69
gtttccccac cacttccttt ctatgtc                                        27

<210> SEQ ID NO 70
<211> LENGTH: 25
<212> TYPE: DNA
<213> ORGANISM: Artificial Sequence
<220> FEATURE:
<223> OTHER INFORMATION: Synthetic

<400> SEQUENCE: 70
gcacaagaca tacacgcaga tacac                                          25

<210> SEQ ID NO 71
<211> LENGTH: 26
<212> TYPE: DNA
<213> ORGANISM: Artificial Sequence
<220> FEATURE:
<223> OTHER INFORMATION: Synthetic

<400> SEQUENCE: 71
aacgctggac tatggaactt tacctg                                    26

<210> SEQ ID NO 72
<211> LENGTH: 29
<212> TYPE: DNA
<213> ORGANISM: Artificial Sequence
<220> FEATURE:
<223> OTHER INFORMATION: Synthetic

<400> SEQUENCE: 72
tcctctcatt cattttgcat tcgtgttag                                 29

<210> SEQ ID NO 73
<211> LENGTH: 27
<212> TYPE: DNA
<213> ORGANISM: Artificial Sequence
<220> FEATURE:
<223> OTHER INFORMATION: Synthetic

<400> SEQUENCE: 73
ggctttgagg gattactggg ttgttct                                   27

<210> SEQ ID NO 74
<211> LENGTH: 21
<212> TYPE: DNA
<213> ORGANISM: Artificial Sequence
<220> FEATURE:
<223> OTHER INFORMATION: Synthetic

<400> SEQUENCE: 74
gcagggcaaa gaagcagtag g                                         21

<210> SEQ ID NO 75
<211> LENGTH: 26
<212> TYPE: DNA
<213> ORGANISM: Artificial Sequence
<220> FEATURE:
<223> OTHER INFORMATION: Synthetic

<400> SEQUENCE: 75
ggatcccaat ttagtttcaa gttacg                                    26

<210> SEQ ID NO 76
<211> LENGTH: 26
<212> TYPE: DNA
<213> ORGANISM: Artificial Sequence
<220> FEATURE:
<223> OTHER INFORMATION: Synthetic

<400> SEQUENCE: 76
atgtgctggc tagattggac tgaaaa                                    26

<210> SEQ ID NO 77
<211> LENGTH: 29
<212> TYPE: DNA
<213> ORGANISM: Artificial Sequence
<220> FEATURE:
<223> OTHER INFORMATION: Synthetic

<400> SEQUENCE: 77
caataaagct ggaggggtga taaataaat        29

<210> SEQ ID NO 78
<211> LENGTH: 25
<212> TYPE: DNA
<213> ORGANISM: Artificial Sequence
<220> FEATURE:
<223> OTHER INFORMATION: Synthetic

<400> SEQUENCE: 78
ttagaaggag acaatcttat tccag        25

<210> SEQ ID NO 79
<211> LENGTH: 24
<212> TYPE: DNA
<213> ORGANISM: Artificial Sequence
<220> FEATURE:
<223> OTHER INFORMATION: Synthetic

<400> SEQUENCE: 79
ctcttaaaga gatgaagcag ggag        24

<210> SEQ ID NO 80
<211> LENGTH: 24
<212> TYPE: DNA
<213> ORGANISM: Artificial Sequence
<220> FEATURE:
<223> OTHER INFORMATION: Synthetic

<400> SEQUENCE: 80
ttggctagat acagggtgaa tatt        24

<210> SEQ ID NO 81
<211> LENGTH: 24
<212> TYPE: DNA
<213> ORGANISM: Artificial Sequence
<220> FEATURE:
<223> OTHER INFORMATION: Synthetic

<400> SEQUENCE: 81
tgaattcatg tgtgtagctg agcc        24

<210> SEQ ID NO 82
<211> LENGTH: 24
<212> TYPE: DNA
<213> ORGANISM: Artificial Sequence
<220> FEATURE:
<223> OTHER INFORMATION: Synthetic

<400> SEQUENCE: 82
tgacagcggg aataaagtac atgc        24

<210> SEQ ID NO 83
<211> LENGTH: 24
<212> TYPE: DNA
<213> ORGANISM: Artificial Sequence
<220> FEATURE:
<223> OTHER INFORMATION: Synthetic

<400> SEQUENCE: 83
gttgggaggt ttacttgcca atta        24

<210> SEQ ID NO 84
<211> LENGTH: 26
<212> TYPE: DNA
<213> ORGANISM: Artificial Sequence
<220> FEATURE:
<223> OTHER INFORMATION: Synthetic

<400> SEQUENCE: 84
acattttgct aacccctctt ctatct					26

<210> SEQ ID NO 85
<211> LENGTH: 25
<212> TYPE: DNA
<213> ORGANISM: Artificial Sequence
<220> FEATURE:
<223> OTHER INFORMATION: Synthetic

<400> SEQUENCE: 85
tcaacctcaa aataaatgg catct					25

<210> SEQ ID NO 86
<211> LENGTH: 19
<212> TYPE: DNA
<213> ORGANISM: Artificial Sequence
<220> FEATURE:
<223> OTHER INFORMATION: Synthetic

<400> SEQUENCE: 86
gcatggcccc cgaggagat					19

<210> SEQ ID NO 87
<211> LENGTH: 23
<212> TYPE: DNA
<213> ORGANISM: Artificial Sequence
<220> FEATURE:
<223> OTHER INFORMATION: Synthetic

<400> SEQUENCE: 87
cttggcccat gaaaaggact gtt					23

<210> SEQ ID NO 88
<211> LENGTH: 23
<212> TYPE: DNA
<213> ORGANISM: Artificial Sequence
<220> FEATURE:
<223> OTHER INFORMATION: Synthetic

<400> SEQUENCE: 88
aggtacggga ccctgttcac gat					23

<210> SEQ ID NO 89
<211> LENGTH: 26
<212> TYPE: DNA
<213> ORGANISM: Artificial Sequence
<220> FEATURE:
<223> OTHER INFORMATION: Synthetic

<400> SEQUENCE: 89
ctaccagcat gctaaagcga ttgtct					26

<210> SEQ ID NO 90
<211> LENGTH: 24
<212> TYPE: DNA
<213> ORGANISM: Artificial Sequence
<220> FEATURE:
<223> OTHER INFORMATION: Synthetic

<400> SEQUENCE: 90
cgagtccaag cgggagacag aata                                            24

<210> SEQ ID NO 91
<211> LENGTH: 24
<212> TYPE: DNA
<213> ORGANISM: Artificial Sequence
<220> FEATURE:
<223> OTHER INFORMATION: Synthetic

<400> SEQUENCE: 91
tacacccctg ggactcagca catt                                            24

<210> SEQ ID NO 92
<211> LENGTH: 26
<212> TYPE: DNA
<213> ORGANISM: Artificial Sequence
<220> FEATURE:
<223> OTHER INFORMATION: Synthetic

<400> SEQUENCE: 92
ttcattttgg ccatctcttc cttcag                                          26

<210> SEQ ID NO 93
<211> LENGTH: 26
<212> TYPE: DNA
<213> ORGANISM: Artificial Sequence
<220> FEATURE:
<223> OTHER INFORMATION: Synthetic

<400> SEQUENCE: 93
tatccagctc gtacctcatt tcctct                                          26

<210> SEQ ID NO 94
<211> LENGTH: 20
<212> TYPE: DNA
<213> ORGANISM: Artificial Sequence
<220> FEATURE:
<223> OTHER INFORMATION: Synthetic

<400> SEQUENCE: 94
gcccaccagc tccaacacag                                                 20

<210> SEQ ID NO 95
<211> LENGTH: 24
<212> TYPE: DNA
<213> ORGANISM: Artificial Sequence
<220> FEATURE:
<223> OTHER INFORMATION: Synthetic

<400> SEQUENCE: 95
gaagggtcaa gcaggaggtc atag                                            24

<210> SEQ ID NO 96
<211> LENGTH: 26
<212> TYPE: DNA
<213> ORGANISM: Artificial Sequence
<220> FEATURE:
<223> OTHER INFORMATION: Synthetic

<400> SEQUENCE: 96
ccctgtggat gactgagtac ctgaac                                          26

```
<210> SEQ ID NO 97
<211> LENGTH: 21
<212> TYPE: DNA
<213> ORGANISM: Artificial Sequence
<220> FEATURE:
<223> OTHER INFORMATION: Synthetic

<400> SEQUENCE: 97
ggcatcccag cctccgttat c                                               21

<210> SEQ ID NO 98
<211> LENGTH: 24
<212> TYPE: DNA
<213> ORGANISM: Artificial Sequence
<220> FEATURE:
<223> OTHER INFORMATION: Synthetic

<400> SEQUENCE: 98
aattttgtgc tgcccgatga tgac                                            24

<210> SEQ ID NO 99
<211> LENGTH: 23
<212> TYPE: DNA
<213> ORGANISM: Artificial Sequence
<220> FEATURE:
<223> OTHER INFORMATION: Synthetic

<400> SEQUENCE: 99
ggaacagaag gccgggaggt agt                                             23

<210> SEQ ID NO 100
<211> LENGTH: 22
<212> TYPE: DNA
<213> ORGANISM: Artificial Sequence
<220> FEATURE:
<223> OTHER INFORMATION: Synthetic

<400> SEQUENCE: 100
gaaggccaag tggtccgtgt ga                                              22

<210> SEQ ID NO 101
<211> LENGTH: 26
<212> TYPE: DNA
<213> ORGANISM: Artificial Sequence
<220> FEATURE:
<223> OTHER INFORMATION: Synthetic

<400> SEQUENCE: 101
cagctgttgt actccttgcc attgaa                                          26

<210> SEQ ID NO 102
<211> LENGTH: 20
<212> TYPE: DNA
<213> ORGANISM: Artificial Sequence
<220> FEATURE:
<223> OTHER INFORMATION: Synthetic

<400> SEQUENCE: 102
gcctatgccc cctgagagtg                                                 20

<210> SEQ ID NO 103
<211> LENGTH: 26
<212> TYPE: DNA
<213> ORGANISM: Artificial Sequence
<220> FEATURE:
<223> OTHER INFORMATION: Synthetic
```

<400> SEQUENCE: 103
gcttgagttg gcctagtttg ttgttc                                        26

<210> SEQ ID NO 104
<211> LENGTH: 21
<212> TYPE: DNA
<213> ORGANISM: Artificial Sequence
<220> FEATURE:
<223> OTHER INFORMATION: Synthetic

<400> SEQUENCE: 104
tgcccggacc aaggatacag t                                             21

<210> SEQ ID NO 105
<211> LENGTH: 19
<212> TYPE: DNA
<213> ORGANISM: Artificial Sequence
<220> FEATURE:
<223> OTHER INFORMATION: Synthetic

<400> SEQUENCE: 105
agcgcgtggc cgaactcat                                                19

<210> SEQ ID NO 106
<211> LENGTH: 26
<212> TYPE: DNA
<213> ORGANISM: Artificial Sequence
<220> FEATURE:
<223> OTHER INFORMATION: Synthetic

<400> SEQUENCE: 106
tacggctctg aagtcaccac caaaat                                        26

<210> SEQ ID NO 107
<211> LENGTH: 23
<212> TYPE: DNA
<213> ORGANISM: Artificial Sequence
<220> FEATURE:
<223> OTHER INFORMATION: Synthetic

<400> SEQUENCE: 107
ccccagctca caattccagt caa                                           23

<210> SEQ ID NO 108
<211> LENGTH: 268
<212> TYPE: DNA
<213> ORGANISM: Homo sapiens

<400> SEQUENCE: 108
aaatgttatt atttttagtg ttactatatt tagtcccgtg gaaacacatt ttgctaaccc    60
ctcttctatc tgagacaaca cagctctctg tgttcctcaa atcagaagaa atgaaattat   120
tgagcataaa tataaactct aattttggcc tctatttcat aatgtaaact gtactccata   180
aaacacaatc tgtatgttaa agatgccatt tatttttgag gttgaaaaaa caaaaagact   240
ttagacccac atataaaagg tactctttt                                    268

MIPOL1-ETV1 GENE REARRANGEMENTS

This application is a continuation of U.S. patent application Ser. No. 15/084,721, filed Mar. 30, 2016, issued as U.S. Pat. No. 9,719,143, which is a continuation of U.S. patent application Ser. No. 12/667,819, filed Oct. 18, 2010, issued as U.S. Pat. No. 9,303,291, which is a national phase application under 35 U.S.C. § 371 of International Application No. PCT/US2008/069201, filed Jul. 3, 2008, which claims priority to U.S. Provisional Application 60/958,629, filed Jul. 6, 2007, each of which are herein incorporated by reference in their entireties.

This invention was made with government support under CA069568 and CA111275 awarded by the National Institutes of Health. The government has certain rights in the invention.

FIELD OF THE INVENTION

This invention relates to compositions and methods for cancer diagnosis, research and therapy, including but not limited to, cancer markers. In particular, this invention relates to recurrent MIPOL1-ETV1 genetic rearrangements that are useful as diagnostic markers and clinical targets for prostate cancer.

BACKGROUND OF THE INVENTION

Cancer research may identify altered genes that are causally implicated in oncogenesis. Several types of somatic mutations that result in altered activity of an oncogene or tumor suppressor gene have been identified, including base substitutions, insertions, deletions, translocations, and chromosomal gains and losses. Compelling evidence exists for a causal role for some chromosomal rearrangements in cancer (Rowley, *Nat Rev Cancer* 1: 245 (2001)). Recurrent chromosomal aberrations have been primarily characteristic of leukemias, lymphomas, and sarcomas. Less than 1% of the known, disease-specific chromosomal rearrangements are associated with epithelial tumors (carcinomas), although those cancers are much more common and contribute to a relatively large fraction of the morbidity and mortality associated with human cancer (Mitelman, *Mutat Res* 462: 247 (2000)). While hematological malignancies are often characterized by disease-specific chromosomal rearrangements, most solid tumors have a plethora of non-specific chromosomal aberrations. Karyotypic complexity of solid tumors is thought to result from secondary alterations acquired through cancer evolution or progression.

Cancer-related chromosomal rearrangements may result from two primary mechanisms. In one, promoter/enhancer elements of one gene are rearranged adjacent to a proto-oncogene, thus causing altered expression of an oncogenic protein. This type of translocation is exemplified by the apposition of immunoglobulin (IG) and T-cell receptor (TCR) genes to the MYC oncogene, leading to oncogene activation in B- and T-cell malignancies, respectively (Rabbitts, *Nature* 372: 143 (1994)). In the other mechanism, rearrangement results in the fusion of two genes, which produces a fusion protein that may have a new function or altered activity. This type of translocation is exemplified by the BCR-ABL gene fusion in chronic myelogenous leukemia (CML) (Rowley, *Nature* 243: 290 (1973); de Klein et al., *Nature* 300: 765 (1982)), which led to the rational development of imatinib mesylate that successfully targets the BCR-ABL kinase (Deininger et al., *Blood* 105: 2640 (2005)).

Recurrent MIPOL1-ETV1 genetic rearrangements are described herein, which are useful for diagnosis and therapeutic applications related to human epithelial tumors.

SUMMARY OF THE INVENTION

A method is disclosed for diagnosing prostate cancer comprising detecting the presence or absence in a biological sample of a MIPOL1-ETV1 genetic rearrangement, wherein the presence in the sample of the genetic rearrangement is indicative of prostate cancer in the individual from whom the sample was obtained. In some embodiments, the sample is tissue, blood, plasma, serum, urine, semen, prostatic secretions or prostate cells. In some embodiments, the detecting step comprises detecting chromosomal rearrangements of genomic DNA encoding MIPOL1 and ETV1. The detecting step may use a nucleic acid sequencing technique or a nucleic acid hybridization technique, such as in situ hybridization (ISH), hybridization to one or more moieties in a microarray, or Southern blot analysis. In some embodiments, the detecting step further includes nucleic acid amplification, which may use known methods that include, but are not limited to, polymerase chain reaction (PCR), reverse transcription polymerase chain reaction (RT-PCR), transcription-mediated amplification (TMA), ligase chain reaction (LCR), strand displacement amplification (SDA), and nucleic acid sequence based amplification (NASBA). In some embodiments, the detecting step detects mRNA associated with MIPOL1-ETV1 genetic rearrangements or protein expression resulting from MIPOL1-ETV1 genetic rearrangements. Such detection may include analysis of RNA and/or protein expression levels, or determination of sequence characteristics.

Compositions are disclosed for diagnosing prostate cancer comprising a reagent that directly or indirectly detects a junction between ETV1 genetic material and MIPOL1 genetic material associated with a MIPOL1-ETV1 genetic rearrangement. Embodiments of such reagents include: a probe comprising a sequence that hybridizes to the junction between ETV1 genetic material and MIPOL1 genetic material associated with a MIPOL1-ETV1 genetic rearrangement, which may be the junction at which a ETV1 gene is inserted into a MIPOL1 gene; a combination of first and second probes, in which a first probe comprises a sequence that hybridizes to the ETV1 gene and a second probe comprises a sequence that hybridizes to the MIPOL1 gene; and at least one first amplification oligonucleotide that comprises a sequence that hybridizes specifically to a ETV1 gene and at least one second amplification oligonucleotide that comprises a sequence that hybridizes specifically to an MIPOL1 gene.

In some embodiments, the composition of amplification oligonucleotides may also include a probe that hybridizes specifically to a sequence located between the sequences hybridized by the first amplification oligonucleotide and the second oligonucleotide, which probe may hybridize specifically to a sequence in the ETV1 gene or in the MIPOL1 gene. All probes may be linked directly or indirectly to a label that provides a detectable signal.

DESCRIPTION OF THE FIGURES

FIG. 1, a is a schematic illustration of the ETV1 locus on chromosome 7 and FIG. 1, b is a schematic illustration of 14q13.3-14q21.1 on chromosome 14 and BACs used as probes for fluorescence in situ hybridization (FISH) to detect genetic rearrangements. FIG. 1, c and -d illustrate FISH performed by using BACs indicated with the corresponding fluorescent label on metaphase spreads from LNCaP (tetraploid) cells (FIG. 1, c) and d) MDA-PCa 2B (diploid) cells (FIG. 1, d) to detect rearrangements at the ETV1 locus (left panel) and 14q13.3-14q21.1 (right panel). FIG. 1, e-g, illustrate structure of ETV1 and 14q13.3-14q21.1 in: normal cells (FIG. 1, e), LNCaP cells (FIG. 1, f), and MDA-PCa 2B cells (FIG. 1, g), as determined by FISH for all.

FIG. 2, a-b, are schematic illustrations of BACs used from chromosomes 7p and 14q32, respectively (previously FISH mapped to chromosome 14). FIG. 2, c. illustrates FISH using BACs labeled with the indicated fluorescent label showed two copies of ETV1 on chromosome 7 and two copies on chromosome 14, as identified by RP11-483K13.

FIG. 3, a illustrates FISH used to narrow the breakpoint region between BACs 12 and 2, as shown in green in FIG. 3, b, as BACs 1 and 12 co-localized to chromosome 7 and chromosome 14. FIG. 3, b illustrates a series of 22 probes (A-Q) for Southern blotting that were designed to span the implicated region. FIG. 3, c illustrates a restriction map of the Probe A region, with restriction sites for PstI and EcoRI indicated, which was the only probe to show rearranged bands on Southern blotting. FIG. 3, d illustrates Southern blotting with Probe A which showed additional bands in LNCaP genomic DNA digested with EcoRI and PstI, but not in VCaP, normal male ("Nor male") genomic DNA or human placental DNA.

FIG. 4, a illustrates, a series of divergent PCR primers designed for inverse PCR (A3-B3) which were based on the detection of rearrangements in LNCaP genomic DNA digested with EcoRI and PstI using Probe A. FIG. 4, b illustrates results obtained from PCR amplification using nested PCRs subsequently with A1 and B1 (1), A2 and B2 (2), and A3 and B3 (3) on PstI digested low (L) and high (H) passage LNCaP genomic DNA. FIG. 4, c illustrates the sequence of the nested PCR product of A3 and B3 (shown in FIG. 4, b), in which the DNA breakpoint is shown in red, and the partner sequence was intronic DNA from the MIPOL1 locus at 14q13.3-14q21.1. FIG. 4, d illustrates the breakpoint location shown by an asterisk. FIG. 4, e illustrates primers designed (as shown in FIG. 4, c) to confirm the fusion by PCR on undigested DNA, in which PCR confirmed the fusion in both low and high passage LNCaP cells, but not VcaP, normal male ("Nor male") genomic DNA or human placental DNA.

FIG. 6, a illustrates the tissue specificity of the 4 contiguous genes in the 14q13.3-14q21.1 region which was interrogated in the expo dataset (using Oncomine) and expression (in normalized expression units) is shown for 28 distinct tumor types and prostate cancer. FIG. 6, b and -c illustrate androgen regulation of the contiguous 14q13.3-14q21.1 genes (FIG. 6, b) and ETV1 (FIG. 6, c), as determined by qPCR in LNCaP cells with (+) or without (−) stimulation by the synthetic androgen R1881. Ratios of target gene to GAPDH (mean (n=4)+S.E.) are shown. FIG. 6, d illustrates that LNCaP and its androgen insensitive derivative, C4-2B, were profiled using a microarray (Agilent Whole Genome Microarrays), in which the top ten most differentially expressed features (LNCaP/C4-2B) are shown. FIG. 6, e-g illustrate qPCR results that show decreased expression of androgen regulated genes in C4-2B compared to LNCaP, for markers ETV1 (FIG. 6, e) and PSA (FIG. 6, f), and the 4 contiguous transcripts at 14q13.3-14q21.1 (FIG. 6, g).

FIG. 8, a is a schematic of the ETV1 locus on chromosome 7 and BACs used as probes for fluorescence in situ hybridization (FISH) to detect rearrangements at the ETV1 locus, in which the breakpoint locations identified in LNCaP are indicated by an asterisk. FIG. 8, b illustrates results obtained by FISH performed by using BACs indicated with the corresponding fluorescent label on C4-2B (tetraploid). FIG. 8, c illustrates results obtained by PCR using primers from chromosomes 7 and 14 which confirmed the rearrangement of the ETV1 locus in C4-2B, similarly to low and high passage LNCaP, and in which no products were obtained from other prostate cancer cell lines, human placental DNA, or normal male human DNA.

DEFINITIONS

Figure 1:
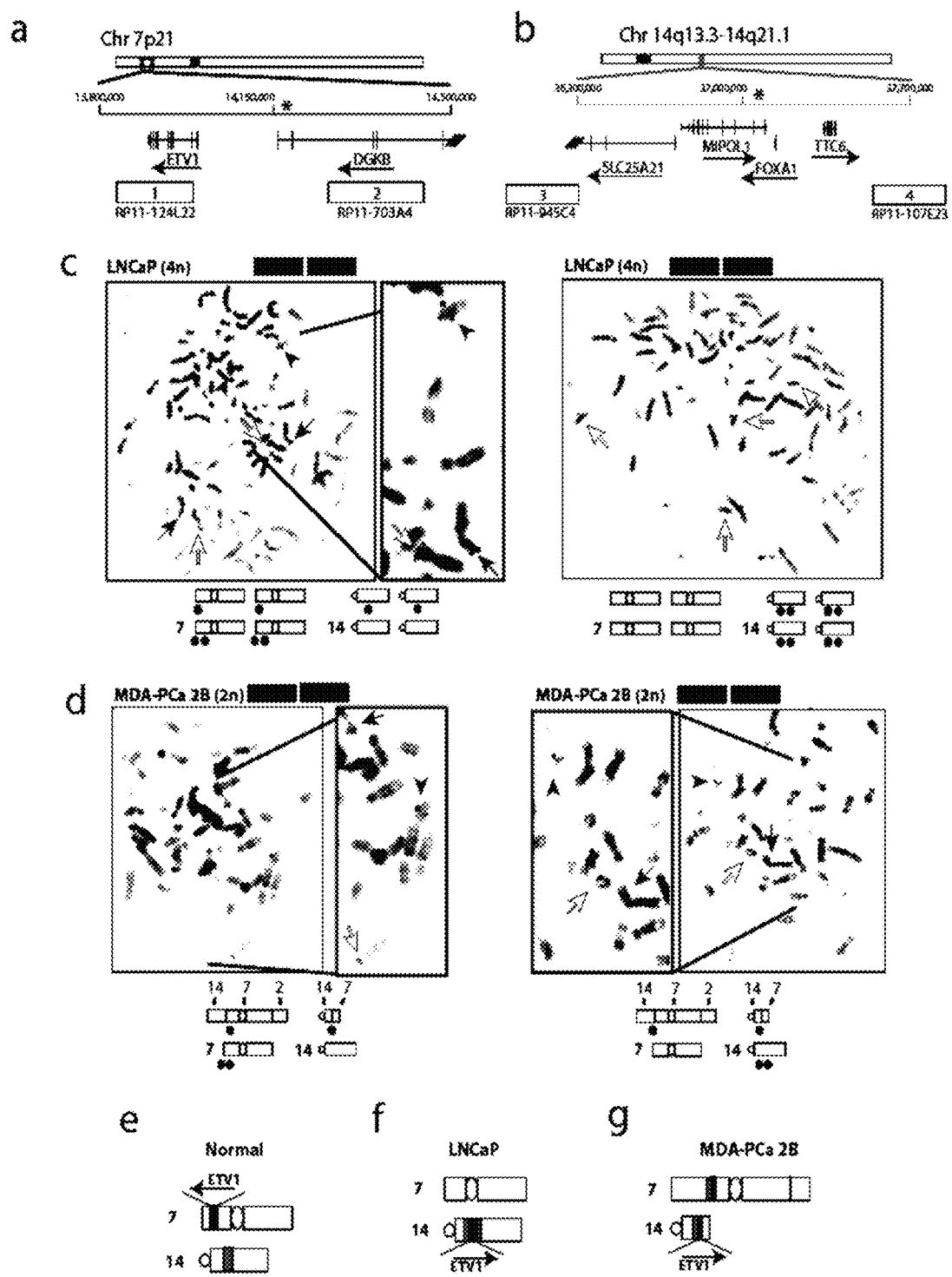
FIG. 1 illustrates the entire ETV1 locus rearranged to 14q13.3-14q21.1 in LNCaP and MDA-PCa 2B prostate cancer cells.

To facilitate an understanding of this disclosure, terms are defined below:

As used herein, "gene rearrangement" or "genetic rearrangement" refers to any altered arrangement of genomic DNA resulting from the chromosomal rearrangement of two distinct genetic regions, two different genes, or portions of two different genes. The product of a genetic rearrangement includes a fusion of genetic material that does not exist in the absence of the genetic rearrangement. That is, the genetic rearrangement results in a junction that fuses one genetic sequence to another genetic sequence to produce a junction does not exist in a wild type non-rearranged genome. Examples of genetic rearrangements include, but are not limited to, insertions of all or part of a first gene or genetic locus into a second gene or genetic locus. In some cases, an insertion may result in a new configuration of the first and second genes or genetic loci that changes regulation of expression, e.g., resulting in increased or decreased expression of a wild type protein. In other cases, an insertion may result in a gene fusion or chimeric DNA that is transcribed to make a chimeric RNA, which may be translated to make altered protein(s) compared to wild type protein(s), i.e., resulting in a new product that is different than made in a wild type configuration.

As used herein, "gene fusion" may refer to a chimeric genomic DNA, a chimeric mRNA that is transcribed from a chimeric DNA (which may be referred to as "gene fusion RNA"), or a protein translated from chimeric mRNA which is transcribed from a chimeric DNA. Such a "gene fusion protein" (or "gene fusion polypeptide") may be a truncated protein compared to wild type protein, or a chimeric protein resulting from expression of at least a portion of a first gene fused to at least a portion of a second gene. A gene fusion (or RNA transcribed from the gene fusion DNA) need not include entire genes or exons of genes.

As used herein, the term "transcriptional regulatory region" refers to the non-coding upstream regulatory sequence of a gene, also called the 5' untranslated region (5'UTR).

As used herein, the terms "detect", "detecting", or "detection" may describe either the general act of discovering or discerning or the specific observation of a detectably labeled composition.

As used herein, the term "inhibits at least one biological activity of a gene fusion" refers to any agent that decreases any activity of a gene fusion disclosed herein, its transcript(s) and/or translation products (e.g., including, but not limited to, the activities described herein), via directly contacting a gene fusion protein, contacting gene fusion mRNA or genomic DNA, causing conformational changes of gene fusion polypeptides, decreasing gene fusion protein levels, or interfering with gene fusion interactions with signaling partners, and affecting the expression of target gene fusions (i.e., transcription or translation of the resulting transcripts). Inhibitors also include molecules that indirectly regulate gene fusion biological activity by intercepting upstream signaling molecules.

As used herein, the term "siRNAs" refers to small interfering RNAs. In some embodiments, siRNAs comprise a duplex, or double-stranded region, of about 18-25 nucleotides long; often siRNAs contain from about two to four unpaired nucleotides at the 3' end of each strand. At least one strand of the duplex or double-stranded region of a siRNA is substantially homologous to, or substantially complementary to, a target RNA molecule. The strand complementary to a target RNA molecule is the "antisense strand;" the strand homologous to the target RNA molecule is the "sense strand," and is also complementary to the siRNA antisense strand. siRNAs may also contain additional sequences; non-limiting examples of such sequences include linking sequences, or loops, as well as stem and other folded structures. siRNAs appear to function as key intermediaries in triggering RNA interference in invertebrates and in vertebrates, and in triggering sequence-specific RNA degradation during posttranscriptional gene silencing in plants.

The term "RNA interference" or "RNAi" refers to the silencing or decreasing of gene expression by siRNAs. It is the process of sequence-specific, post-transcriptional gene silencing in animals and plants, initiated by siRNA that is homologous in its duplex region to the sequence of the silenced gene. The gene may be endogenous or exogenous to the organism, present integrated into a chromosome or present in a transfection vector that is not integrated into the genome. The expression of the gene is either completely or partially inhibited. RNAi may also be considered to inhibit the function of a target RNA; the function of the target RNA may be complete or partial.

As used herein, the term "stage of cancer" refers to a qualitative or quantitative assessment of the level of advancement of a cancer. Criteria used to determine the stage of a cancer include, but are not limited to, the size of the tumor and the extent of metastases (e.g., localized or distant).

As used herein, the term "gene transfer system" refers to any means of delivering a composition comprising a nucleic acid sequence to a cell or tissue. For example, gene transfer systems include, but are not limited to, vectors (e.g., retroviral, adenoviral, adeno-associated viral, and other nucleic acid-based delivery systems), microinjection of naked nucleic acid, polymer-based delivery systems (e.g., liposome-based and metallic particle-based systems), biolistic injection, and the like. As used herein, the term "viral gene transfer system" refers to gene transfer systems comprising viral elements (e.g., intact viruses, modified viruses and viral components such as nucleic acids or proteins) to facilitate delivery of the sample to a desired cell or tissue. As used herein, the term "adenovirus gene transfer system" refers to gene transfer systems comprising intact or altered viruses belonging to the family Adenoviridae.

As used herein, the term "site-specific recombination target sequences" refers to nucleic acid sequences that provide recognition sequences for recombination factors and the location where recombination takes place.

As used herein, the term "nucleic acid molecule" refers to any nucleic acid containing molecule, including but not limited to, DNA or RNA. The term encompasses sequences that include any of the known base analogs of DNA and RNA including, but not limited to, 4-acetylcytosine, 8-hydroxy-N6-methyladenosine, aziridinylcytosine, pseudoisocytosine, 5-(carboxyhydroxylmethyl) uracil, 5-fluorouracil, 5-bromouracil, 5-carboxymethylaminomethyl-2-thiouracil, 5-carboxymethylaminomethyluracil, dihydrouracil, inosine, N6-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, N6-methyladenine, 7-methylguanine, 5-methylaminomethyluracil, 5-methoxyaminomethyl-2-thiouracil, beta-D-mannosylqueosine, 5'-methoxycarbonylmethyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine, and 2,6-diaminopurine.

The term "gene" refers to a nucleic acid (e.g., DNA) sequence that comprises coding sequences necessary for the production of a polypeptide, precursor, or RNA (e.g., rRNA, tRNA). The polypeptide can be encoded by a full length coding sequence or by any portion of the coding sequence so long as the desired activity or functional properties (e.g., enzymatic activity, ligand binding, signal transduction, immunogenicity, etc.) of the full-length or fragment are retained. The term also encompasses the coding region of a structural gene and the sequences located adjacent to the coding region on both the 5' and 3' ends for a distance of about 1 kb or more on either end such that the gene corresponds to the length of the full-length mRNA. Sequences located 5' of the coding region and present on the mRNA are referred to as 5' non-translated sequences. Sequences located 3' or downstream of the coding region and present on the mRNA are referred to as 3' non-translated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene that are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

As used herein, the term "heterologous gene" refers to a gene that is not in its natural environment. For example, a heterologous gene includes a gene from one species introduced into another species. A heterologous gene also includes a gene native to an organism that has been altered in some way (e.g., mutated, added in multiple copies, linked to non-native regulatory sequences, etc). Heterologous genes are distinguished from endogenous genes in that the heterologous gene sequences are typically joined to DNA sequences that are not found naturally associated with the gene sequences in the chromosome or are associated with portions of the chromosome not found in nature (e.g., genes expressed in loci where the gene is not normally expressed).

As used herein, the term "oligonucleotide," refers to a short length of single-stranded polynucleotide chain. Oligonucleotides are typically less than 200 residues long (e.g., between 15 and 100), however, as used herein, the term is also intended to encompass longer polynucleotide chains. Oligonucleotides are often referred to by their length. For example a 24 residue oligonucleotide is referred to as a "24-mer". Oligonucleotides can form secondary and tertiary structures by self-hybridizing or by hybridizing to other polynucleotides. Such structures can include, but are not limited to, duplexes, hairpins, cruciforms, bends, and triplexes.

As used herein, the terms "complementary" or "complementarity" are used in reference to polynucleotides (i.e., a sequence of nucleotides) related by the base-pairing rules. For example, the sequence "5'-A-G-T-3'," is complementary to the sequence "3'-T-C-A-5'." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods that depend upon binding between nucleic acids.

The term "homology" refers to a degree of complementarity. There may be partial homology or complete homology (i.e., identity). A partially complementary sequence is a nucleic acid molecule that at least partially inhibits a completely complementary nucleic acid molecule from hybridizing to a target nucleic acid is "substantially homologous." The inhibition of hybridization of the completely complementary sequence to the target sequence may be examined using a hybridization assay (Southern or Northern blot, solution hybridization and the like) under conditions of low stringency. A substantially homologous sequence or probe will compete for and inhibit the binding (i.e., the hybridization) of a completely homologous nucleic acid molecule to a target under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target that is substantially non-complementary (e.g., less than about 30% identity); in the absence of non-specific binding the probe will not hybridize to the second non-complementary target.

When used in reference to a double-stranded nucleic acid sequence such as a cDNA or genomic clone, the term "substantially homologous" refers to any probe that can hybridize to either or both strands of the double-stranded nucleic acid sequence under conditions of low stringency as described above.

A gene may produce multiple RNA species that are generated by differential splicing of the primary RNA transcript. cDNAs that are splice variants of the same gene will contain regions of sequence identity or complete homology (representing the presence of the same exon or portion of the same exon on both cDNAs) and regions of complete non-identity (for example, representing the presence of exon "A" on cDNA 1 wherein cDNA 2 contains exon "B" instead). Because the two cDNAs contain regions of sequence identity they will both hybridize to a probe derived from the entire gene or portions of the gene containing sequences found on both cDNAs; the two splice variants are therefore substantially homologous to such a probe and to each other.

When used in reference to a single-stranded nucleic acid sequence, the term "substantially homologous" refers to any probe that can hybridize (i.e., it is the complement of) the single-stranded nucleic acid sequence under conditions of low stringency as described above.

As used herein, the term "hybridization" is used in reference to the pairing of complementary nucleic acids. Hybridization and the strength of hybridization (i.e., the strength of the association between the nucleic acids) is impacted by such factors as the degree of complementary between the nucleic acids, stringency of the conditions involved, the $T_m$ of the formed hybrid, and the G:C ratio within the nucleic acids. A single molecule that contains pairing of complementary nucleic acids within its structure is said to be "self-hybridized."

As used herein the term "stringency" is used in reference to the conditions of temperature, ionic strength, and the presence of other compounds such as organic solvents, under which nucleic acid hybridizations are conducted. Under "low stringency conditions" a nucleic acid sequence of interest will hybridize to its exact complement, sequences with single base mismatches, closely related sequences (e.g., sequences with 90% or greater homology), and sequences having only partial homology (e.g., sequences with 50-90% homology). Under 'medium stringency conditions," a nucleic acid sequence of interest will hybridize only to its exact complement, sequences with single base mismatches, and closely relation sequences (e.g., 90% or greater homology). Under "high stringency conditions," a nucleic acid sequence of interest will hybridize only to its exact complement, and (depending on conditions such a temperature) sequences with single base mismatches. In other words, under conditions of high stringency the temperature can be raised so as to exclude hybridization to sequences with single base mismatches.

"High stringency conditions" when used in reference to nucleic acid hybridization comprise conditions equivalent to binding or hybridization at 42° C. in a solution consisting of 5× SSPE (43.8 g/l NaCl, 6.9 g/l NaH$_2$PO$_4$ H$_2$O and 1.85 g/l EDTA, pH adjusted to 7.4 with NaOH), 0.5% SDS, 5× Denhardt's reagent and 100 µg/ml denatured salmon sperm DNA followed by washing in a solution comprising 0.1× SSPE, 1.0% SDS at 42° C. when a probe of about 500 nucleotides in length is employed.

"Medium stringency conditions" when used in reference to nucleic acid hybridization comprise conditions equivalent to binding or hybridization at 42° C. in a solution consisting of 5× SSPE (43.8 g/l NaCl, 6.9 g/l NaH$_2$PO$_4$ H$_2$O and 1.85 g/l EDTA, pH adjusted to 7.4 with NaOH), 0.5% SDS, 5× Denhardt's reagent and 100 μg/ml denatured salmon sperm DNA followed by washing in a solution comprising 1.0× SSPE, 1.0% SDS at 42° C. when a probe of about 500 nucleotides in length is employed.

"Low stringency conditions" comprise conditions equivalent to binding or hybridization at 42° C. in a solution consisting of 5× SSPE (43.8 g/l NaCl, 6.9 g/l NaH$_2$PO$_4$ H$_2$O and 1.85 g/l EDTA, pH adjusted to 7.4 with NaOH), 0.1% SDS, 5× Denhardt's reagent [50× Denhardt's contains per 500 ml: 5 g Ficoll (Type 400, Pharmacia), 5 g BSA (Fraction V; Sigma)] and 100 μg/ml denatured salmon sperm DNA followed by washing in a solution comprising 5× SSPE, 0.1% SDS at 42° C. when a probe of about 500 nucleotides in length is employed.

The art knows well that numerous equivalent conditions may be employed to comprise low stringency conditions; factors such as the length and nature (DNA, RNA, base composition) of the probe and nature of the target (DNA, RNA, base composition, present in solution or immobilized, etc.) and the concentration of the salts and other components (e.g., the presence or absence of formamide, dextran sulfate, polyethylene glycol) are considered and the hybridization solution may be varied to generate conditions of low stringency hybridization different from, but equivalent to, the above listed conditions. In addition, the art knows conditions that promote hybridization under conditions of high stringency (e.g., increasing the temperature of the hybridization and/or wash steps, the use of formamide in the hybridization solution, etc.) (see definition above for "stringency").

As used herein, the term "amplification oligonucleotide" refers to an oligonucleotide that hybridizes to a target nucleic acid, or its complement, and participates in a nucleic acid amplification reaction. An example of an amplification oligonucleotide is a "primer" that hybridizes to a template nucleic acid and contains a 3' OH end that is extended by a polymerase in an amplification process. Another example of an amplification oligonucleotide is an oligonucleotide that is not extended by a polymerase (e.g., because it has a 3' blocked end) but participates in or facilitates amplification. Amplification oligonucleotides may optionally include modified nucleotides or analogs, or additional nucleotides that participate in an amplification reaction but are not complementary to or contained in the target nucleic acid. Amplification oligonucleotides may contain a sequence that is not complementary to the target or template sequence. For example, the 5' region of a primer may include a promoter sequence that is non-complementary to the target nucleic acid (referred to as a "promoter-primer"). Those skilled in the art will understand that an amplification oligonucleotide that functions as a primer may be modified to include a 5' promoter sequence, and thus function as a promoter-primer. Similarly, a promoter-primer may be modified by removal of, or synthesis without, a promoter sequence and still function as a primer. A 3' blocked amplification oligonucleotide may provide a promoter sequence and serve as a template for polymerization (referred to as a "promoter-provider").

As used herein, the term "primer" refers to an oligonucleotide, whether occurring naturally as in a purified restriction digest or produced synthetically, that is capable of acting as a point of initiation of synthesis when placed under conditions in which synthesis of a primer extension product that is complementary to a nucleic acid strand is induced, (i.e., in the presence of nucleotides and an inducing agent such as DNA polymerase and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent. The exact lengths of the primers will depend on many factors, including temperature, source of primer and the use of the method.

As used herein, the term "probe" refers to an oligonucleotide (i.e., a sequence of nucleotides), whether occurring naturally as in a purified restriction digest or produced synthetically, recombinantly or by PCR amplification, that is capable of hybridizing to at least a portion of another oligonucleotide of interest. A probe may be single-stranded or double-stranded. Probes are useful in the detection, identification and isolation of particular gene sequences. It is contemplated that any probe used in the disclosed methods may be labeled with any "reporter molecule," so that is detectable in any detection system, including, but not limited to enzyme (e.g., ELISA, as well as enzyme-based histochemical assays), fluorescent, radioactive, and luminescent systems. The compositions and methods that use such compositions as disclosed herein are not limited to any particular detection system or label.

The term "isolated" when used in relation to a nucleic acid, as in "an isolated oligonucleotide" or "isolated polynucleotide" refers to a nucleic acid sequence that is identified and separated from at least one component or contaminant with which it is ordinarily associated in its natural source. Isolated nucleic acid is such present in a form or setting that is different from that in which it is found in nature. In contrast, non-isolated nucleic acids as nucleic acids such as DNA and RNA found in the state they exist in nature. For example, a given DNA sequence (e.g., a gene) is found on the host cell chromosome in proximity to neighboring genes; RNA sequences, such as a specific mRNA sequence encoding a specific protein, are found in the cell as a mixture with numerous other mRNAs that encode a multitude of proteins. However, isolated nucleic acid encoding a given protein includes, by way of example, such nucleic acid in cells ordinarily expressing the given protein where the nucleic acid is in a chromosomal location different from that of natural cells, or is otherwise flanked by a different nucleic acid sequence than that found in nature. The isolated nucleic acid, oligonucleotide, or polynucleotide may be present in single-stranded or double-stranded form. When an isolated nucleic acid, oligonucleotide or polynucleotide is to be used to express a protein, the oligonucleotide or polynucleotide will contain at a minimum the sense or coding strand (i.e., the oligonucleotide or polynucleotide may be single-stranded), but may contain both the sense and anti-sense strands (i.e., the oligonucleotide or polynucleotide may be double-stranded).

As used herein, the term "purified" or "to purify" refers to the removal of components (e.g., contaminants) from a sample. For example, antibodies are purified by removal of contaminating non-immunoglobulin proteins; they are also purified by the removal of immunoglobulin that does not bind to the target molecule. The removal of non-immunoglobulin proteins and/or the removal of immunoglobulins that do not bind to the target molecule results in an increase in the percent of target-reactive immunoglobulins in the sample. In another example, recombinant polypeptides are expressed in bacterial host cells and the polypeptides are purified by the removal of host cell proteins; the percent of recombinant polypeptides is thereby increased in the sample.

DETAILED DESCRIPTION OF THE INVENTION

The disclosed compositions and methods are based on the discovery of recurrent gene rearrangements in prostate cancer. These compositions and methods are useful for diagnostic applications, therapeutic methods, and evaluation of therapeutic treatments that either directly or indirectly detect or target MIPOL1-ETV1 gene rearrangements.

I. Gene Rearrangements

Recurrent gene rearrangements disclosed herein are indicative of prostate cancer. These genetic rearrangements result from chromosomal rearrangements that insert MIPOL1 genetic material into the ETV1 genetic locus. These recurrent gene rearrangements are useful diagnostic markers and clinical targets for prostate cancer.

In some embodiments, all or a portion of the ETV1 is inserted into the MIPOL1 locus (e.g., into an intron). The gene rearrangement is detectable, for example, as a chromosomal rearrangement of genomic DNA having at least a portion of an ETV1 gene inserted into a MIPOL1 locus.

II. Antibodies

The gene rearrangements disclosed herein result in proteins, which include fragments, derivatives and analogs thereof, which may be used as immunogens to produce antibodies useful for diagnostic and therapeutic applications. Such antibodies may be polyclonal or monoclonal, chimeric, humanized, single chain or Fab fragments, which may be labeled or unlabeled, all of which may be produced by using well known procedures and standard laboratory practices. See, e.g., Burns, ed., *Immunochemical Protocols*, 3$^{rd}$ ed., Humana Press (2005); Harlow and Lane, *Antibodies: A Laboratory Manual*, Cold Spring Harbor Laboratory (1988); Kozbor et al., *Immunology Today* 4: 72 (1983); Köhler and Milstein, *Nature* 256: 495 (1975).

III. Diagnostic Applications

The disclosed MIPOL1-ETV1 genetic rearrangements provide DNA, RNA and protein based diagnostic methods that detect, either directly or indirectly, the gene rearrangements or a product made specifically as a result of the genetic rearrangement. The disclosed MIPOL1-ETV1 genetic rearrangements also provide compositions useful for diagnostic purposes, such as oligonucleotide probes that specifically detect all or part of the genetic rearrangement. Such compositions may be in the form of a kit.

The disclosed diagnostic methods may be qualitative or quantitative. Quantitative methods may, e.g., discriminate between indolent and aggressive cancers via a cutoff or threshold level where expression above that level provides information on the aggressiveness of the cancer which provides useful diagnostic and/or prognostic information to a treating physician or patient. Qualitative or quantitative diagnostic methods may include amplification of a target, signal or intermediary, such as by using a universal primer that amplifies a sequence that serves as an indicator for the presence or level of the specific target associated with the MIPOL1-ETV1 genetic rearrangement.

An initial assay may confirm the presence of a gene rearrangement but not identify the specific rearrangement. A secondary assay is then performed to determine the identity of the particular rearrangement, if desired. The second assay may use a different detection technology than the initial assay.

The disclosed MIPOL1-ETV1 genetic rearrangement may be detected along with other markers in a multiplex or panel format. Markers are selected for their predictive value alone or in combination with the gene rearrangements. Exemplary prostate cancer markers include, but are not limited to: AMACR/P504S (U.S. Pat. No. 6,262,245); PCA3 (U.S. Pat. No. 7,008,765); PCGEM1 (U.S. Pat. No. 6,828,429); prostein/P501S, P503S, P504S, P509S, P510S, prostase/P703P, P710P (U.S. Publication No. 20030185830); and, those disclosed in U.S. Pat. Nos. 5,854,206 and 6,034,218, and U.S. Publication No. 20030175736, each of which is herein incorporated by reference in its entirety. Markers for other cancers, diseases, infections, and metabolic conditions are also contemplated for inclusion in a multiplex of panel format.

The diagnostic methods as disclosed herein may be modified with reference to data correlating particular gene rearrangements with the stage, aggressiveness or progression of the disease or the presence or risk of metastasis. The information provided by these diagnostic methods provide useful information to a physician who, based on that information, may choose an appropriate therapeutic treatment for a particular patient.

A. Sample

Any biological sample suspected of containing the MIPOL1-ETV1 gene rearrangements may be tested according to the disclosed methods. Such a sample may be tissue (e.g., prostate biopsy sample or tissue obtained by prostatectomy), blood, urine, semen, prostatic secretions or a fraction thereof (e.g., plasma, serum, urine supernatant, urine cell pellet or prostate cells), which may be obtained from a patient or other source of biological material, e.g., autopsy sample or forensic material. In preferred embodiments, a urine sample is collected immediately following an attentive digital rectal examination (DRE), which causes prostate cells from the prostate gland to shed into the urinary tract.

The sample may be processed to isolate or enrich the sample for the gene rearrangements or cells that contain the gene rearrangements. A variety of well techniques that use standard laboratory practices may be used for this purpose, such as, e.g., centrifugation, immunocapture, cell lysis, and nucleic acid target capture (See, e.g., EP Pat. No. 1 409 727, herein incorporated by reference in its entirety).

B. DNA and RNA Detection

The disclosed MIPOL1-ETV1 genetic rearrangements may be detected as chromosomal rearrangements of genomic DNA or as chimeric mRNA produced from a chromosomal rearrangement by using a variety of well known nucleic acid techniques that rely on standard laboratory methods, such as, e.g., nucleic acid sequencing, nucleic acid hybridization, and, nucleic acid amplification.

1. Sequencing

Illustrative non-limiting examples of nucleic acid sequencing techniques include, but are not limited to, chain terminator (Sanger) sequencing and dye terminator sequencing. Those of ordinary skill in the art will recognize that because RNA is less stable in the cell and more prone to nuclease attack experimentally RNA is usually reverse transcribed to DNA before sequencing.

Chain terminator sequencing uses sequence-specific termination of a DNA synthesis reaction using modified nucleotide substrates. Extension is initiated at a specific site on the template DNA by using a short radioactive, or other labeled, oligonucleotide primer complementary to the template at that region. The oligonucleotide primer is extended using a DNA polymerase, standard four deoxynucleotide bases, and a low concentration of one chain terminating nucleotide, most commonly a di-deoxynucleotide. This reaction is repeated in four separate tubes with each of the bases taking turns as the di-deoxynucleotide. Limited incorporation of the chain terminating nucleotide by the DNA polymerase results in a series of related DNA fragments that are terminated only at positions where that particular di-deoxynucleotide is used. For each reaction tube, the fragments are size-separated by electrophoresis in a slab polyacrylamide gel or a capillary tube filled with a viscous polymer. The sequence is determined by reading which lane produces a visualized mark from the labeled primer as you scan from the top of the gel to the bottom.

Dye terminator sequencing alternatively labels the terminators. Complete sequencing can be performed in a single reaction by labeling each of the di-deoxynucleotide chain-terminators with a separate fluorescent dye, which fluoresces at a different wavelength.

2. Hybridization

Illustrative non-limiting examples of nucleic acid hybridization techniques include, but are not limited to, in situ hybridization (ISH), microarray, and Southern or Northern blot.

In situ hybridization (ISH) is a type of hybridization that uses a labeled complementary DNA or RNA strand as a probe to localize a specific DNA or RNA sequence in a portion or section of tissue (in situ), or, if the tissue is small enough, the entire tissue (whole mount ISH). DNA ISH can be used to determine the structure of chromosomes. RNA ISH is used to measure and localize mRNAs and other transcripts within tissue sections or whole mounts. Sample cells and tissues are usually treated to fix the target transcripts in place and to increase access of the probe. The probe hybridizes to the target sequence at elevated temperature, and then the excess probe is washed away. The probe that was labeled with either radio-, fluorescent- or antigen-labeled bases is localized and quantitated in the tissue using either autoradiography, fluorescence microscopy or immunohistochemistry, respectively. ISH can also use two or more probes, labeled with radioactivity or the other non-radioactive labels, to simultaneously detect two or more transcripts.

2.1 FISH

In some embodiments, gene rearrangements are detected using fluorescence in situ hybridization (FISH). The preferred FISH assays use bacterial artificial chromosomes (BACs), which have been used extensively in the human genome sequencing project (see *Nature* 409: 953-958 (2001)) and clones containing specific BACs are widely available or can be made by using standard laboratory practices. Each BAC clone from the human genome has been given a reference name that unambiguously identifies it. These names can be used to find a corresponding GenBank sequence and to order copies of the clone from a distributor.

Specific BAC clones that can be used in FISH protocols to detect MIPOL1-ETV1 genetic rearrangements are probes specific for RP11-124L22 and RP11-703A4. These probes, or other suitable probes, usually are labeled with appropriate fluorescent or other markers and then used in hybridizations. The Examples section provided herein sets forth one particular protocol that is effective for measuring rearrangements but one of skill in the art will recognize that many variations of this assay can be used equally well. Specific protocols are well known in the art and can be readily adapted for detecting MIPOL1-ETV1 rearrangements. Guidance regarding such methodology is provided in many references including: *In situ Hybridization: Medical Applications* (eds. G. R. Coulton and J. de Belleroche), Kluwer Academic Publishers, Boston (1992); *In situ Hybridization: In Neurobiology; Advances in Methodology* (eds. J. H. Eberwine, K. L. Valentino, and J. D. Barchas), Oxford University Press Inc., England (1994); *In situ Hybridization: A Practical Approach* (ed. D. G. Wilkinson), Oxford University Press Inc., England (1992)); Kuo, et al., *Am. J. Hum. Genet.* 49:112-119 (1991); Klinger, et al., *Am. J. Hum. Genet.* 51:55-65 (1992); and Ward, et al., *Am. J. Hum. Genet.* 52:854-865 (1993)). Patents providing guidance on such methodology include U.S. Pat. Nos. 5,225,326; 5,545,524; 6,121,489 and 6,573,043, and commercially available kits also provide protocols for performing FISH (e.g., from Oncor, Inc., Gaithersburg, Md.). All of these references are hereby incorporated by reference in their entirety and may be used along with similar references in the art and with the information provided in the Examples section herein to establish procedural steps convenient for a particular laboratory.

2.2 Microarrays

Different kinds of biological assays are called microarrays including, but not limited to: DNA microarrays (e.g., cDNA microarrays and oligonucleotide microarrays); protein microarrays; tissue microarrays; transfection or cell microarrays; chemical compound microarrays; and, antibody microarrays. A DNA microarray, commonly known as gene chip, DNA chip, or biochip, is a collection of microscopic DNA spots attached to a solid surface (e.g., glass, plastic or silicon chip) forming an array for the purpose of expression profiling or monitoring expression levels for thousands of genes simultaneously. The affixed DNA segments are known as probes, thousands of which can be used in a single DNA microarray. Microarrays can be used to identify disease genes by comparing gene expression in disease and normal cells. Microarrays can be fabricated using a variety of technologies, including but not limiting: printing with fine-pointed pins onto glass slides; photolithography using pre-made masks; photolithography using dynamic micromirror devices; ink-jet printing; or, electrochemistry on microelectrode arrays.

Southern and Northern blotting is used to detect specific DNA or RNA sequences, respectively. DNA or RNA extracted from a sample is fragmented, electrophoretically separated on a matrix gel, and transferred to a membrane filter. The filter bound DNA or RNA is subject to hybridization with a labeled probe complementary to the sequence of interest. Hybridized probe bound to the filter is detected. A variant of the procedure is the reverse Northern blot, in which the substrate nucleic acid that is affixed to the membrane is a collection of isolated DNA fragments and the probe is RNA extracted from a tissue and labeled.

3. Amplification

Chromosomal rearrangements of genomic DNA and chimeric mRNA may be amplified prior to or simultaneous with detection. Illustrative non-limiting examples of nucleic acid amplification techniques include, but are not limited to, polymerase chain reaction (PCR), reverse transcription polymerase chain reaction (RT-PCR), transcription-mediated amplification (TMA), ligase chain reaction (LCR), strand displacement amplification (SDA), and nucleic acid sequence based amplification (NASBA). Those of ordinary skill in the art will recognize that certain amplification techniques (e.g., PCR) require that RNA be reversed transcribed to DNA prior to amplification (e.g., RT-PCR), whereas other amplification techniques directly amplify RNA (e.g., TMA and NASBA).

The polymerase chain reaction (U.S. Pat. Nos. 4,683,195, 4,683,202, 4,800,159 and 4,965,188, each of which is herein incorporated by reference in its entirety), commonly referred to as PCR, uses multiple cycles of denaturation, annealing of primer pairs to opposite strands, and primer extension to exponentially increase copy numbers of a target nucleic acid sequence. In a variation called RT-PCR, reverse transcriptase (RT) is used to make a complementary DNA (cDNA) from mRNA, and the cDNA is then amplified by PCR to produce multiple copies of DNA. For other various permutations of PCR see, e.g., U.S. Pat. Nos. 4,683,195, 4,683,202 and 4,800,159; Mullis et al., *Meth. Enzymol.* 155: 335 (1987); and, Murakawa et al., *DNA* 7: 287 (1988), each of which is herein incorporated by reference in its entirety.

Transcription mediated amplification (U.S. Pat. Nos. 5,480,784 and 5,399,491, each of which is herein incorporated by reference in its entirety), commonly referred to as TMA, synthesizes multiple copies of a target nucleic acid sequence autocatalytically under conditions of substantially constant temperature, ionic strength, and pH in which multiple RNA copies of the target sequence autocatalytically generate additional copies. See, e.g., U.S. Pat. Nos. 5,399, 491 and 5,824,518, each of which is herein incorporated by reference in its entirety. In a variation described in U.S. Publ. No. 20060046265 (herein incorporated by reference in its entirety), TMA optionally incorporates the use of blocking moieties, terminating moieties, and other modifying moieties to improve TMA process sensitivity and accuracy.

The ligase chain reaction (Weiss, R., *Science* 254: 1292 (1991), herein incorporated by reference in its entirety), commonly referred to as LCR, uses two sets of complementary DNA oligonucleotides that hybridize to adjacent regions of the target nucleic acid. The DNA oligonucleotides are covalently linked by a DNA ligase in repeated cycles of thermal denaturation, hybridization and ligation to produce a detectable double-stranded ligated oligonucleotide product.

Strand displacement amplification (Walker, G. et al., *Proc. Natl. Acad. Sci. USA* 89: 392-396 (1992); U.S. Pat. Nos. 5,270,184 and 5,455,166, each of which is herein incorporated by reference in its entirety), commonly referred to as SDA, uses cycles of annealing pairs of primer sequences to opposite strands of a target sequence, primer extension in the presence of a dNTPαS to produce a duplex hemiphosphorothioated primer extension product, endonuclease-mediated nicking of a hemimodified restriction endonuclease recognition site, and polymerase-mediated primer extension from the 3' end of the nick to displace an existing strand and produce a strand for the next round of primer annealing, nicking and strand displacement, resulting in geometric amplification of product. Thermophilic SDA (tSDA) uses thermophilic endonucleases and polymerases at higher temperatures in essentially the same method (EP Pat. No. 0 684 315).

Other amplification methods include, for example: nucleic acid sequence based amplification (U.S. Pat. No. 5,130,238, herein incorporated by reference in its entirety), commonly referred to as NASBA; one that uses an RNA replicase to amplify the probe molecule itself (Lizardi et al., *BioTechnol.* 6: 1197 (1988), herein incorporated by reference in its entirety), commonly referred to as Qβ replicase; a transcription based amplification method (Kwoh et al., *Proc. Natl. Acad. Sci. USA* 86:1173 (1989)); and, self-sustained sequence replication (Guatelli et al., *Proc. Natl. Acad. Sci. USA* 87: 1874 (1990), each of which is herein incorporated by reference in its entirety). For further discussion of known amplification methods see Persing, David H., "In Vitro Nucleic Acid Amplification Techniques" in *Diagnostic Medical Microbiology: Principles and Applications* (Persing et al., Eds.), pp. 51-87 (American Society for Microbiology, Washington, D.C. (1993)).

4. Detection Methods

Non-amplified or amplified gene rearrangement nucleic acids can be detected by any conventional means. For example, the gene rearrangements can be detected by hybridization with a detectably labeled probe and measurement of the resulting hybrids. Illustrative non-limiting examples of detection methods are described below.

One illustrative detection method, the Hybridization Protection Assay (HPA) involves hybridizing a chemiluminescent oligonucleotide probe (e.g., an acridinium ester-labeled (AE) probe) to the target sequence, selectively hydrolyzing the chemiluminescent label present on unhybridized probe, and measuring the chemiluminescence produced from the remaining probe in a luminometer. See, e.g., U.S. Pat. No. 5,283,174 and Norman C. Nelson et al., Nonisotopic Probing, Blotting, and Sequencing, ch. 17 (Larry J. Kricka ed., 2d ed. 1995, each of which is herein incorporated by reference in its entirety).

Another illustrative detection method provides for quantitative evaluation of the amplification process in real-time. Evaluation of an amplification process in "real-time" involves determining the amount of amplicon in the reaction mixture either continuously or periodically during the amplification reaction, and using the determined values to calculate the amount of target sequence initially present in the sample. A variety of methods for determining the amount of initial target sequence present in a sample based on real-time amplification are well known in the art. These include methods disclosed in U.S. Pat. Nos. 6,303,305 and 6,541, 205, each of which is herein incorporated by reference in its entirety. Another method for determining the quantity of target sequence initially present in a sample, but which is not based on a real-time amplification, is disclosed in U.S. Pat. No. 5,710,029, herein incorporated by reference in its entirety.

Amplification products may be detected in real-time through the use of various self-hybridizing probes, most of which have a stem-loop structure. Such self-hybridizing probes are labeled so that they emit differently detectable signals, depending on whether the probes are in a self-hybridized state or an altered state through hybridization to a target sequence. By way of non-limiting example, "molecular torches" are a type of self-hybridizing probe that includes distinct regions of self-complementarity (referred to as "the target binding domain" and "the target closing domain") which are connected by a joining region (e.g., non-nucleotide linker) and which hybridize to each other under predetermined hybridization assay conditions. In a preferred embodiment, molecular torches contain single-stranded base regions in the target binding domain that are from 1 to about 20 bases in length and are accessible for hybridization to a target sequence present in an amplification reaction under strand displacement conditions. Under strand displacement conditions, hybridization of the two complementary regions, which may be fully or partially complementary, of the molecular torch is favored, except in the presence of the target sequence, which will bind to the single-stranded region present in the target binding domain and displace all or a portion of the target closing domain. The target binding domain and the target closing domain of a molecular torch include a detectable label or a pair of interacting labels (e.g., luminescent/quencher) positioned so that a different signal is produced when the molecular torch is self-hybridized than when the molecular torch is hybridized to the target sequence, thereby permitting detection of probe:target duplexes in a test sample in the presence of unhybridized molecular torches. Molecular torches and many types of interacting label pairs are known (e.g., U.S. Pat. No. 6,534,274, herein incorporated by reference in its entirety).

Another example of a detection probe having self-complementarity is a "molecular beacon" (see U.S. Pat. Nos. 5,925,517 and 6,150,097, herein incorporated by reference in entirety). Molecular beacons include nucleic acid molecules having a target complementary sequence, an affinity pair (or nucleic acid arms) holding the probe in a closed conformation in the absence of a target sequence present in an amplification reaction, and a label pair that interacts when the probe is in a closed conformation. Hybridization of the target sequence and the target complementary sequence separates the members of the affinity pair, thereby shifting the probe to an open conformation. The shift to the open conformation is detectable due to reduced interaction of the label pair, which may be, for example, a fluorophore and a quencher (e.g., DABCYL and EDANS).

Other self-hybridizing probes are well known to those of ordinary skill in the art. By way of non-limiting example, probe binding pairs having interacting labels (e.g., see U.S. Pat. No. 5,928,862, herein incorporated by reference in its entirety) may be adapted for use in the compositions and methods disclosed herein. Probe systems used to detect single nucleotide polymorphisms (SNPs) might also be used. Additional detection systems include "molecular switches," (e.g., see U.S. Publ. No. 20050042638, herein incorporated by reference in its entirety). Other probes, such as those comprising intercalating dyes and/or fluorochromes, are also useful for detection of amplification products in the methods disclosed herein (e.g., see U.S. Pat. No. 5,814,447, herein incorporated by reference in its entirety).

C. Data Analysis

In some embodiments, a computer-based analysis program is used to translate the raw data generated by the detection assay (e.g., the presence, absence, or amount of a given marker or markers) into data of predictive value for a clinician. The clinician can access the predictive data using any suitable means. Thus, in some preferred embodiments, the present invention provides the further benefit that the clinician, who is not likely to be trained in genetics or molecular biology, need not understand the raw data. The data is presented directly to the clinician in its most useful form. The clinician is then able to immediately utilize the information in order to optimize the care of the subject.

Any method may be used that is capable of receiving, processing, and transmitting the information to and from laboratories conducting the assays, information provides, medical personal, and subjects. For example, in some embodiments of the present invention, a sample (e.g., a biopsy or a serum or urine sample) is obtained from a subject and submitted to a profiling service (e.g., clinical lab at a medical facility, genomic profiling business, etc.), located in any part of the world (e.g., in a country different than the country where the subject resides or where the information is ultimately used) to generate raw data. Where the sample comprises a tissue or other biological sample, the subject may visit a medical center to have the sample obtained and sent to the profiling center, or subjects may collect the sample themselves (e.g., a urine sample) and directly send it to a profiling center. Where the sample comprises previously determined biological information, the information may be directly sent to the profiling service by the subject (e.g., an information card containing the information may be scanned by a computer and the data transmitted to a computer of the profiling center using an electronic communication systems). Once received by the profiling service, the sample is processed and a profile is produced (i.e., expression data), specific for the diagnostic or prognostic information desired for the subject.

The profile data is then prepared in a format suitable for interpretation by a treating clinician. For example, rather than providing raw expression data, the prepared format may represent a diagnosis or risk assessment (e.g., likelihood of cancer being present) for the subject, along with recommendations for particular treatment options. The data may be displayed to the clinician by any suitable method. For example, in some embodiments, the profiling service generates a report that can be printed for the clinician (e.g., at the point of care) or displayed to the clinician on a computer monitor.

In some embodiments, the information is first analyzed at the point of care or at a regional facility. The raw data is then sent to a central processing facility for further analysis and/or to convert the raw data to information useful for a clinician or patient. The central processing facility provides the advantage of privacy (all data is stored in a central facility with uniform security protocols), speed, and uniformity of data analysis. The central processing facility can then control the fate of the data following treatment of the subject. For example, using an electronic communication system, the central facility can provide data to the clinician, the subject, or researchers.

In some embodiments, the subject is able to directly access the data using the electronic communication system. The subject may chose further intervention or counseling based on the results. In some embodiments, the data is used for research use. For example, the data may be used to further optimize the inclusion or elimination of markers as useful indicators of a particular condition or stage of disease.

D. In Vivo Imaging

The gene rearrangements disclosed herein may also be detected using in vivo imaging techniques, including but not limited to: radionuclide imaging; positron emission tomography (PET); computerized axial tomography, X-ray or magnetic resonance imaging method, fluorescence detection, and chemiluminescent detection. In some embodiments, in vivo imaging techniques are used to visualize the presence of or expression of cancer markers in an animal (e.g., a human or non-human mammal). For example, in some embodiments, cancer marker mRNA or protein is labeled using a labeled antibody specific for the cancer marker. A specifically bound and labeled antibody can be detected in an individual using an in vivo imaging method, including, but not limited to, radionuclide imaging, positron emission tomography, computerized axial tomography, X-ray or magnetic resonance imaging method, fluorescence detection, and chemiluminescent detection. Methods for generating antibodies to the disclosed cancer markers are described above.

The in vivo imaging methods that use the compositions disclosed herein that detect MIPOL1-ETV1 rearrangements or products derived from them are useful in the diagnosis of cancers, particularly prostate cancer, that express the cancer markers disclosed herein. In vivo imaging visualizes the presence of a marker indicative of the cancer, allowing diagnosis and/or prognosis without the use of an unpleasant biopsy. For example, the presence of a marker indicative of cancers likely to metastasize can be detected. The in vivo imaging methods can further be used to detect metastatic cancers in other parts of the body.

In some embodiments, reagents (e.g., antibodies) specific for the cancer markers associated with MIPOL1-ETV1 genetic rearrangements are fluorescently labeled. The labeled antibodies are introduced into a subject (e.g., orally or parenterally). Fluorescently labeled antibodies are detected using any suitable method or system (e.g., see U.S. Pat. No. 6,198,107, herein incorporated by reference).

In other embodiments, antibodies are radioactively labeled. The use of antibodies for in vivo diagnosis is well known in the art, e.g., by using an antibody-based labeling system to image tumors (see Sumerdon et al., Nucl. Med. Biol 17:247-254 [1990], Griffin et al., J. Clin. Onc. 9:631-640 [1991], and Lauffer, Magnetic Resonance in Medicine 22:339-342 [1991]). The label used with an antibody-based system will depend on the imaging modality chosen, for example, radioactive labels such as Indium-111, Technetium-99m, or Iodine-131 for use with planar scans or single photon emission computed tomography (SPECT), positron emitting labels such as Fluorine-19 for use with positron emission tomography (PET), and paramagnetic ions such as Gadolinium (III) or Manganese (II) for use with MRI.

Radioactive metals with half-lives ranging from 1 hour to 3.5 days are available for conjugation to antibodies, such as scandium-47 (3.5 days) gallium-67 (2.8 days), gallium-68 (68 minutes), technetium-99m (6 hours), and indium-111 (3.2 days), of which gallium-67, technetium-99m, and indium-111 are preferable for gamma camera imaging, gallium-68 is preferable for positron emission tomography.

A useful method of labeling antibodies with such radiometals is by means of a bifunctional chelating agent, such as diethylenetriaminepentaacetic acid (DTPA), as described, for example, by Khaw et al. (Science 209:295 [1980]) for In-111 and Tc-99m, and by Scheinberg et al. (Science 215:1511 [1982]). Other chelating agents may also be used, but the 1-(p-carboxymethoxybenzyl)EDTA and the carboxycarbonic anhydride of DTPA are advantageous because their use permits conjugation without affecting the antibody's immunoreactivity substantially.

Another method for coupling DPTA to proteins is by use of the cyclic anhydride of DTPA, as described by Hnatowich et al. (Int. J. Appl. Radiat. Isot. 33:327 [1982]) for labeling of albumin with In-111, but which can be adapted for labeling of antibodies. A suitable method of labeling antibodies with Tc-99m is known (e.g., see Crockford et al., U.S. Pat. No. 4,323,546, herein incorporated by reference).

A preferred method of labeling immunoglobulins with Tc-99m is that described by Wong et al. (Int. J. Appl. Radiat. Isot., 29:251 [1978]) for plasma protein, and recently applied successfully by Wong et al. (J. Nucl. Med., 23:229 [1981]) for labeling antibodies.

In the case of the radiometals conjugated to the specific antibody, it is likewise desirable to introduce as high a proportion of the radiolabel as possible into the antibody molecule without destroying its immunospecificity. A further improvement may be achieved by effecting radiolabeling in the presence of the specific cancer marker associated with a MIPOL1-ETV1 genetic rearrangement, to insure that the antigen binding site on the antibody is protected. The antigen is separated after labeling.

In still further embodiments, in vivo biophotonic imaging (Xenogen, Almeda, Calif.) is used for in vivo imaging. This real-time in vivo imaging utilizes luciferase, an enzyme that catalyzes a light-emitting reaction. The luciferase gene is incorporated into cells, microorganisms, and animals (e.g., to produce a fusion protein with a cancer marker associated with a MIPOL1-ETV1 genetic rearrangement), so that when the cancer marker is active a light emission occurs which is captured as an image and analyzed by using a CCD camera and appropriate software.

E. Compositions & Kits

Compositions for use in the disclosed diagnostic methods include, but are not limited to, probes, amplification oligonucleotides, and antibodies. The compositions detect a product only when a MIPOL1-ETV1 rearrangement is present, preferably ETV1 genetic material inserted into MIPOL1 genetic material. These compositions include, but are not limited to: a single labeled probe comprising a sequence that hybridizes to the junction at which ETV1 is inserted into the MIPOL1 locus (i.e., spans the gene rearrangement junction); a pair of amplification oligonucleotides wherein the first amplification oligonucleotide comprises a sequence that hybridizes to MIPOL1 and a second amplification oligonucleotide comprising a sequence that hybridizes to ETV1.

Other useful compositions, however, include: a pair of labeled probes wherein the first labeled probe comprises a sequence that hybridizes to MIPOL1 and the second labeled probe comprises a sequence that hybridizes to ETV1.

Any of these compositions, alone or in combination with other compositions disclosed herein or well known in the art, may be provided in the form of a kit. For example, the single labeled probe and pair of amplification oligonucleotides may be provided in a kit for the amplification and detection of MIPOL1-ETV1 genetic rearrangements. Kits may further comprise appropriate controls and/or detection reagents. Any one or more reagents that find use in any of the methods described herein may be provided in the kit.

The probe and antibody compositions may also be provided in the form of an array.

IV. Drug Screening Applications

In some embodiments, the disclosed compositions and methods are used in drug screening assays (e.g., to screen for anticancer drugs). These screening methods use cancer markers that include those associated with MIPOL1-ETV1 gene rearrangements, but are not limited only to those genetic rearrangements. For example, an embodiment may screen for compounds that alter (e.g., decrease) the expression of cancer marker genes, including those associated with MIPOL1-ETV1 gene rearrangements. Compounds or agents to be screened for may interfere with transcription (e.g., by interacting with a promoter region), may interfere with mRNA produced from the rearrangement (e.g., by RNA interference, antisense technologies, etc.), or may interfere with pathways that are upstream or downstream of the biological activity of the gene rearrangement. In some embodiments, candidate compounds are antisense or interfering RNA agents (e.g., oligonucleotides) directed against cancer markers. In other embodiments, candidate compounds are antibodies or small molecules that specifically bind to a cancer marker regulator or expression product associated with MIPOL1-ETV1 gene rearrangements and inhibit its biological function.

In some embodiments, candidate compounds are evaluated for their ability to alter cancer marker expression by contacting a compound with a cell expressing a cancer marker and then assaying for the effect of the candidate compounds on expression. In some embodiments, the effect of candidate compounds on expression of a cancer marker gene is assayed for by detecting the level of cancer marker mRNA expressed by the cell. mRNA expression can be detected by any suitable method. In other embodiments, the effect of candidate compounds on expression of cancer marker genes is assayed by measuring the level of polypeptide encoded by the cancer markers. The level of polypeptide expressed can be measured using any suitable method, including but not limited to, those disclosed herein.

The test compounds can be obtained using any of the numerous approaches in combinatorial library methods known in the art, including biological libraries; peptoid libraries (libraries of molecules having the functionalities of peptides, but with a novel, non-peptide backbone, which are resistant to enzymatic degradation but which nevertheless remain bioactive; see, e.g., Zuckennann et al., J. Med. Chem. 37: 2678-85 [1994]); spatially addressable parallel solid phase or solution phase libraries; synthetic library methods requiring deconvolution; the 'one-bead one-compound' library method; and synthetic library methods using affinity chromatography selection. The biological library and peptoid library approaches are preferred for use with peptide libraries, while the other four approaches are applicable to peptide, non-peptide oligomer or small molecule libraries of compounds (Lam (1997) Anticancer Drug Des. 12:145).

Examples of methods for the synthesis of molecular libraries can be found in the art, for example in: DeWitt et al., Proc. Natl. Acad. Sci. U.S.A. 90:6909 [1993]; Erb et al., Proc. Nad. Acad. Sci. USA 91:11422 [1994]; Zuckermann et al., J. Med. Chem. 37:2678 [1994]; Cho et al., Science 261:1303 [1993]; Carrell et al., Angew. Chem. Int. Ed. Engl. 33.2059 [1994]; Carell et al., Angew. Chem. Int. Ed. Engl. 33:2061 [1994]; and Gallop et al., J. Med. Chem. 37:1233 [1994].

Libraries of compounds may be presented in solution (e.g., Houghten, Biotechniques 13:412-421 [1992]), or on beads (Lam, Nature 354:82-84 [1991]), chips (Fodor, Nature 364:555-556 [1993]), bacteria or spores (U.S. Pat. No. 5,223,409; herein incorporated by reference), plasmids (Cull et al., Proc. Nad. Acad. Sci. USA 89:18651869 [1992]) or on phage (Scott and Smith, Science 249:386-390 [1990]; Devlin Science 249:404-406 [1990]; Cwirla et al., Proc. NatI. Acad. Sci. 87:6378-6382 [1990]; Felici, J. Mol. Biol. 222: 301 [1991]).

VI. Therapeutic Applications

Some embodiments provide therapies for cancer (e.g., prostate cancer). Preferred therapy embodiments target directly or indirectly cancer markers, including those associated with MIPOL1-ETV1 genetic rearrangements.

A. RNA Interference and Antisense Therapies

Some embodiments target the expression of cancer markers associated with MIPOL1-ETV1 genetic rearrangements. Some embodiments employ compositions comprising oligomeric antisense or RNAi compounds, particularly oligonucleotides (e.g., those identified in the drug screening methods described above), for use in modulating the function of nucleic acid molecules encoding cancer markers associated with MIPOL1-ETV1 genetic rearrangements, ultimately modulating the amount of cancer marker expressed.

1. RNA Interference (RNAi)

In some embodiments, RNAi is used to inhibit expression of MIPOL1-ETV1 gene rearrangements. RNAi represents an evolutionary conserved cellular defense for controlling the expression of foreign genes in most eukaryotes, including humans. RNAi is typically triggered by double-stranded RNA (dsRNA) and causes sequence-specific mRNA degradation of single-stranded target RNAs homologous in response to dsRNA. The mediators of mRNA degradation are small interfering RNA duplexes (siRNAs), which are normally produced from long dsRNA by enzymatic cleavage in the cell. siRNAs are generally approximately twenty-one nucleotides in length (e.g. 21-23 nucleotides in length), and have a base-paired structure characterized by two nucleotide 3'-overhangs. Following the introduction of a small RNA, or RNAi, into the cell, it is believed the sequence is delivered to an enzyme complex called RISC (RNA-induced silencing complex). RISC recognizes the target and cleaves it with an endonuclease. It is noted that if larger RNA sequences are delivered to a cell, RNase III enzyme (Dicer) converts longer dsRNA into 21-23 nt ds siRNA fragments. In some embodiments, RNAi oligonucleotides are designed to target the junction region of gene rearrangements.

Chemically synthesized siRNAs have become powerful reagents for genome-wide analysis of mammalian gene function in cultured somatic cells. Beyond their value for validation of gene function, siRNAs also hold great potential as gene-specific therapeutic agents (Tuschl and Borkhardt, Molecular Intervent. 2002; 2(3):158-67, herein incorporated by reference).

The transfection of siRNAs into animal cells results in the potent, long-lasting post-transcriptional silencing of specific genes (Caplen et al, Proc Natl Acad Sci U.S.A. 2001; 98: 9742-7; Elbashir et al., Nature. 2001; 411:494-8; Elbashir et al., Genes Dev. 2001; 15: 188-200; and Elbashir et al., EMBO J. 2001; 20: 6877-88, all of which are herein incorporated by reference). Methods and compositions for performing RNAi with siRNAs are known (e.g., see U.S. Pat. No. 6,506,559, herein incorporated by reference).

siRNAs are extraordinarily effective at lowering the amounts of targeted RNA, and by extension proteins, frequently to undetectable levels. The silencing effect can last several months, and is extraordinarily specific, because one nucleotide mismatch between the target RNA and the central region of the siRNA is frequently sufficient to prevent silencing (Brummelkamp et al, Science 2002; 296:550-3; and Holen et al, Nucleic Acids Res. 2002; 30:1757-66, both of which are herein incorporated by reference).

An important factor in the design of siRNAs is the presence of accessible sites for siRNA binding. Bahoia et al., (J. Biol. Chem., 2003; 278: 15991-15997; herein incorporated by reference) describe the use of a type of DNA array called a scanning array to find accessible sites in mRNAs for designing effective siRNAs. These arrays comprise oligonucleotides ranging in size from monomers to a certain maximum, usually Comers, synthesized using a physical barrier (mask) by stepwise addition of each base in the sequence. Thus the arrays represent a full oligonucleotide complement of a region of the target gene. Hybridization of the target mRNA to these arrays provides an exhaustive accessibility profile of this region of the target mRNA. Such data are useful in the design of antisense oligonucleotides (ranging from 7mers to 25mers), where it is important to achieve a compromise between oligonucleotide length and binding affinity, to retain efficacy and target specificity (Sohail et al, Nucleic Acids Res., 2001; 29(10): 2041-2045). Additional methods and concerns for selecting siRNAs are described for example, in WO 05054270, WO05038054A1, WO03070966A2, J Mol Biol. 2005 May 13; 348(4):883-93, J Mol Biol. 2005 May 13; 348(4):871-81, and Nucleic Acids Res. 2003 Aug. 1; 31(15):4417-24, each of which is herein incorporated by reference in its entirety. In addition, software (e.g., the MWG online siMAX siRNA design tool) is commercially or publicly available for use in the selection of siRNAs.

2. Antisense

In other embodiments, expression of MIPOL1-ETV1 gene rearrangements is modulated using antisense compounds that specifically hybridize with one or more nucleic acids encoding cancer markers associated with MIPOL1-ETV1 genetic rearrangements. The specific hybridization of an oligomeric compound with its target nucleic acid interferes with the normal function of the nucleic acid. This modulation of function of a target nucleic acid by compounds that specifically hybridize to it is generally referred to as "antisense." The functions of DNA to be interfered with include replication and transcription. The functions of RNA to be interfered with include all vital functions such as, for example, translocation of the RNA to the site of protein translation, translation of protein from the RNA, splicing of the RNA to yield one or more mRNA species, and catalytic activity that may be engaged in or facilitated by the RNA. The overall effect of such interference with target nucleic acid function is modulation of the expression of cancer markers associated with MIPOL1-ETV1 genetic rearrangements. Herein, "modulation" means either an increase (stimulation) or a decrease (inhibition) in the expression of a gene. For example, expression may be inhibited to potentially prevent tumor proliferation.

Antisense methods preferably target specific nucleic acids. "Targeting" an antisense compound to a particular nucleic acid usually refers to a multistep process that begins with identification of a nucleic acid sequence whose function is to be modulated. This may be, e.g., a cellular gene (or mRNA transcribed from the gene) whose expression is associated with a particular disorder or disease state, or a nucleic acid molecule from an infectious agent. Herein, the target is a nucleic acid molecule encoding a cancer marker associated with MIPOL1-ETV1 genetic rearrangements. The targeting process also includes determination of a site or sites within this gene for the antisense interaction to occur such that the desired effect, e.g., detection or modulation of expression of the protein, will result. Herein, a preferred intragenic site is the region encompassing the translation initiation or termination codon of the open reading frame (ORF) of the gene. Since the translation initiation codon is typically 5'-AUG (in transcribed mRNA molecules; 5'-ATG in the corresponding DNA molecule), the translation initiation codon is also referred to as the "AUG codon," the "start codon" or the "AUG start codon". A minority of genes have a translation initiation codon having the RNA sequence 5'-GUG, 5'-UUG or 5'-CUG, and 5'-AUA, 5'-ACG and 5'-CUG have been shown to function in vivo. Thus, the terms "translation initiation codon" and "start codon" can encompass many codon sequences, even though the initiator amino acid in each instance is typically methionine (in eukaryotes) or formylmethionine (in prokaryotes). Eukaryotic and prokaryotic genes may have two or more alternative start codons, any one of which may be preferentially used for translation initiation in a particular cell type or tissue, or under a particular set of conditions. Herein, "start codon" and "translation initiation codon" refer to the codon or codons that are used in vivo to initiate translation of an mRNA molecule transcribed from a gene encoding a tumor antigen associated with MIPOL1-ETV1 genetic rearrangements, regardless of the sequence(s) of such codons.

Translation termination codon (or "stop codon") of a gene may have one of three sequences (i.e., 5'-UAA, 5'-UAG and 5'-UGA; the corresponding DNA sequences are 5'-TAA, 5'-TAG and 5'-TGA, respectively). The terms "start codon region" and "translation initiation codon region" refer to a portion of such an mRNA or gene that encompasses from about 25 to about 50 contiguous nucleotides in either direction (i.e., 5' or 3') from a translation initiation codon. Similarly, the terms "stop codon region" and "translation termination codon region" refer to a portion of such an mRNA or gene that encompasses from about 25 to about 50 contiguous nucleotides in either direction (i.e., 5' or 3') from a translation termination codon.

The open reading frame (ORF) or "coding region," which refers to the region between the translation initiation codon and the translation termination codon, is also a region that may be targeted effectively. Other target regions include the 5' untranslated region (5' UTR), referring to the portion of an mRNA in the 5' direction from the translation initiation codon, and thus including nucleotides between the 5' cap site and the translation initiation codon of an mRNA or corresponding nucleotides on the gene, and the 3' untranslated region (3' UTR), referring to the portion of an mRNA in the 3' direction from the translation termination codon, and thus including nucleotides between the translation termination codon and 3' end of an mRNA or corresponding nucleotides on the gene. The 5' cap of an mRNA comprises an N7-methylated guanosine residue joined to the 5'-most residue of the mRNA via a 5'-5' triphosphate linkage. The 5' cap region of an mRNA is considered to include the 5' cap structure itself as well as the first 50 nucleotides adjacent to the cap. The cap region may also be a preferred target region.

Although some eukaryotic mRNA transcripts are directly translated, many contain one or more regions, known as "introns," that are excised from a transcript before it is translated. The remaining (and therefore translated) regions are known as "exons" and are spliced together to form a continuous mRNA sequence. mRNA splice sites (i.e., intron-exon junctions) may also be preferred target regions, and are particularly useful in situations where aberrant splicing is implicated in disease, or where an overproduction of a particular mRNA splice product is implicated in disease. Aberrant fusion junctions due to rearrangements or deletions are also preferred targets. It has also been found that introns can also be effective, and therefore preferred, target regions for antisense compounds targeted, for example, to DNA or pre-mRNA.

In some embodiments, target sites for antisense inhibition are identified using commercially available software programs (e.g., Biognostik, Gottingen, Germany; SysArris Software, Bangalore, India; Antisense Research Group, University of Liverpool, Liverpool, England; GeneTrove, Carlsbad, Calif.). In other embodiments, target sites for antisense inhibition are identified using the accessible site method described in PCT Publ. No. WO0198537A2, herein incorporated by reference.

Once one or more target sites have been identified, oligonucleotides are chosen that are sufficiently complementary to the target (i.e., hybridize sufficiently well and with sufficient specificity) to give the desired effect. For example, in preferred embodiments, antisense oligonucleotides are targeted to or near the start codon associated with MIPOL1-ETV1 genetic rearrangements.

In the context of this invention, "hybridization," with respect to antisense compositions and methods, means hydrogen bonding, which may be Watson-Crick, Hoogsteen or reversed Hoogsteen hydrogen bonding, between complementary nucleoside or nucleotide bases. For example, adenine and thymine are complementary nucleobases that pair through the formation of hydrogen bonds. It is understood that the sequence of an antisense compound need not be 100% complementary to that of its target nucleic acid to be specifically hybridizable. An antisense compound is specifically hybridizable when binding of the compound to the target DNA or RNA molecule interferes with the normal function of the target DNA or RNA to cause a loss of utility, and there is a sufficient degree of complementarity to avoid non-specific binding of the antisense compound to non-target sequences under conditions in which specific binding is desired (i.e., under physiological conditions in the case of in vivo assays or therapeutic treatment, and in the case of in vitro assays, under conditions in which the assays are performed).

Antisense compounds are commonly used as research reagents and diagnostics. For example, antisense oligonucleotides, which are able to inhibit gene expression with specificity, can be used to elucidate the function of particular genes. Antisense compounds are also used, for example, to distinguish between functions of various members of a biological pathway.

The specificity and sensitivity of antisense is also applied for therapeutic uses. For example, antisense oligonucleotides have been employed as therapeutic moieties in the treatment of disease states in animals and man. Antisense oligonucleotides have been safely and effectively administered to humans and numerous clinical trials are presently underway. It is thus established that oligonucleotides are useful therapeutic modalities that can be configured to be useful in treatment regimes for treatment of cells, tissues, and animals, especially humans.

While antisense oligonucleotides are preferred, other oligomeric antisense compounds, including but not limited to oligonucleotide mimetics may be used, such as are described below. Preferred antisense compounds comprise from about 8 to about 30 nucleobases (i.e., from about 8 to about 30 linked bases), although both longer and shorter sequences may be used. Particularly preferred antisense compounds are antisense oligonucleotides, even more preferably those comprising from about 12 to about 25 nucleobases.

Specific examples of preferred antisense compounds include oligonucleotides containing modified backbones or non-natural internucleoside linkages. As defined herein, oligonucleotides having modified backbones include those that retain a phosphorus atom in the backbone and those that do not have a phosphorus atom in the backbone. For the purposes of this specification, modified oligonucleotides that do not have a phosphorus atom in their internucleoside backbone can also be considered to be oligonucleosides.

Preferred modified oligonucleotide backbones include, for example, phosphorothioates, chiral phosphorothioates, phosphorodithioates, phosphotriesters, aminoalkylphosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'. Various salts, mixed salts and free acid forms are also included.

Preferred modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and CH2 component parts.

In other preferred oligonucleotide mimetics, both the sugar and the internucleoside linkage (i.e., the backbone) of the nucleotide units are replaced with novel groups. The base units are maintained for hybridization with an appropriate nucleic acid target compound. One such oligomeric compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone. Methods for preparation of PNA compounds are well known (e.g., see U.S. Pat. Nos. 5,539,082; 5,714,331; and 5,719,262, and Nielsen et al., Science 254:1497 (1991), each of which is herein incorporated by reference). Most preferred embodiments of the invention are oligonucleotides with phosphorothioate backbones and oligonucleosides with heteroatom backbones, and in particular —CH2—, —NH—O—CH2—, —CH2-N(CH3)-O—CH2- [known as a methylene (methylimino) or MMI backbone], —CH2-O—N(CH3)-CH2-, —CH2-N(CH3)-N(CH3)-CH2-, and —O—N(CH3)-CH2-CH2- [wherein the native phosphodiester backbone is represented as —O—P—O—CH2-], amid backbone, and morpholino backbone structures, all of which are well known (e.g., see U.S. Pat. Nos. 5,489,677, 5,602,240, and 5,034,506).

Modified oligonucleotides may also contain one or more substituted sugar moieties. Preferred oligonucleotides comprise one of the following at the 2' position: OH; F; O—, S—, or N-alkyl; O—, S—, or N-alkenyl; O—, S—or N-alkynyl; or O-alkyl-O-alkyl, wherein the alkyl, alkenyl and alkynyl may be substituted or unsubstituted C1 to C10 alkyl or C2 to C10 alkenyl and alkynyl. Particularly preferred are O[(CH2)nO]mCH3, O(CH2)nOCH3, O(CH2)nNH2, O(CH2)nCH3, O(CH2)nONH2, and O(CH2)nON[(CH2)nCH3)]2, where n and m are from 1 to about 10. Other preferred oligonucleotides comprise one of the following at the 2' position: C1 to C10 lower alkyl, substituted lower alkyl, alkaryl, aralkyl, O-alkaryl or O-aralkyl, SH, SCH3, OCN, Cl, Br, CN, CF3, OCF3, SOCH3, SO2CH3, ONO2, NO2, N3, NH2, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. A preferred modification includes 2'-methoxyethoxy (2'-O—CH2CH2OCH3, also known as 2'-O-(2-methoxyethyl) or 2'-MOE) (Martin et al., Helv. Chim. Acta 78:486 [1995]) i.e., an alkoxyalkoxy group. A further preferred modification includes 2'-dimethylaminooxyethoxy (i.e., a O(CH2)2ON(CH3)2 group), also known as 2'-DMAOE, and 2'-dimethylaminoethoxyethoxy (also known in the art as 2'-O-dimethylaminoethoxyethyl or 2'-DMAEOE), i.e., 2'-O—CH2-O—CH2-N(CH2)2.

Other preferred modifications include 2'-methoxy(2'-O—CH3), 2'-aminopropoxy(2'-OCH2CH2CH2NH2) and 2'-fluoro (2'-F). Similar modifications may also be made at other positions on the oligonucleotide, particularly the 3' position of the sugar on the 3' terminal nucleotide or in 2'-5' linked oligonucleotides and the 5' position of 5' terminal nucleotide. Oligonucleotides may also have sugar mimetics such as cyclobutyl moieties in place of the pentofuranosyl sugar.

Oligonucleotides may also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases are well known (e.g., see U.S. Pat. No. 3,687,808) and include other synthetic and natural nucleobases (for which the A, G, T, C and U abbreviations for the bases are used in the following examples), such as 5-methylcytosine (5-me-C), 5-hydroxymethyl C, xanthine, hypoxanthine, 2-amino-A, 6-methyl or 2-propyl and other alkyl derivatives of A and G, 2-thio-U, 2-thio-T and 2-thio-C, 5-halo-U and -C, 5-propynyl U and C, 6-azo U, C and T, 5-uracil (pseudouracil), 4-thio-U, 8-halo, 8-amino, 8-thiol, 8-thioalkyl, 8-hydroxyl and other 8-substituted A and G, 5-halo substituted U and C, particularly 5-bromo, 5-trifluoromethyl and other 5-substituted U and C, 7-methyl-G and 7-methyl-A, 8-aza-G and 8-aza-A, 7-deaza-G and 7-deaza-A and 3-deaza-G and 3-deaza-A. Certain of these nucleobases are particularly useful for increasing the binding affinity of the oligomeric compounds of the invention. These include 5-substituted pyrimidines, 6-azapyrimidines and N-2, N-6 and O-6 substituted purines, including 2-aminopropyladenine, 5-propynyl-U and 5-propynyl-C. 5-methyl-C substitutions are known to increase nucleic acid duplex stability and are preferred base substitutions in some embodiments, even more particularly when combined with 2'-O-methoxyethyl sugar modifications.

Another modification of the oligonucleotides involves chemically linking to the oligonucleotide one or more moieties or conjugates that enhance the activity, cellular distribution or cellular uptake of the oligonucleotide. Such moieties include but are not limited to lipid moieties such as a cholesterol moiety, cholic acid, a thioether, (e.g., hexyl-S-tritylthiol), a thiocholesterol, an aliphatic chain, (e.g., dodecandiol or undecyl residues), a phospholipid, (e.g., di-hexadecyl-rac-glycerol or triethylammonium 1,2-di-O-hexadecyl-rac-glycero-3-H-phosphonate), a polyamine or a polyethylene glycol chain or adamantane acetic acid, a palmityl moiety, or an octadecylamine or hexylamino-carbonyl-oxycholesterol moiety.

One skilled in the relevant art knows well how to generate oligonucleotides containing the above-described modifications. The present invention is not limited to the antisense oligonucleotides described above. Any suitable modification or substitution may be used.

It is not necessary for all positions in a given compound to be uniformly modified, and in fact more than one of the aforementioned modifications may be incorporated in a single compound or even at a single nucleoside within an oligonucleotide. Antisense compounds may be chimeric compounds. "Chimeric" antisense compounds or "chimeras," as used herein, are antisense compounds, particularly oligonucleotides, which contain two or more chemically distinct regions, each made up of at least one monomer unit, i.e., a nucleotide in the case of an oligonucleotide compound. These oligonucleotides typically contain at least one region wherein the oligonucleotide is modified so as to confer upon the oligonucleotide increased resistance to nuclease degradation, increased cellular uptake, and/or increased binding affinity for the target nucleic acid. An additional region of the oligonucleotide may serve as a substrate for enzymes capable of cleaving RNA:DNA or RNA:RNA hybrids. By way of example, RNaseH is a cellular endonuclease that cleaves the RNA strand of an RNA:DNA duplex. Activation of RNase H, therefore, results in cleavage of the RNA target, thereby greatly enhancing the efficiency of oligonucleotide inhibition of gene expression. Consequently, comparable results can often be obtained with shorter oligonucleotides when chimeric oligonucleotides are used, compared to phosphorothioate deoxyoligonucleotides hybridizing to the same target region. Cleavage of the RNA target can be routinely detected by gel electrophoresis and, if necessary, associated nucleic acid hybridization techniques known in the art.

Chimeric antisense compounds may be formed as composite structures of two or more oligonucleotides, modified oligonucleotides, oligonucleosides and/or oligonucleotide mimetics as described above.

Other embodiments include pharmaceutical compositions and formulations that include the antisense compounds as described herein.

B. Gene Therapy

Embodiments may use any genetic manipulation to modulate the expression of cancer markers associated with MIPOL1-ETV1 genetic rearrangements described herein. Examples of genetic manipulation include, but are not limited to, gene knockout (such as by removing the genetic rearrangement from the chromosome using, e.g., by recombination), expression of antisense constructs with or without inducible promoters, and the like. Delivery of nucleic acid construct to cells in vitro or in vivo may be conducted using any suitable method. A suitable method is one that introduces the nucleic acid construct into the cell such that the desired event occurs (e.g., expression of an antisense construct). Genetic therapy may also be used to deliver siRNA or other interfering molecules that are expressed in vivo (e.g., upon stimulation by an inducible promoter (e.g., an androgen-responsive promoter)).

Introduction of molecules carrying genetic information into cells is achieved by any of various methods including, but not limited to, directed injection of naked DNA constructs, bombardment with gold particles loaded with said constructs, and macromolecule mediated gene transfer using, for example, liposomes, biopolymers, and the like. Preferred methods use gene delivery vehicles derived from viruses, including, but not limited to, adenoviruses, retroviruses, vaccinia viruses, and adeno-associated viruses. Because of the higher efficiency as compared to retroviruses, vectors derived from adenoviruses are the preferred gene delivery vehicles for transferring nucleic acid molecules into host cells in vivo. Adenoviral vectors and their use in gene transfer are well known (e.g., see PCT publications WO 00/12738 and WO 00/09675 and U.S. Pat. Nos. 6,033,908, 6,019,978, 6,001,557, 5,994,132, 5,994,128, 5,994,106, 5,981,225, 5,885,808, 5,872,154, 5,830,730, and 5,824,544, each of which is herein incorporated by reference in its entirety). Such vectors and methods have been shown to provide very efficient in vivo gene transfer into a variety of solid tumors in animal models and into human solid tumor xenografts in immune-deficient mice.

Vectors may be administered to subject in a variety of well known ways, e.g., administered into tumors or tissue associated with tumors by using direct injection or administration via the blood or lymphatic circulation (See e.g., PCT publication 99/02685 herein incorporated by reference in its entirety). Exemplary dose levels of adenoviral vector are preferably $10^8$ to $10^{11}$ vector particles added to the perfusate.

C. Antibody or Small Molecule Therapies

Some embodiments are or use antibodies and/or small molecules that target prostate tumors that express a cancer marker associated with MIPOL1-ETV1 genetic rearrangements. In some embodiments, the therapeutic regimen is selected based on a diagnostic result and uses a suitable antibody (e.g., monoclonal, polyclonal, or synthetic) in the therapeutic methods. In preferred embodiments, the antibodies used for cancer therapy are humanized antibodies. Methods for humanizing antibodies are well known (See e.g., U.S. Pat. Nos. 6,180,370, 5,585,089, 6,054,297, and 5,565,332; each of which is herein incorporated by reference).

In some embodiments, the therapeutic antibodies comprise an antibody generated against a cancer marker associated with MIPOL1-ETV1 genetic rearrangements, wherein the antibody is conjugated to a cytotoxic agent. In such embodiments, a tumor specific therapeutic agent is generated that does not target normal cells, thus reducing many of the detrimental side effects of traditional chemotherapy. For certain applications, it is envisioned that the therapeutic agents will be pharmacologic agents that will serve as useful agents for attachment to antibodies, particularly cytotoxic or otherwise anticellular agents having the ability to kill or suppress the growth or cell division of endothelial cells. Embodiments may use any pharmacologic agent that can be conjugated to an antibody, and delivered in active form. Exemplary anticellular agents include chemotherapeutic agents, radioisotopes, and cytotoxins. Such therapeutic antibodies may include a variety of cytotoxic moieties, including but not limited to, radioactive isotopes (e.g., iodine-131, iodine-123, technetium-99m, indium-111, rhenium-188, rhenium-186, gallium-67, copper-67, yttrium-90, iodine-125 or astatine-211), hormones such as a steroid, antimetabolites such as cytosines (e.g., arabinoside, fluorouracil, methotrexate or aminopterin; an anthracycline; mitomycin C), vinca alkaloids (e.g., demecolcine; etoposide; mithramycin), and antitumor alkylating agent such as chlorambucil or melphalan. Other embodiments may include agents such as a coagulant, a cytokine, growth factor, bacterial endotoxin or the lipid A moiety of bacterial endotoxin. For example, in some embodiments, therapeutic agents will include plant-, fungus- or bacteria-derived toxin, such as an A chain toxins, a ribosome inactivating protein, α-sarcin, aspergillin, restrictocin, a ribonuclease, diphtheria toxin or *pseudomonas* exotoxin, to mention just a few examples. In some preferred embodiments, deglycosylated ricin A chain is used.

In any event, it is proposed that agents such as these may, if desired, be successfully conjugated to an antibody, in a manner that will allow their targeting, internalization, release or presentation to blood components at the site of the targeted tumor cells as required using known conjugation technology (See, e.g., Ghose et al., Methods Enzymol., 93:280 [1983]).

For example, some embodiments provide immunotoxins targeted against cancer marker associated with MIPOL1-ETV1 genetic rearrangements. Immunotoxins are conjugates of a specific targeting agent typically a tumor-directed antibody or fragment, with a cytotoxic agent, such as a toxin moiety. The targeting agent directs the toxin to, and thereby selectively kills, cells carrying the targeted antigen. In some embodiments, therapeutic antibodies employ crosslinkers that provide high in vivo stability (Thorpe et al., Cancer Res., 48:6396 [1988]).

In other embodiments, particularly those involving treatment of solid tumors, antibodies are designed to have a cytotoxic or otherwise anticellular effect against the tumor vasculature, by suppressing the growth or cell division of the vascular endothelial cells. This attack is intended to lead to a tumor-localized vascular collapse, depriving the tumor cells, particularly those tumor cells distal of the vasculature, of oxygen and nutrients, ultimately leading to cell death and tumor necrosis.

In preferred embodiments, antibody based therapeutics are formulated as pharmaceutical compositions as described herein. In preferred embodiments, administration of an antibody composition that targets a moiety associated with MIPOL1-ETV1 genetic rearrangements results in a measurable decrease in cancer (e.g., decrease or elimination of tumor).

VII. Transgenic Animals

Embodiments include generation of transgenic animals comprising an exogenous cancer marker gene that is identical to or representative of a MIPOL1-ETV1 genetic rearrangement described herein, which includes mutants and variants thereof (e.g., truncations or single nucleotide polymorphisms). In preferred embodiments, the transgenic animal displays an altered phenotype (e.g., increased or decreased presence of markers associated with MIPOL1-ETV1 genetic rearrangements) as compared to wild-type animals. Methods for analyzing the presence or absence of such phenotypes include but are not limited to, those disclosed herein. In some preferred embodiments, the transgenic animals further display an increased or decreased growth of tumors or evidence of cancer.

Such transgenic animals are useful in drug (e.g., cancer therapy) screens. In some embodiments, test compounds (e.g., a drug that is suspected of being useful to treat cancer) and control compounds (e.g., a placebo) are administered to the transgenic animals and the control animals and the effects evaluated.

The transgenic animals can be generated via a variety of methods. In some embodiments, embryonal cells at various developmental stages are used to introduce transgenes for the production of transgenic animals. Different methods are used depending on the stage of development of the embryonal cell. The zygote is the best target for micro-injection. In the mouse, the male pronucleus reaches the size of approximately 20 micrometers in diameter that allows reproducible injection of 1-2 picoliters (pl) of DNA solution. The use of zygotes as a target for gene transfer has a major advantage in that in most cases the injected DNA will be incorporated into the host genome before the first cleavage (Brinster et al., Proc. Natl. Acad. Sci. USA 82:4438-4442 [1985]). As a consequence, all cells of the transgenic non-human animal carry the incorporated transgene. This is reflected in the efficient transmission of the transgene to offspring of the founder since 50% of the germ cells harbor the transgene based on standard Mendelian genetics. Methods for making transgenics are well known (e.g., see U.S. Pat. No. 4,873,191, which is herein incorporated by reference in its entirety).

In other embodiments, retroviral infection is used to introduce transgenes into a non-human animal. In some embodiments, the retroviral vector is used to transfect oocytes by injecting the retroviral vector into the perivitelline space of the oocyte (U.S. Pat. No. 6,080,912, incorporated herein by reference). In other embodiments, the developing non-human embryo can be cultured in vitro to the blastocyst stage. During this time, the blastomeres can be targets for retroviral infection (Janenich, Proc. Natl. Acad. Sci. USA 73:1260 [1976]). Efficient infection of the blastomeres is obtained by enzymatic treatment to remove the zona pellucida (Hogan et al., in *Manipulating the Mouse Embryo*, Cold Spring Harbor Laboratory Press, Cold Spring Harbor, N.Y. [1986]). The viral vector system used to introduce the transgene is typically a replication-defective retrovirus carrying the transgene (Jahner et al., Proc. Natl. Acad Sci. USA 82:6927 [1985]). Transfection is easily and efficiently obtained by culturing the blastomeres on a monolayer of virus-producing cells (Stewart, et al., EMBO J., 6:383 [1987]). Alternatively, infection can be performed at a later stage. Virus or virus-producing cells can be injected into the blastocoele (Jahner et al., Nature 298:623 [1982]). Most of the founders will be mosaic for the transgene since incorporation occurs only in a subset of cells that form the transgenic animal. Further, the founder may contain various retroviral insertions of the transgene at different positions in the genome that generally will segregate in the offspring. In addition, it is also possible to introduce transgenes into the germline, albeit with low efficiency, by intrauterine retroviral infection of the midgestation embryo (Jahner et al., supra [1982]). Additional means of using retroviruses or retroviral vectors to create transgenic animals known to the art involve the micro-injection of retroviral particles or mitomycin C-treated cells producing retrovirus into the perivitelline space of fertilized eggs or early embryos (PCT International Application WO 90/08832 [1990], and Haskell and Bowen, Mol. Reprod. Dev., 40:386 [1995]).

In other embodiments, the transgene is introduced into embryonic stem cells and the transfected stem cells are used to form an embryo. ES cells are obtained by culturing pre-implantation embryos in vitro under appropriate conditions (Evans et al., Nature 292:154 [1981]; Bradley et al., Nature 309:255 [1984]; Gossler et al., Proc. Acad. Sci. USA 83:9065 [1986]; and Robertson et al., Nature 322:445 [1986]). Transgenes can be efficiently introduced into the ES cells by DNA transfection by a variety of methods known to the art including calcium phosphate co-precipitation, protoplast or spheroplast fusion, lipofection and DEAE-dextran-mediated transfection. Transgenes may also be introduced into ES cells by retrovirus-mediated transduction or by micro-injection. Such transfected ES cells can thereafter colonize an embryo following their introduction into the blastocoel of a blastocyst-stage embryo and contribute to the germ line of the resulting chimeric animal (for review, See, Jaenisch, Science 240:1468 [1988]). Prior to the introduction of transfected ES cells into the blastocoel, the transfected ES cells may be subjected to various selection protocols to enrich for ES cells which have integrated the transgene assuming that the transgene provides a means for such selection. Alternatively, the polymerase chain reaction may be used to screen for ES cells that have integrated the transgene. This technique obviates the need for growth of the transfected ES cells under appropriate selective conditions prior to transfer into the blastocoel.

In still other embodiments, homologous recombination is used to knock-out gene function or create deletion mutants (e.g., truncation mutants), using well known methods (see U.S. Pat. No. 5,614,396, incorporated herein by reference).

EXPERIMENTAL

The following examples are provided to demonstrate and illustrate certain preferred embodiments and aspects of the compositions and methods disclosed herein, but are not to be construed as limiting the scope of the claimed invention.

Example 1

ETV1 Generic Rearrangements in Cell Lines

This example shows that LNCaP and MDA-PCa 2B cell lines harbor rearrangements that localize the ETV1 locus to 14q13.3-14q21.1.

Experiments were designed to identify cell line models of aberrant ETV1 activation. The prostate cancer cell line LNCaP has markedly over-expressed ETV1, but RLM-RACE revealed expression of only the wild type transcript (Tomlins et al., Science 310, 644-8 (2005)). These experiments were designed to identify in LNCaP cells a novel rearrangement affecting the expression of ETV1. Thus, a split-probe FISH strategy, consisting of one probe on and one probe 5' to the ETV1 locus, was used to look for gross rearrangements involving ETV1 (FIG. 1).

Interphase FISH on formalin-fixed paraffin-embedded (FFPE) tissue sections was performed using known methods (substantially as previously described in Tomlins et al., Cancer Res 66, 3396-400 (2006)). A minimum of 50 nuclei per assay were evaluated. Metaphase spreads of LNCaP and MDA-PCa 2B were prepared using standard cytogenetic techniques. Slides were pre-treated in 2×SSC for 2 min, 70% ethanol for 2 min and 100% ethanol for 2 min, and air dried. Slide samples and probes were co-denatured at 75° C. for 2 min, and hybridized overnight at 37° C. Post-hybridization was in 0.5×SSC at 42° C. for 5 min, followed by 3 washes in PBST. Fluorescent detection was performed using anti-digoxigenin conjugated to fluorescein (Roche Applied Science, Indianapolis, Ind.) and streptavidin conjugated to a fluorophore (Alexa Fluor 594, Invitrogen). Slides were counterstained and mounted using standard reagents and methods (in ProLong Gold Antifade Reagent with DAPI, Invitrogen). Slides were examined using a fluorescence microscope (Axio Imager Z1, Zeiss, Thornwood, N.Y.) and imaged with a CCD camera using a standard algorithm to analyze results (ISIS software, Metasystems, Altlussheim, Germany). BACs (listed in Table 2, obtained from the BACPAC Resource Center (Oakland, Calif.)) were used to prepare probes using previously described methods (Tomline et al., 2006, supra). Pre-labeled chromosome 7 centromere and 7p telomeric probes were also used (from Vysis Corp., Des Plaines, Ill.). The integrity and correct localization of all probes were verified by hybridization to metaphase spreads of normal peripheral lymphocytes.

Figure 2:
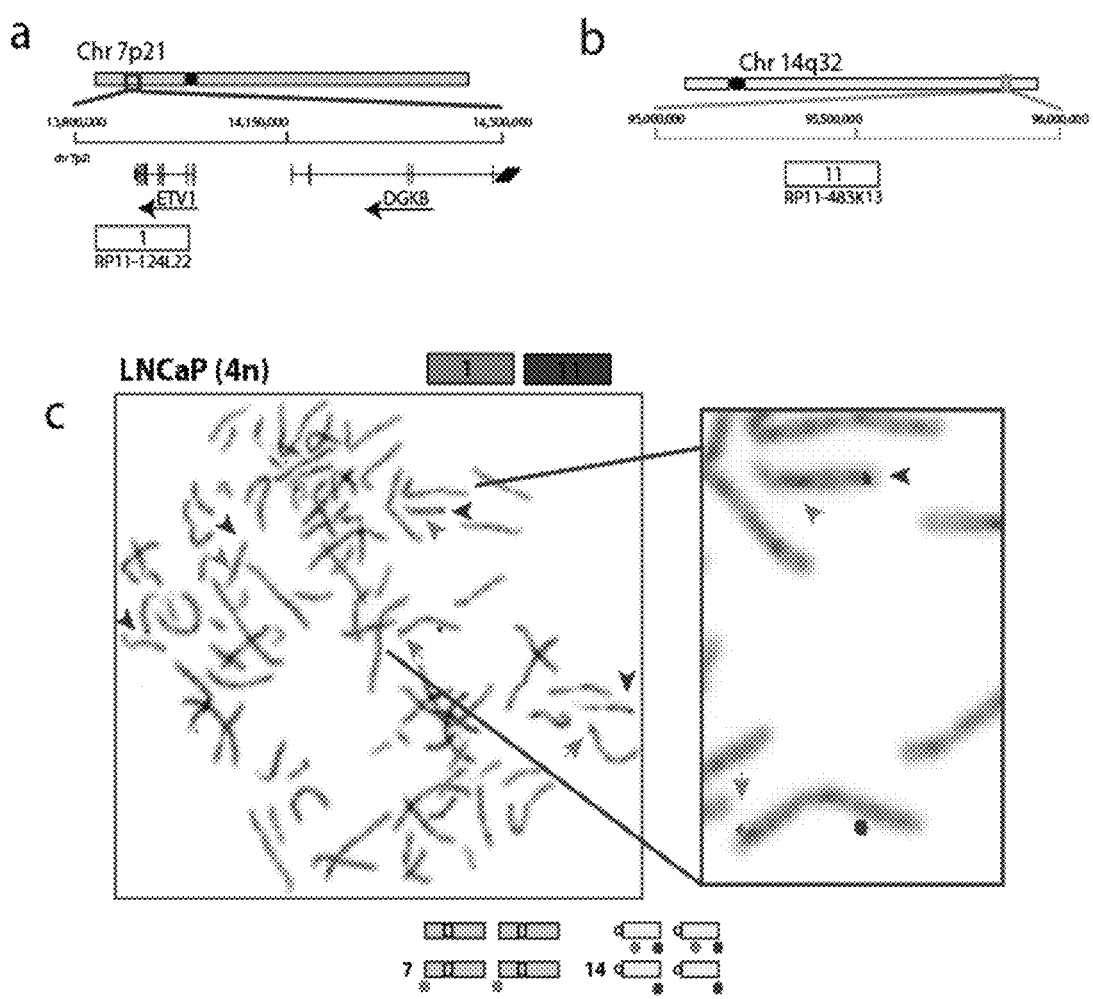
FIG. 2 shows that the ETV1 locus is rearranged to chromosome 14 in LNCaP cells.

On LNCaP metaphases, this assay revealed two pairs of co-localizing signals at the ETV1 locus on 7p, and two split signals where the 5' signals remained on 7p, while two copies of the ETV1 locus were inserted into another chromosome (FIG. 1c). This rearrangement in 2 of 4 copies of chromosome 7 is consistent with other rearrangements observed by G-banding or spectral karyotyping (SKY) in tetraploid LNCap cells (Beheshti et al., Mol Diagn 5, 23-32 (2000); Beheshti et al., Neoplasia 3, 62-9 (2001); Gibas et al., Cancer Genet Cytogenet 11, 399-404 (1984); van Bokhoven et al., Prostate 57, 226-44 (2003)). Cytogenetic analysis indicated that ETV1 was inserted into chromosome 14, and this was confirmed by using a FISH mapped BAC previously localized to 14q (FIG. 2). Subsequent FISH assays were used to determine that the break on chromosome 7 was localized completely 5' to the ETV1 locus, consistent with RACE revealing over-expression of full length ETV1 (FIG. 3).

To localize the breakpoint, Southern blotting was performed using 22 probes across the implicated region of 7p. Genomic DNA (10 μg) was digested with EcoRI or PstI (New England Biologicals, Ipswich, Mass.) overnight. Fragments were resolved on a 0.8% agarose gel at 40 V overnight, transferred to a nylon membrane (Hybond NX), prehybridized, hybridized with probe and washed according to standard laboratory procedures. A series of 22 probes spanning the region of chr 7 implicated by FISH (between RP11-313C20 and RP11-703A4) were generated by PCR amplification using pooled normal human male genomic DNA as template, a high fidelity polymerase enzyme (Platinum Taq High Fidelity), and primers listed in Table 1. Twenty-five ng of each probe was labeled with dCTP-P32 and used for hybridization.

Figure 3:
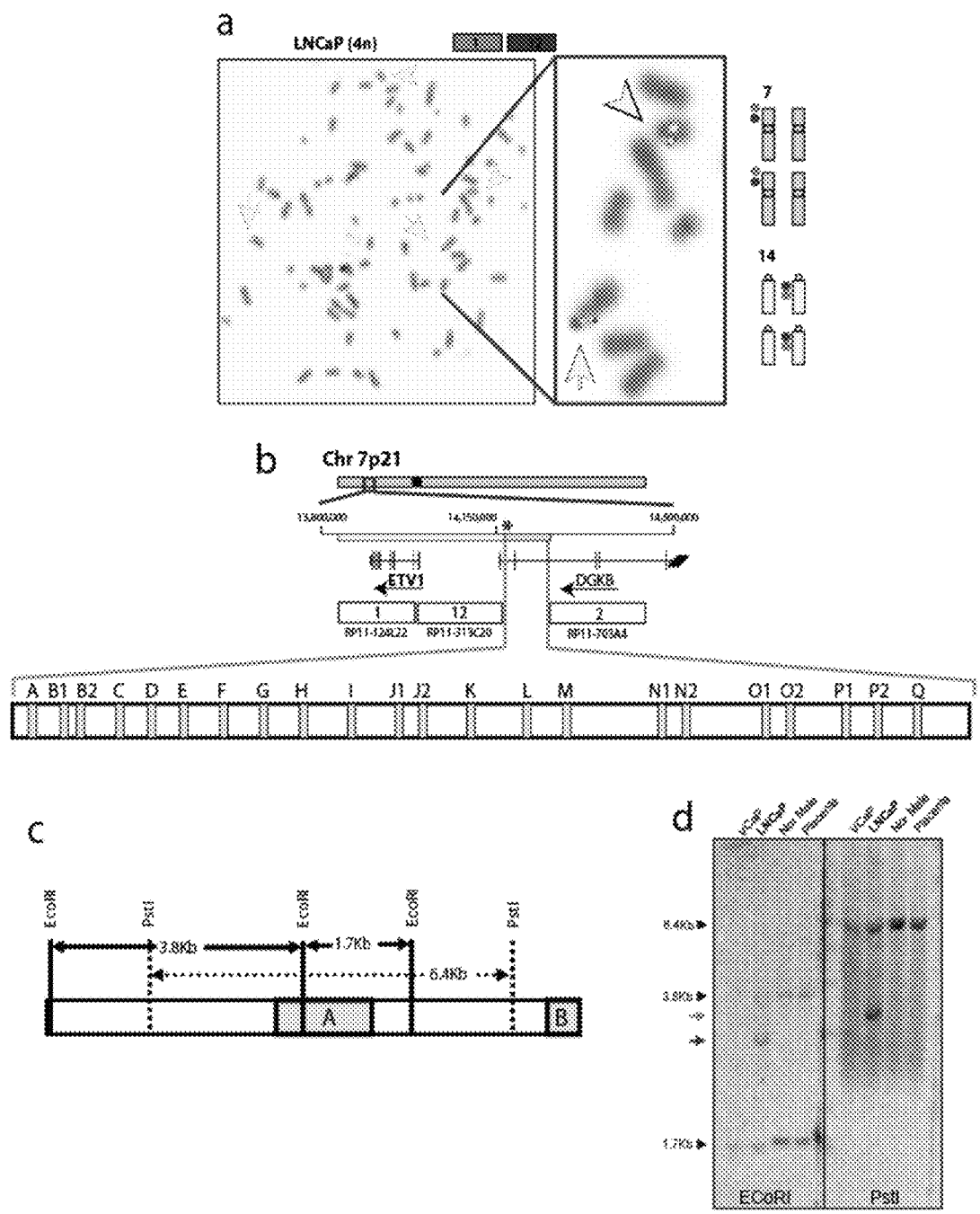
FIG. 3 shows the identification of the genomic breakpoint at the ETV1 locus in LNCaP cells.

A single probe (Probe A, see Table 1, "Southern Probe") showed evidence of a rearrangement, with both EcoRI and PstI digested LNCaP DNA showing additional bands (FIG. 3).

Figure 4:
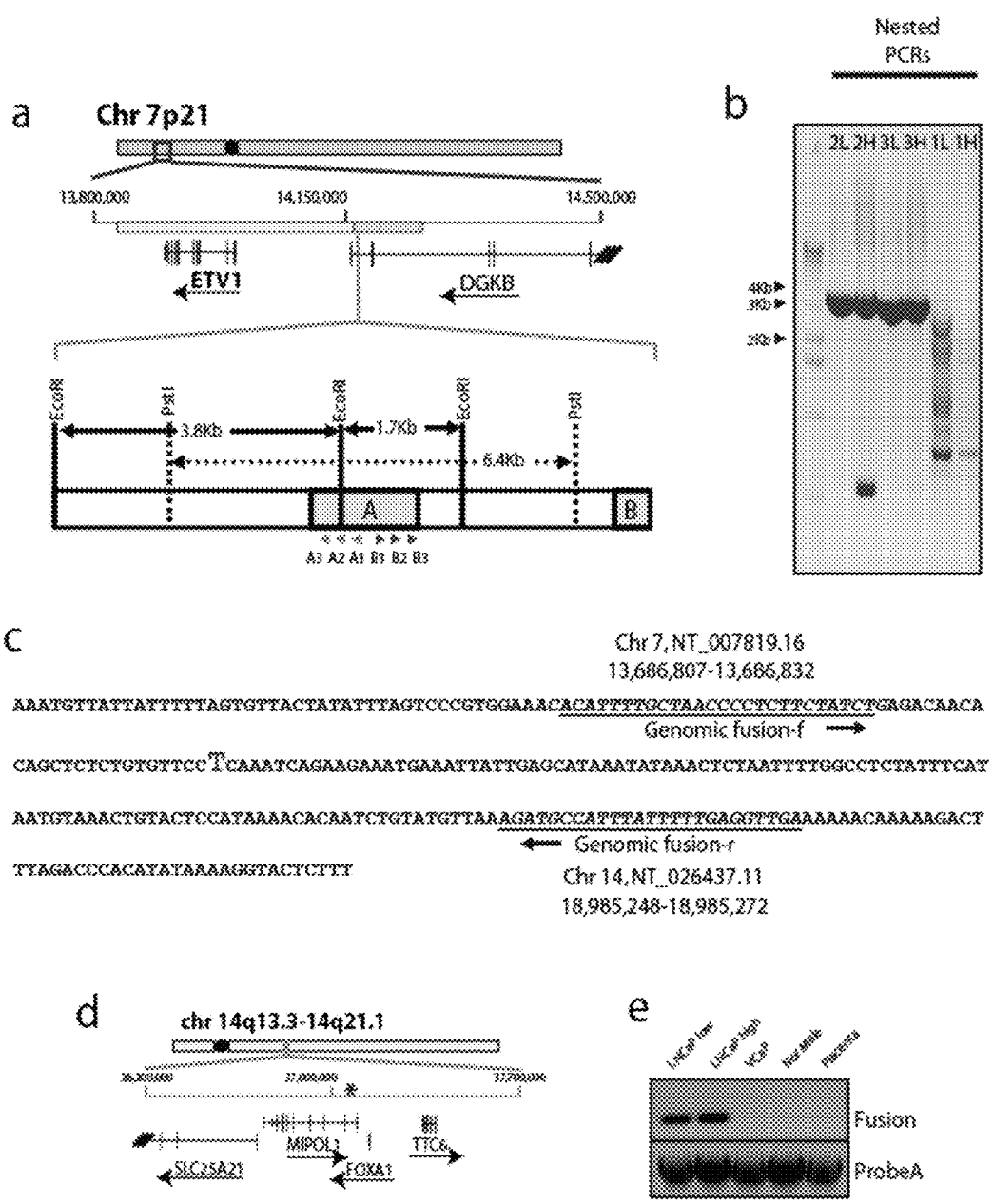
FIG. 4 shows inverse PCR that identifies the insertion of ETV1 into the MIPOL1 locus on chromosome 14.

PstI digested DNA was then used for inverse PCR to identify the genomic breakpoint sequence on chromosome 7 as well as the partner sequence (FIG. 4). Primers A1, A2, A3, which are reverse complemented from the wildtype sequence and are divergent to primers B1, B2, B3, were used for inverse PCR on PstI digested DNA and religated (intramolecular ligation) using the LNCaP genomic DNA template. Nested PCRs were performed in the following order of primer combinations: A1 and B1, then A2 and B2, and finally A3 and B3. The fusion product was amplified using PCR amplification and standard laboratory procedures (Expand 20 kbplus PCR System, Roche Diagnostics GmbH, Mannheim, Germany, used according to the manufacturor's instructions). The enriched 3 Kb band observed in nested PCRs was cloned into a vector (pCR8/GW/TOPO, Invitrogen), and DNA isolated from various clones were screened for inserts and positive clones were sequenced using standard laboratory procedures (by the University of Michigan DNA Sequencing Core Laboratory, Ann Arbor, Mich.). Clones of the fusions sequences were confirmed by PCR amplification (Platinum Taq High Fidelity system) using fusion specific primers (genomic fusion f and r; Table 1).

Figure 5:
FIG. 5 shows that the 7p telomere is retained on all copies of chromosome 7 in LNCaP, by using FISH performed using chromosome 7 centromeric and 7p telomere probes on LNCaP metaphases. All four copies of chromosome 7 identified by the centromeric probes retained their 7p telomeric sequence, demonstrating that the ETV1 rearrangement is not a translocation nor involves a telomeric deletion at 7p.

Sequencing of the amplified product confirmed the breakpoint on chromosome 7p located in a region identified by using Southern blotting, and the insertion point was an intronic sequence from the MIPOL1 locus at chromosome 14q13.3-14q21.1 (FIGS. 1b and 4), consistent with the results obtained by FISH analysis described above. This rearrangement was confirmed by PCR amplification of a product made by using undigested LNCaP genomic DNA as template, isolated from two different passages, while no product was amplified from VCaP, normal male, or normal placental genomic DNA (FIG. 4). Consistent with cytogenetic and SKY data revealing no gross rearrangements in chromosomes 7 or 14 in LNCaP cells29-32, FISH analysis using split probes around the 14q13.3-14q21.1 locus showed co-localized signals (FIG. 1c). These results are consistent with the interpretation that a limited insertion occurred around ETV1, or the entire 7p arm telomeric to ETV1 (approximately 14 MB) was deleted. The latter possibility was ruled out because high density aCGH did not reveal the presence of any deletions telomeric to ETV1, and FISH demonstrated intact 7p telomeric sequence on all copies of chromosome 7 (FIG. 5). Therefore, these results confirm a cryptic insertion of a minimal region around ETV1 into 14q13.3-14q21.1 in LNCaP.

Additional prostate cancer cell lines were tested to screen for ERG and ETV1 expression by quantitative PCR (qPCR), to identify additional genetic rearrangements. The following cells were tested: an immortalized benign prostate epithelial cell line (RWPE) and 8 prostate cancer cell lines (MDA-PCa 2B, LNCaP, VCaP, LAPC4, 22Rv1, NCI-H660, PC3 and DU145). Quantitative PCR (QPCR) was performed by using the oligonucleotide primers shown in Table 1 ("Fusion QPCR" and "Androgen QPCR" sections) with standard laboratory procedures and reagents (Power SYBR Green Mastermix and 7300 Real Time PCR system, Applied Biosystems, Foster City, Calif.). All oligonucleotide primers were synthesized by standard methods (performed by Integrated DNA Technologies, Coralville, Iowa). HMBS and GAPDHS, and PSA6 primers were as described previously (Vandesompele et al., Genome Biol. 3:RESEARCH0034 (2002); Specht et al., Am J. Pathol. 158: 419 (2001)). Androgen stimulation reactions were performed in quadruplicate, and all other reactions were performed in duplicate.

Figure 7:
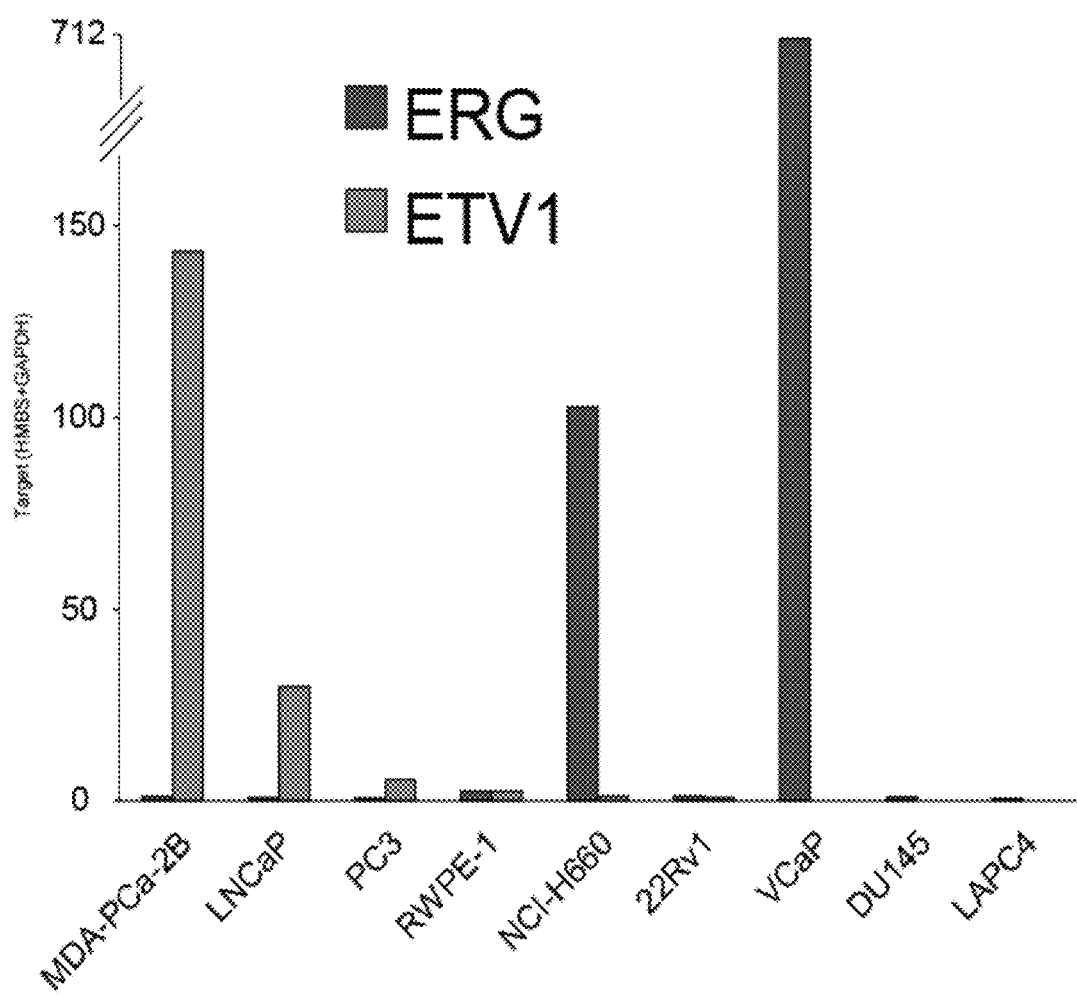
FIG. 7 shows that MDA-PCa 2B has outlier expression of ETV1, in which expression of ERG and ETV1 was determined by qPCR for the prostate cancer cell lines MDA-PCa 2B, LNCaP, PC3, NCI-H660, 22RV1, VCaP, DU145, LAPC4 and the immortalized benign prostate epithelial cell line RWPE, and the amounts of ERG and ETV1 for each sample were normalized to the average amount of GAPDH and HMBS for each sample.

Marked over-expression of ETV1 was detected in LNCaP3 cells, and over-expression of ERG was detected in VCaP and NCI-H660 cells, which are both TMPRSS2:ERG positive (Tomlins et al., Science 310, 644-8 (2005)). Results showed that MDA-PCa 2B cells expressed higher levels of ETV1 than LNCaP cells (FIG. 7).

MDA-PCa 2B cells were also analyzed for genetic rearrangement involving the ETV1 locus. Analysis by RLM-RACE revealed only full-length ETV1 made in MDA-PCa 2B cells, indicating that rearrangement involves the entire ETV1 locus. A previous SKY and G-banding analysis of DNA from MDA-PCa 2B cells demonstrated the presence of a balanced t(7;14)(p21;q21)32, the locations of the ETV1 and MIPOL1 loci. The same FISH analysis was performed for MDA-PCa 2B cells as described above for LNCaP cells, using split probes around the ETV1 locus and the 14q13.3-14q21.1 regions. The results demonstrated that MDA-PCa 2B cells also harbor a rearrangement involving ETV1, in which the whole ETV1 locus is translocated to the d14 chromosome (FIG. 1d). FISH revealed that the 1.5 MB 14q13.3-14q21.1 region is the partner of this balanced translocation, as the telomeric 14q13.3-14q21.1 probe is translocated to the d7 chromosome (FIG. 1d).

Example 2

Aberrant Expression of ETV1 Associated with Genetic Rearrangements

This example shows that region 14q13.3-14q21.1 is coordinately regulated in prostate cancer and LNCaP cells.

The existence of mechanistically distinct rearrangements resulting in the localization of ETV1 to 14q13.3-14q21.1 (FIG. 1, e-g) in prostate cancer cell lines with outlier expression of ETV1 indicates that elements at this region mediate aberrant ETV1 transcription. The structure of the genetic rearrangement in LNCaP cells indicates that ETV1 does not acquire a new proximal promoter after insertion into the 14q13.3-14q21.1 locus because approximately 200kb of the 5' upstream sequence is inserted along with the ETV1 locus (see FIG. 1a). Furthermore, while expression of MIPOL1 in the prostate has not been described, FOXA1, immediately adjacent to MIPOL1, is strongly expressed throughout human and murine prostate development and acts as a transcriptional potentiator for androgen-regulated gene expression (Mirosevich et al., Prostate 66, 1013-28 (2006); Mirosevich et al., Prostate 62, 339-52 (2005)). Over-expression of ETV1 in these lines may be driven by enhancer elements that confer coordinated prostate specificity or androgen regulation to this region. To test this hypothesis, the expression of four contiguous transcripts in the 1.5 MB 14q13.3-14q21.1 region (SLC25A21, MIPOL1, FOXA1 and TTC6) was assessed using data in the expO dataset (International Genomics Consortium (IGC) expression project for Oncology (expO)). The expO dataset is a multi-tumor gene expression dataset generated by a consortium of labs including TGEN and has been included in Oncomine (Rhodes et al., Neoplasia 6, 1-6 (2004)). All four transcripts showed significant over-expression in prostate cancer compared to all other cancers (FIG. 6a). Furthermore, when all measured genes on chromosome 14 were ranked by significant over-expression in prostate cancer compared to all other cancers in this data set, MIPOL1 ranked second, FOXA1 ranked fifth, and TTC6 ranked twenty-third.

Although all four transcripts were over-expressed in prostate cancer, stimulation of LNCaP with R1881 minimally increased the expression of FOXA1 (1.3 fold, p=0.05), while SLC25A21 (0.75 fold, p=0.008), MIPOL1 (1.2 fold, p=0.08) and TTC6 (0.70 fold, p=0.10) showed no significant change or reduced expression following R1881 stimulation (FIG. 6b). However, stimulation of LNCaP with R1881 resulted in significantly increased expression of ETV1 (1.8 fold, p=0.0004, FIG. 6c), indicating that rearrangement to this region confers androgen-responsiveness to ETV1, in addition to aberrant expression. Together, these results show coordinated over-expression in prostate cancer for the genes in this region (and ETV1 when inserted therein), with additional regulation mediated by androgen.

Figure 6:
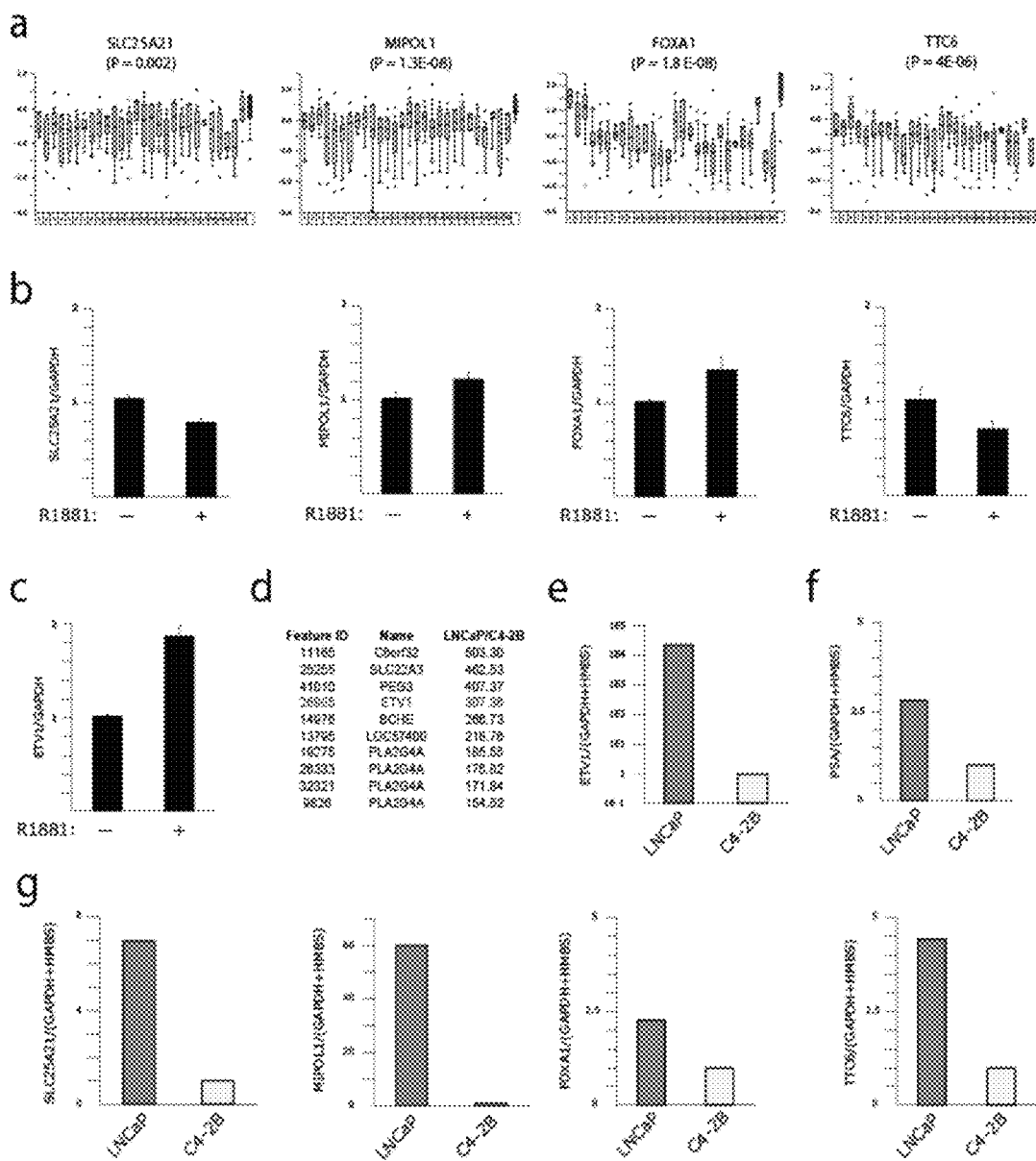
FIG. 6 shows that ETV1 and the contiguous genes at 14q13.3-14q21.1 are coordinately regulated in prostate cancer, LNCaP and the androgen insensitive LNCaP derivative C4-2B.
Figure 8:
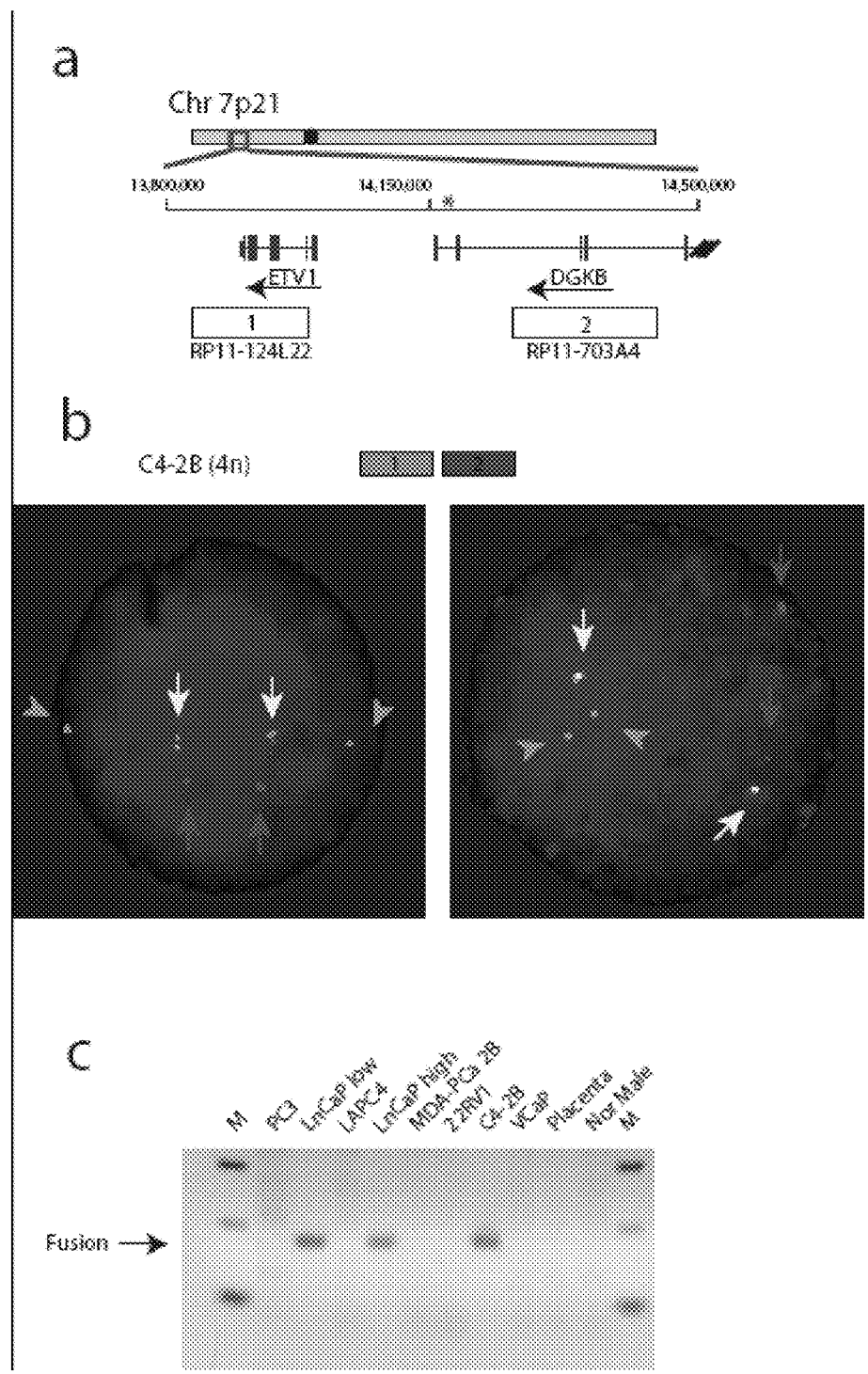
FIG. 8 shows that the LNCaP androgen insensitive derivative C4-2B harbors the same ETV1 rearrangement as the parental LNCaP cell line.

To model progression to hormone refractory metastatic disease, LNCaP cells have previously been cultured in the absence of androgen and clones were selected that are insensitive to androgen. These model systems thus are related to expression levels of genetic components and androgen regulated expression of genetic components in the cells, which would include ETV1 and genes at the 14q13.3-14q21.1 region contained in the LNCaP cell line and the derived clones made from this cell line. Our investigation of all of these independently derived cell lines for which publicly available expression profiling data is available, ETV1 shows marked down-regulation in androgen insensitive derivatives of LNCaP36-39 cells. To confirm these findings, gene expression in LNCaP and its androgen insensitive derivative C4-2B40 were profiled by using a hybridization based assay to examine gene expression (Agilent Whole Genome Microarrays). As shown in FIG. 6d, ETV1 was the fourth most over-expressed feature in LNCaP compared to C4-2B (307-fold difference). When measured by using qPCR, the marked down-regulation of ETV1 in C4-2B (about 22,500 fold), compared to the parental LNCaP cell line was confirmed (FIG. 6e). Furthermore, qPCR also demonstrated that C4-2B cells express less PSA (3-fold less) and the four genes at 14q13.3-14q21.1, when compared to LNCaP cells (FIG. 6, f-g). These results demonstrate coordinated regulation of androgen induced genes and genes at 14q13.3-14q21.1. These results indicate that ETV1 is markedly down-regulated in androgen insensitive LNCaP derivatives either due to deletion or transcriptional mechanisms, or clones that do not harbor the ins(7;14) are selected by using the androgen deprivation method used to derive these clones from the LNCaP cell line. By using FISH and PCR analysis on genomic DNA, the data confirmed that C4-2B cells harbor the same ETV1 rearrangement as LNCaP cells (FIG. 8), leading to the conclusion that the down-regulation of ETV1 is due to mutation or transcriptional changes in the derivative clones.

TABLE 1

| Assay | Gene/ Region | Sequence (Accession No.) | Bases Within Sequence | Primer Name | Oligo- nucleotide Sequence (5' to 3') | SEQ ID NO |
|---|---|---|---|---|---|---|
| Androgen/ Expression QPCR | ETV1 | NM_004956.3 | 624-645 | ETV1_exon_6-7_f | CTACCCCATGGACCACAGATTT | 1 |
| Androgen/ Expression QPCR | ETV1 | NM_004956.3 | 771-750 | ETV1_exon_6-7_r | CTTAAAGCCTTGTGGTGGGAAG | 2 |
| Expression QPCR | ERG | NM_004449.3 | 574-597 | ERG_exon_5-6_f | CGCAGAGTTATCGTGCCAGCAGAT | 3 |
| Expression QPCR | ERG | NM_004449.3 | 659-636 | ERG_exon_5-6r | CCATATTCTTTCACCGCCCACTCC | 4 |
| RLM-RACE | NA | | NA | Generacer 5'_f | CGACTGGAGCACGAGGACACTGA | 5 |
| RLM-RACE | ETV1 | NM_004449.3 | 374-351 | ETV1_exon 4-5_r | CATGGACTGTGGGGTTCTTTCTTG | 6 |
| RLM-RACE | ETV1 | NM_004449.3 | 735-710 | ETV1_exon 7-r | AGACATCTGGCGTTGGTACATAGGAC | 7 |
| Fusion QPCR | HERV-K_22q11.23 | BC020811.1 | 303-327 | HERV-K:ETV1f | GAGTCCCAAGTACGTCCACGGTCAG | 8 |
| Fusion QPCR | ETV1 | NM_004956.3 | 371-345 | HERV-K:ETV1-r | GGACTGTGGGGTTCTTTCTTGATTTTC | 9 |
| Fusion QPCR | HNRPA2B1 | NM_002137.2 | 136-155 | HNRPA2B1:ETV1-f | TGCGGGAAATCGGGCTGAAG | 10 |
| Fusion QPCR | ETV1 | NM_004956.3 | 181-154 | HNRPA2B1:ETV1-r | TTTTCCTGACATTTGTTGGTTTCTCGTT | 11 |

TABLE 1-continued

| Assay | Gene/Region | Sequence (Accession No.) | Bases Within Sequence | Primer Name | Oligonucleotide Sequence (5' to 3') | SEQ ID NO |
|---|---|---|---|---|---|---|
| Fusion QPCR | SLC45A3 | NM_033102.2 | 74-92 | SLC45A3:ETV1-f | CGCTGGCTCCGGGTGACAG | 12 |
| Fusion QPCR | ETV1 | NM_004956.3 | 366-340 | SLC45A3:ETV1-r | GTGGGGTTCTTTCTTGATTTTCAGTGG | 13 |
| Fusion QPCR | C15ORF21 | NM_001005266.1 | 313-336 | C15ORF21:ETV1-f | CAACTAACACTGCGGCTTCCTGAG | 14 |
| Fusion QPCR | ETV1 | NM_004956.3 | 483-461 | C15ORF21:ETV1-r | CATTCCCACTTGTGGCTTCTGAT | 15 |
| Androgen QPCR | TMPRSS2 | NM_005656.2 | 1539-1563 | TMPRSS2-f | CAGGAGTGTACGGGAATGTGATGGT | 16 |
| Androgen QPCR | TMPRSS2 | NM_005656.2 | 1608-1585 | TMPRSS2-r | GATTAGCCGTCTGCCCTCATTTGT | 17 |
| Androgen QPCR | TTC6 | NM_001007795.1 | 1080-1108 | TTC6-f | TGCCATGAAGATCAGTACTACAGCAGAAT | 18 |
| Androgen QPCR | TTC6 | NM_001007795.1 | 1150-1125 | TTC6-r | GTGGCCCATAAACTCATGAATCACC | 19 |
| Androgen QPCR | SLC25A21 | NM_030631.1 | 356-377 | SLC25A21-f | CAGATCGTGGCCGGTGGTTCT | 20 |
| Androgen QPCR | SLC25A21 | NM_030631.1 | 408-483 | SLC25A21-r | GGGTGCATCAGGCAAATTTCTACAAG | 21 |
| Androgen QPCR | MIPOL1 | NM_138731.2 | 1607-1633 | MIPOL1-f | CAACAACAAAATGAGGAACTGGCTACT | 22 |
| Androgen QPCR | MIPOL1 | NM_138731.2 | 1673-1649 | MIPOL1-r | ATTCCATATTTGCTCGCTCTGTCAG | 23 |
| Androgen QPCR | FOXA1 | NM_004496.2 | 327-350 | FOXA1-f | GAAGATGGAAGGGCATGAAACCAG | 24 |
| Androgen QPCR | FOXA1 | NM_004496.2 | 408-389 | FOXA1-r | GCTGACCGGGACGGAGGAGT | 25 |
| Androgen QPCR | SLC45A3 | NM_033102.2 | 1223-1242 | SLC45A3-f | TCGTGGGCGAGGGGCTGTA | 26 |
| Androgen QPCR | SLC45A3 | NM_033102.2 | 1308-1284 | SLC45A3-r | CATCCGAACGCCTTCATCATAGTGT | 27 |
| Androgen QPCR | HERV-K_22q11.23 | BC020811.1 | 168-194 | HERV-K_22q11.23-f | CTTTTCTCTAGGGTGAAGGGACTCTCG | 28 |
| Androgen QPCR | HERV-K_22q11.23 | BC020811.1 | 263-238 | HERV-K_22q11.23-r | CTTCACCCACAAGGCTCACTGTAGAC | 29 |
| Androgen QPCR | HNRPA2B1 | NM_002137.2 | 594-620 | HNRPA2B1-f | GCTTTGGCTTTGTTACTTTTGATGACC | 30 |
| Androgen QPCR | HNRPA2B1 | NM_002137.2 | 693-665 | HNRPA2B1-r | GCCTTTCTTACTTCTGCATTATGACCATT | 31 |
| Androgen QPCR | C15ORF21 | NM_001005266.1 | 219-243 | C15ORF21-f | AAGGACGTGCAAGGATGTTTTTATT | 32 |
| Androgen QPCR | C15ORF21 | NM_001005266.1 | 293-274 | C15ORF21-r | ATGGGAAGATGGGGCTGTT | 33 |
| Southern probe | Chr 7 (5 to ETV1) | NT_007819.16 | 13,685,335-13,685,364 | LNCAP_A-f | GTCAATGGCTAAAAGATGGATAAAAGTGGA | 34 |
| Southern probe | Chr 7 (5' to ETV1) | NT_007819.16 | 13,686,833-13,686,804 | LNCAP_A-r | CAGATAGAAGAGGGGTTAGCAAAATGTGTT | 35 |
| Southern probe | Chr 7 (5' to ETV1) | NT_007819.16 | 13,690,754-13,690,779 | LNCAP_B1-f | CAGAAGGCAAATGTGAGAGGATAGTC | 36 |

TABLE 1-continued

| Assay | Gene/Region | Sequence (Accession No.) | Bases Within Sequence | Primer Name | Oligo-nucleotide Sequence (5' to 3') | SEQ ID NO |
|---|---|---|---|---|---|---|
| Southern probe | Chr 7 (5' to ETV1) | NT_007819.16 | 13,691,679-13,691,657 | LNCAP_B1-r | CTGGATCTGTAACACCCGTGAGC | 37 |
| Southern probe | Chr 7 (5' to ETV1) | NT_007819.16 | 13,693,600-13,693,625 | LNCAP_B2-f | AAAAAGCAAAGACAAGACCGTGGATT | 38 |
| Southern probe | Chr 7 (5' to ETV1) | NT_007819.16 | 13,695,054-13,695,028 | LNCAP_B2-r | GAACTACCTGCGTGCTGACTTGGAGAT | 39 |
| Southern probe | Chr 7 (5' to ETV1) | NT_007819.16 | 13,699,772-13,699,801 | LNCAP_C-f | AAAAGGCAAAGAGGGGTTAAAACATACATA | 40 |
| Southern probe | Chr 7 (5' to ETV1) | NT_007819.16 | 13,700,641-13,700,618 | LNCAP_C-r | AACCCCTCCTTCCACTTCTCCACT | 41 |
| Southern probe | Chr 7 (5' to ETV1) | NT_007819.16 | 13,705,005-13,705,034 | LNCAP_D-f | TGGAGGCATAGAAAAGCTGAGAAATAAG | 42 |
| Southern probe | Chr 7 (5' to ETV1) | NT_007819.16 | 13,705,856-13,705,830 | LNCAP_D-r | TTGGTGCTAGAAGAACTGGGAGAAAC | 43 |
| Southern probe | Chr 7 (5' to ETV1) | NT_007819.16 | 13,711,263-13,711,291 | LNCAP_F-f | GAAAGTCAGGGGCACATATAGATTAGAG | 44 |
| Southern probe | Chr 7 (5' to ETV1) | NT_007819.16 | 13,712,112-13,712,089 | LNCAP_F-r | GCCTTCCCCATACAGTTTCTCCTT | 45 |
| Southern probe | Chr 7 (5' to ETV1) | NT_007819.16 | 13,708,247-13,708,275 | LNCAP_E-f | AAGTTCGTTAAGCCCAGGATCGTAGGTA | 46 |
| Southern probe | Chr 7 (5' to ETV1) | NT_007819.16 | 13,709,539-13,709,514 | LNCAP_E-r | ATATGAAGCCAGCAGCCAGGTAGCA | 47 |
| Southern probe | Chr 7 (5' to ETV1) | NT_007819.16 | 13,719,560-13,719,587 | LNCAP_G-f | TTAGATAAACTGAAAGCCGAACCTGAAC | 48 |
| Southern probe | Chr 7 (5' to ETV1) | NT_007819.16 | 13,720,465-13,720,441 | LNCAP_G-r | CAAACTGGCAAGCAATGTGAACTGT | 49 |
| Southern probe | Chr 7 (5' to ETV1) | NT_007819.16 | 13,723,583-13,723,615 | LNCAP_H-f | TCACCGACAAAACCCATAGAGAAAGAGT | 50 |
| Southern probe | Chr 7 (5' to ETV1) | NT_007819.16 | 13,724,850-13,724,823 | LNCAP_H-r | TTAAATGGTGAGGCAATGAGGAAAGTG | 51 |
| Southern probe | Chr 7 (5' to ETV1) | NT_007819.16 | 13,727,707-13,727,735 | LNCAP_I-f | TTGCTCATTCTCTTTCTCCCCTACACTAA | 52 |
| Southern probe | Chr 7 (5' to ETV1) | NT_007819.16 | 13,729,407-13,729,387 | LNCAP_I-r | TCCCCACCACCAACCATCCTC | 53 |
| Southern probe | Chr 7 (5' to ETV1) | NT_007819.16 | 13,730,208-13,730,233 | LNCAP_J1-f | CTGGGGGAAAAGCAAGTAGGAAAGTA | 54 |
| Southern probe | Chr 7 (5' to ETV1) | NT_007819.16 | 13,731,073-13,731,047 | LNCAP_J1-r | ACAAGAGTTAGTCACGGCAAAGGAGTT | 55 |
| Southern probe | Chr 7 (5' to ETV1) | NT_007819.16 | 13,733,199-13,733,220 | LNCAP_J2-f | GCCCTTTGCCCATGAGAACTAA | 56 |
| Southern probe | Chr 7(5 to ETV1) | NT_007819.16 | 13,734,028-13,734,003 | LNCAP_J2-r | TCCCAGAAGAGATGATATGAGGTGTC | 57 |
| Southern probe | Chr 7 (5' to ETV1) | NT_007819.16 | 13,737,858-13,737,881 | LNCAP_K-f | TCAGTCCCATCTCCCCCTAAACCA | 58 |
| Southern probe | Chr 7 (5' to ETV1) | NT_007819.16 | 13,739,203-13,739,180 | LNCAP_K-r | CACCATTCTCACCCGACCACATTG | 59 |
| Southern probe | Chr 7(5' to ETV1) | NT_007819.16 | 13,743,031-13,743,060 | LNCAP_L-f | TGTAAACTGCAATGAAAAGAAAAGAAAAG | 60 |
| Southern probe | Chr 7(5' to ETV1) | NT_007819.16 | 13,744,016-13,743,987 | LNCAP_L-r | CAAGAGATGGGAGAGGAAGAATGAATAATA | 61 |

TABLE 1-continued

| Assay | Gene/Region | Sequence (Accession No.) | Bases Within Sequence | Primer Name | Oligo-nucleotide Sequence (5' to 3') | SEQ ID NO |
|---|---|---|---|---|---|---|
| Southern probe | Chr 7 (5' to ETV1) | NT_007819.16 | 13,746,316-13,746,343 | LNCAP_M-f | CTATCTAGTCCCTTACGCTTTCCCTGTG | 62 |
| Southern probe | Chr 7 (5' to ETV1) | NT_007819.16 | 13,747,138-13,747,116 | LNCAP_M-r | CATTAGCATTTGGCCTTTGGTCA | 63 |
| Southern probe | Chr 7 (5' to ETV1) | NT_007819.16 | 13,754,560-13,754,584 | LNCAP_N1-f | TGCCTCCCCATAAGTCACCAATCTC | 64 |
| Southern probe | Chr 7 (5' to ETV1) | NT_007819.16 | 13,755,734-13,755,705 | LNCAP_N1-r | CCTGTATTCTAACCCTGGACTTCTCATCAA | 65 |
| Southern probe | Chr 7 (5' to ETV1) | NT_007819.16 | 13,756,219-13,756,246 | LNCAP_N2-f | CTTGTTTATTGGCCTAGTCCTTTGTGCT | 66 |
| Southern probe | Chr 7 (5' to ETV1) | NT_007819.16 | 13,757,204-13,757,179 | LNCAP_N2-r | GCTTTGTGGGTAGTCCTGTCTGAGTG | 67 |
| Southern probe | Chr 7 (5' to ETV1) | NT_007819.16 | 13,760,623-13,760,642 | LNCAP_O1-f | GGCCCATCCCGGTTTGCTAA | 68 |
| Southern probe | Chr 7 (5' to ETV1) | NT_007819.16 | 13,761,824-13,761,798 | LNCAP_O1-r | GTTTCCCCACCACTTCCTTTCTATGTC | 69 |
| Southern probe | Chr 7 (5' to ETV1) | NT_007819.16 | 13,764,545-13,764,569 | LNCAP_O2-f | GCACAAGACATACACGCAGATACAC | 70 |
| Southern probe | Chr 7 (5' to ETV1) | NT_007819.16 | 13,765,703-13,765,678 | LNCAP_O2-r | AACGCTGGACTATGGAACTTTACCTG | 71 |
| Southern probe | Chr 7 (5' to ETV1) | NT_007819.16 | 13,767,646-13,767,674 | LNCAP_P1-f | TCCTCTCATTCATTTTGCATTCGTGTTAG | 72 |
| Southern probe | Chr 7 (5' to ETV1) | NT_007819.16 | 13,768,845-3213,768,819 | LNCAP_P1-r | GGCTTTGAGGGATTACTGGGTTGTTCT | 73 |
| Southern probe | Chr 7(5' to ETV1) | NT_007819.16 | 13,770,885-13,770,905 | LNCAP_P2-f | GCAGGGCAAAGAAGCAGTAGG | 74 |
| Southern probe | Chr 7 (5' to ETV1) | NT_007819.16 | 13,772,453-13,772,428 | LNCAP_P2-r | GGATCCCAATTTAGTTTCAAGTTACG | 75 |
| Southern probe | Chr 7 (5' to ETV1) | NT_007819.16 | 13,774,561-13,774,586 | LNCAP_Q-f | ATGTGCTGGCTAGATTGGACTGAAAA | 76 |
| Southern probe | Chr 7(5' to ETV1) | NT_007819.16 | 13,775,272-13,775,244 | LNCAP_Q-r | CAATAAAGCTGGAGGGGTGATAAATAAAT | 77 |
| Inverse PCR | Chr 7 (Probe A) | NT_007819.16 | 13,685,817-13,685,793 | Inverse A1 | TTAGAAGGAGACAATCTTATTCCAG | 78 |
| Inverse PCR | Chr 7 (Probe A) | NT_007819.16 | 13685,657-13,685,634 | Inverse A2 | CTCTTAAAGAGATGAAGCAGGGAG | 79 |
| Inverse PCR | Chr 7 (Probe A) | NT_007819.16 | 13,685,626-13,685,603 | Inverse A3 | TTGGCTAGATACAGGGTGAATATT | 80 |
| Inverse PCR | Chr 7 (Probe A) | NT_007819.16 | 13,685,833-13,685,856 | Inverse B1 | TGAATTCATGTGTGTAGCTGAGCC | 81 |
| Inverse PCR | Chr 7 (Probe A) | NT_007819.16 | 13,685,860-13,685,883 | Inverse B2 | TGACAGCGGGAATAAAGTACATGC | 82 |
| Inverse PCR | Chr 7 (Probe A) | NT_007819.16 | 13,686,095-13,686,118 | Inverse B3 | GTTGGGAGGTTTACTTGCCAATTA | 83 |
| Genomic fusion | Chr 7 (5' to ETV1) | NT_007819.16 | 13,686,807-13,686,832 | Genomic fusion-f | ACATTTGCTAACCCCTCTTCTATCT | 84 |
| Genomic fusion | Chr 14 (MIPOL1) | NT_026437.11 | 18,985,248-18,985,272 | Genomic fusion-r | TCAACCTCAAAAATAAATGGCATCT | 85 |
| RWPE-ETV1 | SERPINE1 | NM_000602.1 | 1181-1200 | SERPINE1-f | GCATGGCCCCCGAGGAGAT | 86 |

TABLE 1-continued

| Assay | Gene/Region | Sequence (Accession No.) | Bases Within Sequence | Primer Name | Oligo-nucleotide Sequence (5' to 3') | SEQ ID NO |
|---|---|---|---|---|---|---|
| RWPE-ETV1 | SERPINE1 | NM_000602.1 | 1270-1248 | SERPINE1-r | CTTGGCCCATGAAAGGACTGTT | 87 |
| RWPE-ETV1 | TGFBI | NM_000358.1 | 1506-1528 | TGFBI-f | AGGTACGGGACCCTGTTCACGAT | 88 |
| RWPE-ETV1 | TGFBI | NM_000358.1 | 1605-1580 | TGFBI-r | CTACCAGCATGCTAAAGCGATTGTCT | 89 |
| RWPE-ETV1 | IGFBP3 | NM_000598.4 | 738-762 | IGFBP3-f | CGAGTCCAAGCGGGAGACAGAATA | 90 |
| RWPE-ETV1 | IGFBP3 | NM_000598.4 | 837-814 | IGFBP3-r | TACACCCCTGGGACTCAGCACATT | 91 |
| RWPE-ETV1 | MMP3 | NM_002422.3 | 1055-1080 | MMP3-f | TTCATTTTGGCCATCTCTTCCTTCAG | 92 |
| RWPE-ETV1 | MMP3 | NM_002422.3 | 1181-1155 | MMP3-r | TATCCAGCTCGTACCTCATTTCCTCT | 93 |
| RWPE-ETV1 | SPOCK1 | NM_004598.3 | 829-848 | SPOCK1-f | GCCCACCAGCTCCAACACAG | 94 |
| RWPE-ETV1 | SPOCK1 | NM_004598.3 | 951-928 | SPOCK1-r | GAAGGGTCAAGCAGGAGGTCATAG | 95 |
| RWPE-ETV1 | BCL2 | NM_000633.2 | 1014-1039 | BCL2-f | CCCTGTGGATGACTGAGTACCTGAAC | 96 |
| RWPE-ETV1 | BCL2 | NM_000633.2 | 1084-1064 | BCL2-r | GGCATCCCAGCCTCCGTTATC | 97 |
| RWPE-ETV1 | MMP14 | NM_004995.2 | 1036-1059 | MMP14-f | AATTTTGTGCTGCCCGATGATGAC | 98 |
| RWPE-ETV1 | MMP14 | NM_004995.2 | 1151-1129 | MMP14-r | GGAACAGAAGGCCGGGAGGTAGT | 99 |
| RWPE-ETV1 | MMP2 | NM_004530.2 | 953-974 | MMP2-f | GAAGGCCAAGTGGTCCGTGTGA | 100 |
| RWPE-ETV1 | MMP2 | NM_004530.2 | 1044-1019 | MMP2-r | CAGCTGTTGTACTCCTTGCCATTGAA | 101 |
| RWPE-ETV1 | ADAM19 | NM_023038.3 | 2146-2165 | ADAM19-f | GCCTATGCCCCCTGAGAGTG | 102 |
| RWPE-ETV1 | ADAM19 | NM_023038.3 | 2271-2245 | ADAM19-r | GCTTGAGTTGGCCTAGTTTGTTGTTC | 103 |
| RWPE-ETV1 | MMP9 | NM_004994.2 | 1181-1201 | MMP9-f | TGCCCGGACCAAGGATACAGT | 104 |
| RWPE-ETV1 | MMP9 | NM_004994.2 | 1239-1221 | MMP9-r | AGCGCGTGGCCGAACTCAT | 105 |
| RWPE-ETV1 | PLAU | NM_002658.2 | 1169-1194 | PLAU-f | TACGGCTCTGAAGTCACCACCAAAAT | 106 |
| RWPE-ETV1 | PLAU | NM_002658.2 | 1308-1286 | PLAU-r | CCCCAGCTCACAATTCCAGTCAA | 107 |

TABLE 2

| Probe # | Gene/Region | Localization | Probe |
|---|---|---|---|
| 1 | ETV1 | 3' | RP11-124L22 |
| 2 | ETV1 | 5' | RP11-703A4 |
| 3 | Chr 14q13.3-14q21.1 | C | RP11-945C4 |
| 4 | Chr 14q13.3-14q21.1 | T | RP11-107E23 |
| 5 | HNRPA2B1 3' | 3' | RP11-11F13 |
| 6 | HNRPA2B1 5' | 5' | RP11-379M24 |
| 7 | HERV-K__22q11.23 5' | 5' | RP11-61N10 |
| 8 | HERV-K__22q11.23 3' | 3' | RP11-71G19 |
| 9 | SLC45A3 | 3' | RP11-249h15 |
| 10 | SLC45A3 | 5' | RP11-131E5 |

TABLE 2-continued

| Probe # | Gene/Region | Localization | Probe |
|---|---|---|---|
| 11 | C15ORF21 | 5' | RP11-474E1 |
| 12 | C15ORF21 | 3' | RP11-626F7 |
| 13 | 14q32 | 3' | RP11-483K13 |
| 14 | ETV1 | 5' | RP11-313C20 |
| 15 | Chr 7 centromere | C | CEP 7 |
| 16 | Chr 7p telomere | T | TelVysion 7p |
| 17 | TMPRSS2 | 5' | RP11-35C4 |

All publications, patents, patent applications and sequences identified by accession numbers mentioned in the above specification are herein incorporated by reference in their entirety. Although the invention has been described in connection with specific embodiments, it should be understood that the invention as claimed should not be unduly limited to such specific embodiments. Modifications and variations of the described compositions and methods of the invention that do not significantly change the functional features of the compositions and methods described herein are intended to be within the scope of the following claims.

We claim:

1. A method for detecting a MIPOL1-ETV1 genetic rearrangement and one or more markers associated with prostate cancer in a biological sample, the method comprising:
   a) contacting a biological sample with:
      i) a probe directly labeled with a detectable label and comprising a sequence that is complementary to a junction at which an ETV1 gene is inserted into a MIPOL1 gene; or
      ii) a first probe directly labeled with a detectable label and comprising a sequence complementary to a MIPOL1 gene and a second probe directly labeled with a detectable label and comprising a sequence complementary to an ETV1 gene; or
      iii) a first amplification oligonucleotide comprising a sequence complementary to a MIPOL1 gene, a second amplification oligonucleotide comprising a sequence complementary to an ETV1 gene, and a probe directly labeled with a detectable label and comprising a sequence complementary to the product produced from the first and second primers; and
   b) detecting in the biological sample expression of a marker selected from the set of markers consisting of AMACR/P504S, PCA3, PCGEM1, prostein/P501S, P503S, P504S, P509S, P510S, prostase/P703P, P710P, prostate specific antigen (PSA), prostatic acid phosphatase (PAP), prostate binding protein (PBP), ABCC5 (MDR5), ADAMTS1, AMACR, ANNEXINA11, ANNEXINA1, ANNEXINA4, APP, ARHB, ASNS, ATF2, C1S, C4BPA, C7, CATHEPSINB, CATHEPSINH, CAVEOLIN2, CCND2, CFLAR, CLUSTERIN, COL15A1, COL1A2, COL3A1, c-terminal binding protein, CTBP1, CTBP2, CYSTATINC, E2EPF, EDNRB, EGR1, EPHA1, ETS2, EZH2, FASN, FAT, FHL1, FIBRONECTIN1, FKBP5, FLS353, FOLH1, FOSB, FZD7, GELSOLIN, GP73, GSTM1, GSTM3, GSTM5, GSTP1, HEPSIN, HEVIN, IGFBP3, IGFBP5, IL1R1, IL1R2, ITGA1, ITGB4, ITM2C, JUN, KERATIN5, LIMK1, LUMICAN, MADH4, MAP3K10, MAPK6, MCAM, MEIS1, MEIS2, MMECD10, MOESIN, MPDZ, MTA1, MYBL2, MYLK, NBL1, NCK1, NRAS, PCM1, pim-1, PLA2G2A, PP1CB, PPP2CB, PRKCL2, PSG9, RAB2, RAB5A, RAP2, RIG, S100A11, SCYA2, SEPP1, SGK, SKI, SLUG, TACC1, TASTIN, TBXA2F, TBXA2R, TFCP2, THROMBOSPONDIN1, TIMP2, TNFS10, TNFSF10, TOP2A, TRAF4, TRAP1, UBCH10, VAV2, VIMENTIN, VINCULIN, and YWHAB.

2. The method of claim 1 wherein the marker is a protein.

3. The method of claim 1 wherein the marker is a messenger RNA.

4. The method of claim 1 wherein the marker is a messenger RNA and detecting expression of the marker comprises producing a complementary DNA.

5. The method of claim 1 wherein the amount of the marker is quantified.

6. The method of claim 1 wherein detecting the MIPOL1-ETV1 genetic rearrangement and the one or more markers is associated with the stage, aggressiveness, or progression of prostate cancer or the presence or risk of metastasis in a subject that was the source of the biological sample.

7. The method of claim 1 wherein the biological sample comprises, or comprises a fraction of, a prostate biopsy sample, prostatectomy tissue sample, blood sample, urine sample, semen sample, prostatic secretion sample, plasma sample, serum sample, urine supernatant, urine cell pellet, or prostate cell sample.

8. The method of claim 1 further comprising quantifying ETV1 expression.

9. The method of claim 1 further comprising producing or receiving the biological sample.

10. The method of claim 1 further comprising reporting the presence, absence, or amount of the MIPOL1-ETV1 genetic rearrangement and one or more of the markers.

11. The method of claim 1 further comprising providing an array comprising one or more probes comprising a sequence complementary to the MIPOL1-ETV1 genetic rearrangement and one or more probes comprising a sequence complementary to the set of markers.

12. The method of claim 6 further comprising treating the subject that was the source of the biological sample.

13. A kit for detecting a MIPOL1-ETV1 genetic rearrangement and one or more markers associated with prostate cancer in a biological sample, the kit comprising:
   a) a first component selected from the group consisting of:
      i) a probe directly labeled with a detectable label and comprising a sequence that is complementary to a junction at which an ETV1 gene is inserted into a MIPOL1 gene;
      ii) a first probe directly labeled with a detectable label and comprising a sequence complementary to a MIPOL1 gene and a second probe directly labeled with a detectable label and comprising a sequence complementary to an ETV1 gene; and
      iii) a first amplification oligonucleotide comprising a sequence complementary to a MIPOL1 gene, a second amplification oligonucleotide comprising a sequence complementary to an ETV1 gene, and a probe directly labeled with a detectable label and comprising a sequence complementary to the product produced from the first and second primers; and
   b) a second component comprising a probe directly labeled with a detectable label and for detecting a marker selected from the set of markers consisting of AMACR/P504S, PCA3, PCGEM1, prostein/P501S, P503S, P504S, P509S, P510S, prostase/P703P, P710P, prostate specific antigen (PSA), prostatic acid phosphatase (PAP), prostate binding protein (PBP), ABCC5 (MDR5), ADAMTS1, AMACR, ANNEXINA11, ANNEXINA1, ANNEXINA4, APP, ARHB, ASNS, ATF2, C1S, C4BPA, C7, CATHEPSINB, CATHEPSINH, CAVEOLIN2, CCND2, CFLAR, CLUSTERIN, COL15A1, COL1A2, COL3A1, c-terminal binding protein, CTBP1, CTBP2, CYSTATINC, E2EPF, EDNRB, EGR1, EPHA1, ETS2, EZH2, FASN, FAT, FHL1, FIBRONECTIN1, FKBP5, FLS353, FOLH1, FOSB, FZD7, GELSOLIN, GP73, GSTM1, GSTM3, GSTM5, GSTP1, HEPSIN, HEVIN, IGFBP3, IGFBP5, IL1R1, IL1R2, ITGA1, ITGB4, ITM2C, JUN, KERATIN5, LIMK1, LUMICAN, MADH4, MAP3K10, MAPK6, MCAM, MEIS1, MEIS2, MMECD10, MOESIN, MPDZ, MTA1, MYBL2, MYLK, NBL1, NCK1, NRAS, PCM1, pim-1, PLA2G2A, PP1CB, PPP2CB, PRKCL2, PSG9, RAB2, RAB5A, RAP2, RIG, S100A11, SCYA2, SEPP1, SGK, SKI, SLUG, TACC1, TASTIN, TBXA2F, TBXA2R, TFCP2, THROMBOSPONDIN1, TIMP2, TNFS10, TNFSF10, TOP2A, TRAF4, TRAP1, UBCH10, VAV2, VIMENTIN, VINCULIN, and YWHAB.

14. The kit of claim 13 wherein the probe is a nucleic acid comprising a sequence complementary to the marker.

15. The kit of claim 13 wherein the probe is an antibody specific for the marker.

16. The kit of claim 13 wherein the first component comprises a probe or a pair of probes and an array comprises the first and second components.

17. An assay composition comprising a sample from a subject and:
   a) a first component selected from the group consisting of:
      i) a junction probe directly labeled with a detectable label and comprising a sequence that is complementary to a junction at which an ETV1 gene is inserted into a MIPOL1 gene;
      ii) a first probe directly labeled with a detectable label and comprising a sequence complementary to a MIPOL1 gene and a second probe directly labeled with a detectable label and comprising a sequence complementary to an ETV1 gene; and
      iii) a first amplification oligonucleotide comprising a sequence complementary to a MIPOL1 gene, a second amplification oligonucleotide comprising a sequence complementary to an ETV1 gene, and an amplicon probe directly labeled with a detectable label and comprising a sequence complementary to the amplicon produced from the first and second primers; and
   b) a second component comprising a probe directly labeled with a detectable label and for detecting a marker selected from the set of markers consisting of AMACR/P504S, PCA3, PCGEM1, prostein/P501S, P503S, P504S, P509S, P510S, prostase/P703P, P710P, prostate specific antigen (PSA), prostatic acid phosphatase (PAP), prostate binding protein (PBP), ABCC5 (MDR5), ADAMTS1, AMACR, ANNEXINA11, ANNEXINA1, ANNEXINA4, APP, ARHB, ASNS, ATF2, C1S, C4BPA, C7, CATHEPSINB, CATHEPSINH, CAVEOLIN2, CCND2, CFLAR, CLUSTERIN, COL15A1, COL1A2, COL3A1, c-terminal binding protein, CTBP1, CTBP2, CYSTATINC, E2EPF, EDNRB, EGR1, EPHA1, ETS2, EZH2, FASN, FAT, FHL1, FIBRONECTIN1, FKBP5, FLS353, FOLH1, FOSB, FZD7, GELSOLIN, GP73, GSTM1, GSTM3, GSTM5, GSTP1, HEPSIN, HEVIN, IGFBP3, IGFBP5, IL1R1, IL1R2, ITGA1, ITGB4, ITM2C, JUN, KERATIN5, LIMK1, LUMICAN, MADH4, MAP3K10, MAPK6, MCAM, MEIS1, MEIS2, MMECD10, MOESIN, MPDZ, MTA1, MYBL2, MYLK, NBL1, NCK1, NRAS, PCM1, pim-1, PLA2G2A, PP1CB, PPP2CB, PRKCL2, PSG9, RAB2, RAB5A, RAP2, RIG, S100A11, SCYA2, SEPP1, SGK, SKI, SLUG, TACC1, TASTIN, TBXA2F, TBXA2R, TFCP2, THROMBOSPONDIN1, TIMP2, TNFS10, TNFSF10, TOP2A, TRAF4, TRAP1, UBCH10, VAV2, VIMENTIN, VINCULIN, and WTHAB.

18. The assay composition of claim 17 wherein the second component comprises a probe that is a nucleic acid comprising a sequence complementary to the marker.

19. The assay composition of claim 17 wherein the second component comprises an antibody that is specific for the marker.

20. The assay composition of claim 17 wherein:
   a) said first component is:
      (i) said junction probe and said junction probe is hybridized to said junction; or
      (ii) said first and second probes and said first probe is hybridized to the MIPOL1 gene and said second probe is hybridized to the ETV1 gene; or
      (iii) said first and second amplification oligonucleotides and said amplicon probe, and said first amplification oligonucleotide is hybridized to the MIPOL1 gene and said second amplification oligonucleotide is hybridized to the ETV1 gene; and
   b) the second component is a nucleic acid hybridized to the marker.

21. The assay composition of claim 17 wherein:
   a) said first component is:
      (i) said junction probe and said junction probe is hybridized to said junction; or
      (ii) said first and second probes and said first probe is hybridized to the MIPOL1 gene and said second probe is hybridized to the ETV1 gene; or
      (iii) said first and second amplification oligonucleotides and said amplicon probe, and said first amplification oligonucleotide is hybridized to the MIPOL1 gene and said second amplification oligonucleotide is hybridized to the ETV1 gene; and
   b) the second component is an antibody specifically bound to the marker.

22. The assay composition of claim 17 wherein the first component comprises a first amplification oligonucleotide comprising a sequence complementary to a MIPOL1 gene, a second amplification oligonucleotide comprising a sequence complementary to an ETV1 gene, a probe directly labeled with a detectable label and comprising a sequence complementary to the product produced from the first and second primers, and a polymerase.

\* \* \* \* \*

UNITED STATES PATENT AND TRADEMARK OFFICE
CERTIFICATE OF CORRECTION

PATENT NO. : 10,167,517 B2
APPLICATION NO. : 15/639583
DATED : January 1, 2019
INVENTOR(S) : Arul M. Chinnaiyan, Scott Tomlins and Saravana Mohan Dhanasekaran Page 1 of 1

It is certified that error appears in the above-identified patent and that said Letters Patent is hereby corrected as shown below:

In the Claims

Claim 11 (Column 80, Line 15) reads:
"sequence complementary to the set of markers."
Whereas it should read:
"sequence complementary to one or more markers from the set of markers."

Claim 13 (Column 80, Line 38) reads:
"a second component comprising a probe directly"
Whereas it should read:
"a second component comprising a marker probe directly"

Claim 14 (Column 80, Line 66) reads:
"The kit of claim 13 wherein the probe is a nucleic acid"
Whereas it should read:
"The kit of claim 13 wherein the marker probe is a nucleic acid"

Claim 15 (Column 81, Line 1) reads:
"The kit of claim 13 wherein the probe is an antibody"
Whereas it should read:
"The kit of claim 13 wherein the marker probe is an antibody"

Claim 17 (Column 82, Line 5) reads:
"TIN, VINCULIN, and WTHAB."
Whereas it should read:
"TIN, VINCULIN, and YWHAB."

Signed and Sealed this
Fifth Day of March, 2019

Andrei Iancu
*Director of the United States Patent and Trademark Office*